United States Patent

Barth et al.

Patent Number: 5,925,768
Date of Patent: Jul. 20, 1999

[54] 3-PYRAZOLECARBOXAMIDE DERIVATIVES HAVING CANNABINOID RECEPTOR AFFINITY

[75] Inventors: Francis Barth; Pierre Casellas, both of Montpellier; Joseph Millan, Juvignac; Didier Oustric, Le Cres; Murielle Rinaldi, Georges d'Orques; Martine Sarran, Clarensac, all of France

[73] Assignee: Sanofi, Paris, France

[21] Appl. No.: 09/077,767

[22] PCT Filed: Dec. 6, 1996

[86] PCT No.: PCT/FR96/01953

§ 371 Date: Jun. 3, 1998

§ 102(e) Date: Jun. 3, 1998

[87] PCT Pub. No.: WO97/21682

PCT Pub. Date: Jun. 19, 1997

[30] Foreign Application Priority Data

Dec. 8, 1995 [FR] France .................................. 95 14547

[51] Int. Cl.⁶ ..................... A61K 31/415; C07D 231/14
[52] U.S. Cl. ........................ 548/374.1; 514/406
[58] Field of Search ............... 548/374.1; 514/406

[56] References Cited

FOREIGN PATENT DOCUMENTS 0 576 357  12/1993  European Pat. Off. .
0 656 354   6/1995  European Pat. Off. .
0 658 546   6/1995  European Pat. Off. .

*Primary Examiner*—Robert W. Ramsuer
*Attorney, Agent, or Firm*—Mary P. Bauman; Michael D. Alexander

[57] ABSTRACT

The present invention relates to compounds of the formula

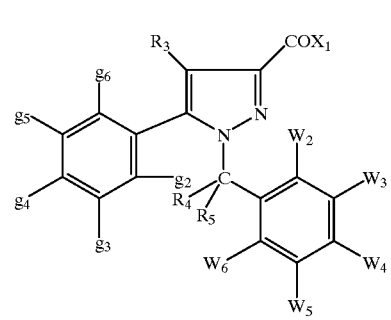

(I)

in which:

$X_1$ is a group $-NR_1R_2$ or a group $-OR_2$;

$g_2$, $g_3$, $g_4$, $g_5$, $g_6$ and $w_2$, $w_3$, $w_4$, $w_5$, $w_6$ are identical or different and are each independently hydrogen, a halogen atom, a ($C_1$–$C_4$)alkyl, a ($C_1$–$C_4$)alkoxy, a trifluoromethyl, a nitro or a ($C_1$–$C_4$)alkylthio, with the proviso that at least one of the substituents $g_2$, $g_3$, $g_4$, $g_5$, $g_6$ and at least one of the substituents $w_2$, $w_3$, $w_4$, $w_5$, $w_6$ are other than hydrogen;

$R_1$ is hydrogen or a ($C_1$–$C_4$)alkyl;

$R_2$ is a non-aromatic ($C_3$–$C_{15}$)carbocyclic radical which is unsubstituted or monosubstituted or polysubstituted by a substituent selected from a halogen atom, a ($C_1$–$C_4$)alkyl and a ($C_1$–$C_4$)alkoxy;

$R_3$ is hydrogen or a group $-CH_2R_6$; and $R_4$ and $R_5$ are each independently a hydrogen, a ($C_1$–$C_4$)alkyl or a trifluoromethyl;

or else $R_4$ is hydrogen and $R_5$ and $w_6$ together constitute an ethylene or trimethylene radical; and $R_6$ is hydrogen, a ($C_1$–$C_4$)alkyl, a fluorine, a hydroxyl, a ($C_1$–$C_5$)alkoxy, a ($C_1$–$C_5$)alkylthio, a hydroxy($C_1$–$C_5$)alkoxy, a cyano, a ($C_1$–$C_5$)alkylsulfinyl or a ($C_1$–$C_5$)alkylsulfonyl with the proviso that when the substituents $g_2$, $g_3$, $g_4$, $g_5$ and/or $g_6$ are a ($C_1$–$C_4$)alkyl $R_6$ is only hydrogen;

to a process for their preparation and to the pharmaceutical compositions in which they are present.

These compounds have a good affinity for the peripheral cannabinoid receptors.

21 Claims, No Drawings

3-PYRAZOLECARBOXAMIDE DERIVATIVES HAVING CANNABINOID RECEPTOR AFFINITY

The present invention relates to novel pyrazole derivatives and their optional salts, to a process for their preparation and to pharmaceutical compositions in which they are present.

More particularly, the present invention relates to novel pyrazole derivatives which possess a very good affinity for the peripheral cannabinoid receptors, called $CB_2$ receptors, and are useful in the therapeutic fields in which the $CB_2$ receptors are involved.

$\Delta^9$-THC is the main active constituent of Cannabis sativa (Tuner, 1985; in Marijuana 1984, Ed. Harvey, DY, IRL Press, Oxford).

The characterization of the cannabinoid receptors has been made possible by the development of synthetic ligands such as the agonists WIN 55212-2 (J. Pharmacol. Exp. Ther., 1993, 264, 1352–1363) or CP 55940 (J. Pharmacol. Exp. Ther., 1988, 247, 1046–1051).

Numerous articles have described not only psychotropic effects of cannabinoids but also their influence on the immune function (HOLLISTER L. E., J. Psychoact. Drugs, 24, 1992, 159–164). The majority of in vitro studies have shown that cannabinoids have immunosuppressant effects: inhibition of the mitogen induced proliferative responses of T lymphocytes and B lymphocytes (Luo Y. D. et al., Int. J. Immunopharmacol., 1992, 14, 49–56; Schwartz H. et al., J. Neuroimmunol., 1994, 55, 107–115), inhibition of the activity of cytotoxic T cells (Klein et al., J. Toxicol. Environ. Health, 1991, 32, 465–477), inhibition of the microbicidal activity of macrophages and of TNFα synthesis (Arata S. et al., Life Sci., 1991, 49, 473–479; Fisher-Stenger et al., J. Pharm. Exp. Ther., 1993, 267, 1558–1565), and inhibition of the cytolytic activity and the TNFα production of certain lymphocytes (Kusher et al., Cell. Immun., 1994, 154, 99–108). In some studies, by contrast, amplification effects have been observed, namely an increase in the bioactivity of interleukin-1 by mouse fixed macrophages or differentiated macrophagic cell lines, due to enhanced levels of TNFα (Zhu et al., J. Pharm. Exp. Ther., 1994, 270, 1334–1339; Shivers S. C. et al., Life Sci., 1994, 54, 1281–1289).

The effects of cannabinoids are due to an interaction with high-affinity specific receptors present in the central nervous system (Devane et al., Molecular Pharmacology, 1988, 34, 605–613) and peripheral nervous system (Nye et al., The Journal of Pharmacology and Experimental Therapeutics, 1985, 234, 784–791; Kaminski et al., Molecular Pharmacology, 1992, 42, 736–742; Munro et al., Nature, 1993, 365, 61–65).

The central effects are dependent on a first type of cannabinoid receptor ($CB_1$), which is present in the brain. Furthermore, Munro et al. (Nature, 1993, 365, 61–65) have cloned a second cannabinoid receptor coupled to proteins G, called $CB_2$, which is present only in the peripheral nervous system and more particularly in the cells of immune origin. The presence of $CB_2$ cannabinoid receptors in the lymphoid cells may explain the immunomodulation, referred to above, which is exerted by cannabinoid receptor agonists.

Numerous pyrazole derivatives have been described in the literature; more particularly, EP-A-268554 and DE-A-3910248 claim pyrazoles which possess herbicidal properties, EP-A-430186 and JP-A-3031840 claim compounds which are useful in photography and EP-A-418845 claims pyrazoles which possess anti-inflammatory, analgesic and antithrombotic activity.

Pyrazolecarboxamide derivatives have also been described, especially in patent applications EP-A-0289879 and EP-A-0492125; these compounds possess insecticidal properties.

Moreover, patent application EP-A-0477049 describes pyrazole-3-carboxamide derivatives of the formula

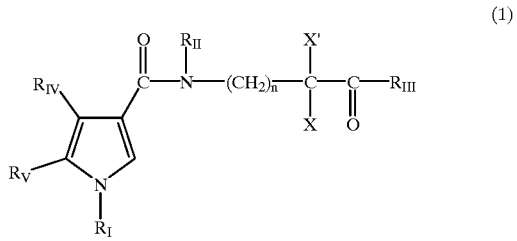

in which for example:
$R_I$ is a variously substituted aryl group;
$R_{II}$ is hydrogen or a ($C_1$–$C_4$)alkyl;
$R_{III}$ is a hydroxyl group, a ($C_1$–$C_6$)alkoxy or an amino group;
$R_{IV}$ is hydrogen, a halogen or a ($C_1$–$C_6$)alkyl;
$R_V$ is a variously substituted phenyl group; and
n is 0, 1, 2 or 3.

These compounds are active on the central nervous system and more particularly by interaction with the neurotensin receptor.

Furthermore, patent applications EP-A-576357 and EP-A-658546 describe pyrazole derivatives which have an affinity for the cannabinoid receptors. Also, patent application EP-A-656354 claims N-piperidino-5-(4-chlorophenyl)-1-(2,4-dichlorophenyl)-4-methylpyrazole-3-carboxamide, or SR 141716, and its pharmaceutically acceptable salts, which have a very good affinity for the central cannabinoid receptors.

Novel pyrazole derivatives have now been found which have a high affinity for the human $CB_2$ receptor and a specificity for said receptor, and which are potent immunomodulators.

In the present description, "high affinity for the human $CB_2$ receptor" denotes an affinity characterized by an affinity constant generally ranging from 100 nM to 0.1 nM, and "specific" denotes the compounds whose affinity constant for the $CB_2$ receptor is generally at least 10 times less than the affinity constant for the $CB_1$ receptor.

According to one of its features, the present invention relates to compounds of the formula

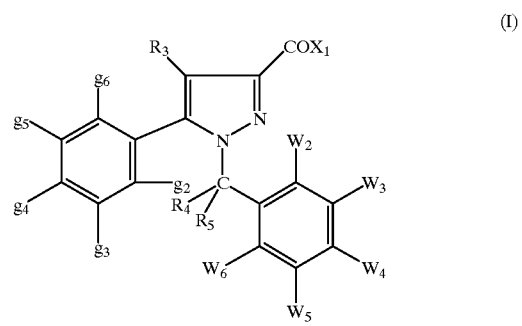

in which:
$X_1$ is a group —$NR_1R_2$ or a group —$OR_2$;
$g_2$, $g_3$, $g_4$, $g_5$, $g_6$ and $w_2$, $w_3$, $w_4$, $w_5$, $w_6$ are identical or different and are each independently hydrogen, a halogen atom, a $(C_1-C_4)$alkyl, a $(C_1-C_4)$alkoxy, a trifluoromethyl, a nitro or a $(C_1-C_4)$alkylthio, with the proviso that at least one of the substituents $g_2$, $g_3$, $g_4$, $g_5$, $g_6$ and at least one of the substituents $w_2$, $w_3$, $w_4$, $w_5$, $w_6$ are other than hydrogen;

$R_1$ is hydrogen or a $(C_1-C_4)$alkyl;

$R_2$ is a non-aromatic $(C_3-C_{15})$carbocyclic radical which is unsubstituted or monosubstituted or polysubstituted by a substituent selected from a halogen atom, a $(C_1-C_4)$alkyl and a $(C_1-C_4)$alkoxy;

$R_3$ is hydrogen or a group —$CH_2R_6$;

$R_4$ and $R_5$ are each independently a hydrogen, a $(C_1-C_4)$ alkyl or a trifluoromethyl;

or else $R_4$ is hydrogen and $R_5$ and $w_6$ together constitute an ethylene or trimethylene radical; and $R_6$ is hydrogen, or when the substituents $g_2$, $g_3$, $g_4$, $g_5$ and/or $g_6$ are other than a $(C_1-C_4)$alkyl, $R_6$ is hydrogen, a $(C_1-C_4)$alkyl, a fluorine, a hydroxyl, a $(C_1-C_5)$alkoxy, a $(C_1-C_5)$alkylthio, a hydroxy$(C_1-C_5)$alkoxy, a cyano, a $(C_1-C_5)$alkylsulfinyl or a $(C_1-C_5)$alkylsulfonyl;

and their optional salts.

If a compound of formula (I) according to the invention comprises one or more asymmetric carbon atoms, the different optical isomers and the racemates form part of the invention.

The optional salts of the compounds of formula (I) include the pharmaceutically acceptable acid addition salts such as the hydrochloride, hydrobromide, sulfate, hydrogensulfate, dihydrogenphosphate, methanesulfonate, methylsulfate, maleate, oxalate, fumarate, naphthalenesulfonate, glyconate, gluconate, citrate, isethionate, paratoluenesulfonate, mesitylenesulfonate or benzenesulfonate.

The non-aromatic $(C_3-C_{15})$carbocyclic radicals include saturated or unsaturated, fused, bridged or spiro monocyclic or polycyclic radicals, which may be terpenic. These radicals are optionally monosubstituted or polysubstituted by a group selected from $(C_1-C_4)$alkyl, $(C_1-C_4)$alkoxy and halogen groups, it being understood that in the case of terpenes or terpenic radicals, for example bornyl, menthyl or menthenyl, the alkyl groups of the terpene are not considered as substituents.

The monocyclic radicals include cycloalkyls, for example cyclopropyl, cyclopentyl, cyclohexyl, cycloheptyl, cyclooctyl and cyclodecyl, which are unsubstituted or monosubstituted or polysubstituted by a $(C_1-C_4)$alkyl group, a $(C_1-C_4)$alkoxy group or a halogen, such as 2-methylcyclohex-1-yl, 2,6-dimethylcyclohex-1-yl or 2,2,6,6-tetramethylcyclohex-1-yl for example.

The fused, bridged or spiro dicyclic or tricyclic radicals, which may be terpenic, include for example bicyclo[2.2.1] heptyl or norbornyl radicals, bornyl, isobornyl, noradamantyl, adamantyl, bicyclo[3.2.1]octyl, bicyclo [2.2.2]octyl, tricyclo[5.2.1.0$^{2,6}$]decyl, spiro[5.5]undecyl, bicyclo[2.2.2]oct-2-en-5-yl and tricyclo[2.2.1.0$^{2,6}$]hept-3-yl, said radicals being unsubstituted or monosubstituted or polysubstituted by a $(C_1-C_4)$alkyl, a halogen or a $(C_1-C_4)$ alkoxy, examples being 1,3,3-trimethylbicyclo[2.2.1]hept-2-yl or fenchyl.

In the present description, the alkyl groups or the alkoxy groups are linear or branched. Halogen atom is understood as meaning a chlorine, bromine, fluorine or iodine atom.

According to the present invention, the compounds of formula (I) in which:

$X_1$ is a group —$NR_1R_2$;

$g_2$, $g_3$, $g_4$, $g_5$, $g_6$ and $w_2$, $w_3$, $w_4$, $w_5$, $w_6$ are identical or different and are each independently hydrogen, a halogen atom, a $(C_1-C_4)$alkyl, a $(C_1-C_4)$alkoxy, a trifluoromethyl, a nitro or a $(C_1-C_4)$alkylthio, with the proviso that at least one of the substituents $g_2$, $g_3$, $g_4$, $g_5$, $g_6$ and at least one of the substituents $w_2$, $w_3$, $w_4$, $w_5$, $w_6$ are other than hydrogen;

$R_1$ is hydrogen or a $(C_1-C_4)$alkyl;

$R_2$ is a non-aromatic $(C_3-C_{15})$carbocyclic radical which is unsubstituted or monosubstituted or polysubstituted by a substituent selected from a halogen atom, a $(C_1-C_4)$alkyl and a $(C_1-C_4)$alkoxy;

$R_3$ is hydrogen or a group —$CH_2R_6$;

$R_4$ and $R_5$ are each independently a hydrogen, a $(C_1-C_4)$ alkyl or a trifluoromethyl; and $R_6$ is hydrogen, a methyl group or an ethyl group;

and their optional salts, are preferred.

Among the compounds of formula (I) in which $X_1$ is a group —$NR_1R_2$, those where $R_1$ is hydrogen are preferred.

Among the compounds of formula (I) in which $X_1$ is a group —$NR_1R_2$ or a group —$OR_2$, those where $R_2$ is a 1,3,3-trimethylbicyclo[2.2.1]hept-2-yl radical or a bicyclo [3.2.1]oct-3-yl radical are preferred.

Among the compounds of formula (I), those where $R_3$ is hydrogen or a group —$CH_2R_6$, $R_6$ being hydrogen, are preferred.

Among the compounds of formula (I), those where either $R_4$ and $R_5$ are each hydrogen or $R_4$ is hydrogen and $R_5$ is a $(C_1-C_4)$alkyl, are preferred.

Among the compounds of formula (I), those where $g_2$, $g_5$ and $g_6$ are hydrogen and $g_3$ and $g_4$ are as defined above for the compounds of formula (I), are preferred.

Among the compounds of formula (I), those where $w_5$ and $w_6$ are hydrogen, $w_4$ is a halogen atom, a $(C_1-C_4)$alkyl, a $(C_1-C_4)$alkoxy, a trifluoromethyl or a $(C_1-C_4)$alkylthio and either $w_2$ and $w_3$ are each hydrogen or one is hydrogen and the other is a halogen atom, a $(C_1-C_4)$alkyl or a trifluoromethyl, are preferred.

A preferred group of compounds according to the present invention is the group of compounds of the formula

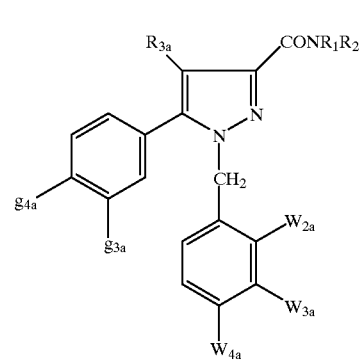

(Ia)

in which:

$R_1$ and $R_2$ are as defined for the compounds of formula (I);

$R_{3a}$ is hydrogen or a group —$CH_2R_{6a}$;

$R_{6a}$ is hydrogen, or when the substituents $g_{3a}$ and/or $g_{4a}$ are other than a $(C_1-C_4)$alkyl, $R_6$ is hydrogen, a methyl group or an ethyl group;

$g_{3a}$ is hydrogen, a halogen atom, a $(C_1-C_4)$alkyl or a trifluoromethyl;

$g_{4a}$ is a halogen atom, a $(C_1-C_4)$alkyl or a trifluoromethyl;

$w_{4a}$ is a halogen atom, a $(C_1-C_4)$alkyl or a trifluoromethyl; and $w_{2a}$ and $w_{3a}$ are each hydrogen or one is hydrogen and the other is a halogen atom, a $(C_1-C_4)$alkyl or a trifluoromethyl;

and their optional salts.

Among these compounds, those of the formula

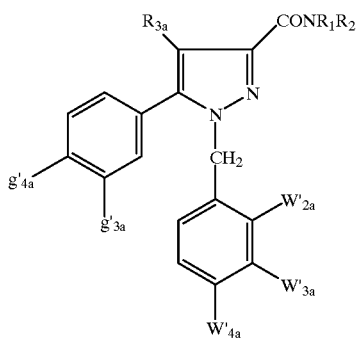

(I'a)

in which:
R$_1$ and R$_2$ are as defined for the compounds of formula (I);
R$_{3a}$ is as defined for the compounds of formula (Ia);
g'$_{3a}$ is hydrogen, a chlorine atom, a fluorine atom, a methyl group or a trifluoromethyl;
g'$_{4a}$ is a chlorine atom, a fluorine atom, a methyl group or a trifluoromethyl;
w'$_{4a}$ is a chlorine atom, a fluorine atom, a methyl group or a trifluoromethyl;
w'$_{2a}$ and w'$_{3a}$ are each hydrogen or one is hydrogen and the other is a chlorine atom, a fluorine atom, a methyl group or a trifluoromethyl;
and their optional salts, are particularly preferred.
The more particularly preferred compounds are those of formula (I'a) in which:
R$_1$ is hydrogen;
R$_2$ is a 1,3,3-trimethylbicyclo[2.2.1]hept-2-yl radical or a bicyclo[3.2.1]oct-3-yl radical;
R$_{3a}$ is as defined for the compounds of formula (Ia); and
w'$_{2a}$, w'$_{3a}$, w'$_{4a}$, g'$_{3a}$ and g'$_{4a}$ are as defined for the compounds of formula (I'a);
and their optional salts.
Especially preferred are the compounds of formula (I'a) in which:
g'$_{3a}$ is hydrogen, a chlorine atom, a fluorine atom or a methyl group;
g'$_{4a}$ is a chlorine atom, a fluorine atom or a methyl group;
w'$_{4a}$ is a chlorine atom, a fluorine atom or a methyl group;
w'$_{2a}$ and w'$_{3a}$ are each hydrogen or one is hydrogen and the other is a chlorine atom, a fluorine atom or a methyl group; and
R$_1$, R$_2$ an R$_{3a}$ are as defined for the compounds of formula (I'a);
and their optional salts.
Another preferred group of compounds according to the invention is the group of compounds of the formula

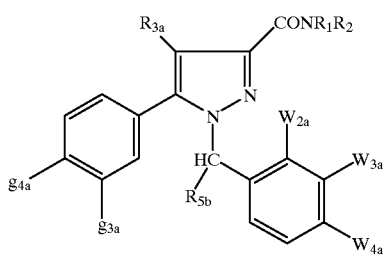

(Ib)

in which:
R$_1$ and R$_2$ are as defined for the compounds of formula (I);

R$_{3a}$, w$_{2a}$, w$_{3a}$, w$_{4a}$, g$_{3a}$ and g$_{4a}$ are as defined for the compounds of formula (Ia); and
R$_{5b}$ is a (C$_1$–C$_4$)alkyl;
and their optional salts.
Among these compounds, those of the formula

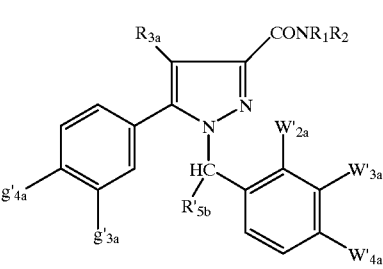

(I'b)

in which:
R$_1$ and R$_2$ are as defined for the compounds of formula (I);
R$_{3a}$ is as defined for the compounds of formula (Ia);
w'$_{2a}$, w'$_{3a}$, w'$_{4a}$, g'$_{3a}$ and g'$_{4a}$ are as defined for the compounds of formula (I'a); and
R'$_{5b}$ is a methyl group;
and their optional salts, are particularly preferred.
The more particularly preferred compounds are those of formula (I'b) in which:
R$_1$ is hydrogen;
R$_2$ is a 1,3,3-trimethylbicyclo[2.2.1]hept-2-yl radical or a bicyclo[3.2.1]oct-3-yl radical;
R$_{3a}$ is as defined for the compounds of formula (Ia);
R'$_{5b}$ is a methyl group; and
w'$_{2a}$, w'$_{3a}$, w'$_{4a}$, g'$_{3a}$ and g'$_{4a}$ are as defined for the compounds of formula (I'a);
and their optional salts.
Especially preferred are the compounds of formula (I'b) in which:
g'$_{3a}$ is hydrogen, a chlorine atom, a fluorine atom or a methyl group;
g'$_{4a}$ is a chlorine atom, a fluorine atom or a methyl group;
w'$_{4a}$ is a chlorine atom, a fluorine atom or a methyl group;
w'$_{2a}$ and w'$_{3a}$ are each hydrogen or one is hydrogen and the other is a chlorine atom, a fluorine atom or a methyl group; and
R$_1$, R$_2$, R$_{3a}$ and R'$_{5b}$ are as defined for the compounds of formula (I'b);
and their optional salts.
Another preferred group of compounds according to the invention is the group of compounds of the formula:

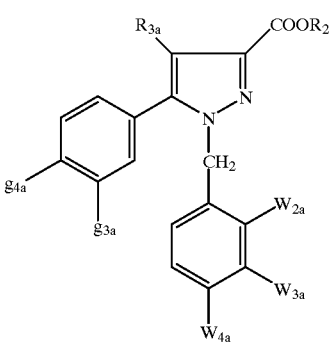

(Ic)

in which:
R$_2$ is as defined for the compounds of formula (I); and $R_{3a}$, $w_{2a}$, $w_{3a}$, $w_{4a}$, $g_{3a}$ and $g_{4a}$ are as defined for the compounds of formula (Ia);

and their optional salts.

According to another of its features, the present invention relates to a process for the preparation of the compounds of formula (I) and their salts, wherein:

1) a functional derivative of the pyrazole-3-carboxylic acid of the formula

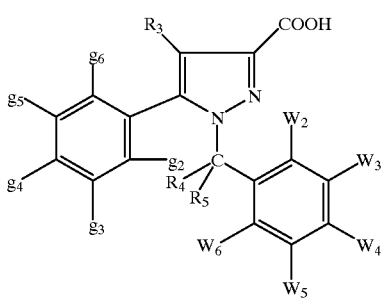

(II)

in which $w_2$, $w_3$, $w_4$, $w_5$, $w_6$, $g_2$, $g_3$, $g_4$, $g_5$, $g_6$, $R_3$, $R_4$ and $R_5$ are as defined for the compounds of formula (I), is treated with a compound of the formula $$H-X_1 \qquad (XXIV)$$

in which $X_1$ is as defined for the compounds of formula (I); and 2) the resulting compound is optionally converted to one of its salts.

One of the obtention process according to the invention (process A) is suitable for the preparation of the compounds of formula (I) in which $X_1$ is a group —$NR_1R_2$.

This process is characterized is that:

1) a functional derivative of the pyrazole-3-carboxylic acid of formula (II) as defined above, is treated with an amine of the formula:

$$HNR_1R_2 \qquad (III)$$

in which $R_1$ and $R_2$ are as defined for the compounds of formula (I); and 2) the resulting compound is optionally converted to one of its salts.

As the functional derivative of the acid (II) it is possible to use the acid chloride, the anhydride, a mixed anhydride, a $C_1$–$C_4$-alkyl ester in which the alkyl is linear or branched, an activated ester, for example the p-nitrophenyl ester, or the free acid appropriately activated with for example N,N-dicyclohexylcarbodiimide or benzotriazol-1-yloxytris (dimethylamino)phosphonium hexafluorophosphate (BOP).

Thus, in the process A according to the invention, the chloride of the pyrazole-3-carboxylic acid, obtained by reacting thionyl chloride with the acid of formula (II), can be reacted with an amine $HNR_1R_2$, in an inert solvent such as a chlorinated solvent (for example dichloromethane, dichloroethane, chloroform), an ether (for example tetrahydrofuran, dioxane) or an amide (for example N,N-dimethylformamide), under an inert atmosphere, at a temperature between 0° C. and room temperature, in the presence of a tertiary amine such as triethylamine, N-methylmorpholine or pyridine.

One variant of the procedure of process A consists in preparing a mixed anhydride of the acid of formula (II) by reacting ethyl chloroformate with the acid of formula (II), in the presence of a base such as triethylamine, and reacting said mixed anhydride with an amine $HNR_1R_2$, in a solvent such as dichloromethane, under an inert atmosphere, at room temperature, in the presence of a base such as triethylamine.

Another obtention process according to the invention (process B) is suitable for the preparation of the compounds of formula (I) in which $X_1$ is a group —$OR_2$.

This process is characterized in that:

1) a functional derivative of the pyrazole-3-carboxylic acid of formula (II) as defined above, is treated with an alcohol of the formula:

$$HO-R_2 \qquad (XIV)$$

in which $R_2$ is as defined for the compounds of formula (I); and 2) the resulting compound is optionally converted to one of its salts.

As the functional derivative of the acid (II) it is possible to use the acid chloride, the anhydride, a mixed anhydride, or the free acid appropriately activated with for example N,N-dicyclohexylcarbodiimide or benzotriazol-1-yloxytris (dimethylamino)phosphonium hexafluorophosphate (BOP).

Thus, in the process B according to the invention, the chloride of the pyrazole-3-carboxylic acid, obtained by reacting thionyl chloride with the acid of formula (II), can be reacted with an alcohol $HOR_2$, in an inert solvent such as a chlorinated solvent (for example dichloromethane, dichloroethane, chloroform), an ether (for example tetrahydrofuran, dioxane) or an amide (for example N,N-dimethylformamide), under an inert atmosphere, at a temperature between 0° C. and room temperature, in the presence of a tertiary amine such as triethylamine, N-methylmorpholine or pyridine, or in pyridine at room temperature in the presence of 4-dimethylaminopyridine.

One variant of the procedure of process B consists in preparing a mixed anhydride of the acid of formula (II) by reacting ethyl chloroformate with the acid of formula (II), in the presence of a base such as triethylamine, and reacting said mixed anhydride with an alcohol $HOR_2$, in a solvent such as dichloromethane, under an inert atmosphere, at room temperature, in the presence of a base such as triethylamine.

During any one of the preparation steps of the compounds of formula (I) and more particularly in the preparation of the intermediate compound of formula (II), it can be necessary and/or desirable to protect reactive or sensitive functional groups present on any one of the concerned molecules, such as amine, hydroxyl or carboxy groups. This protection can be carried out using conventional protective groups such as those described in Protective Groups in Organic Chemistry, J. F. W. McOmie, Plunum Press publisher, 1973 and in Protective Groups in Organic Synthesis, T. W. Greene and P. G. M Wutts, John Wiley & Sons publishers, 1991. Removal of the protective groups can be carried out in a further appropriate step using the methods known to those skilled in the art and which do not modify the remainder of the concerned molecule.

The resulting compound of formula (I) is isolated by the conventional techniques.

Depending on the nature of the substituents, the compound of formula (I) can optionally be salified. Salification is effected by treatment with the chosen acid in an organic solvent. Treatment of the free base, dissolved for example in an ether such as diethyl ether, in an alcohol such as propan-2-ol, in acetone or in dichloromethane, with a solution of the chosen acid in the same solvent gives the corresponding salt, which is isolated by the conventional techniques.

The hydrochloride, hydrobromide, sulfate, hydrogensulfate, dihydrogenphosphate, methanesulfonate, oxalate, maleate, fumarate, naphthalenesulfonate and benzenesulfonate, for example, are prepared in this way.

The compounds of formula (II) are prepared according to various procedures.
The compounds of formula (II) in which $R_3=R'_3$ and is hydrogen or a group —$CH_2R_6$ in which $R_6$ is hydrogen or a ($C_1$–$C_4$)alkyl group are prepared according to SCHEME 1 below:
SCHEME 1
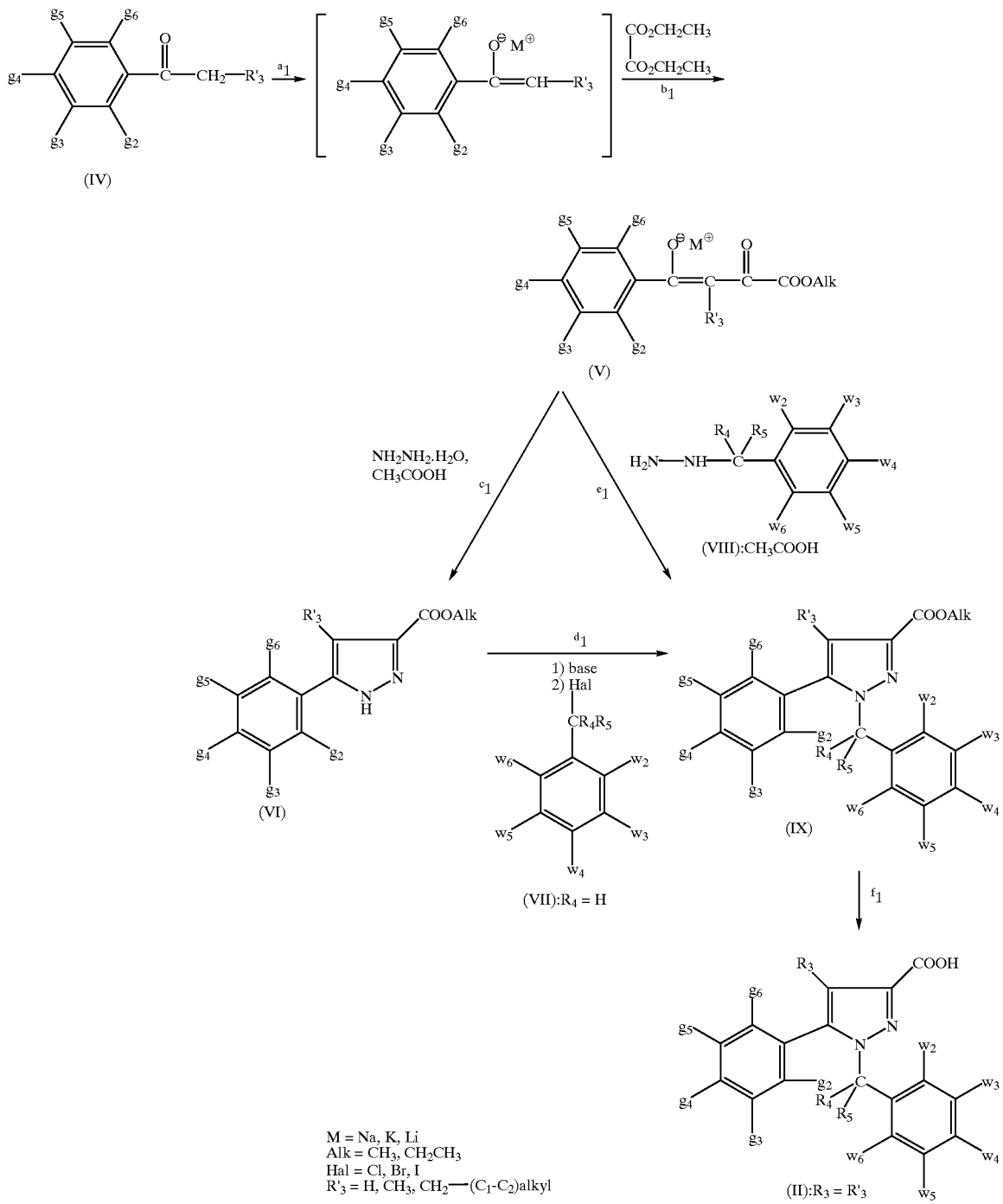

The first step, $a_1$, consists in preparing an alkali metal salt of the acetophenone derivative of formula (IV), in which $R'_3$ is hydrogen or a group —$CH_2R_6$ in which $R_6$ is hydrogen or a ($C_1$–$C_4$)alkyl and $g_2$, $g_3$, $g_4$, $g_5$ and $g_6$ are as defined for (I), and then adding an equimolar amount of diethyl oxalate (step $b_1$) to give the ketoester salt of formula (V).

In the particular case where $R'_3$=H, the alkali metal will preferably be sodium (M=Na) and the ketoester salt (V, Alk=$CH_3$) will be obtained by the process described in Bull. Soc. Chim. Fr., 1947, 14, 1098, using sodium methylate in methanol to perform step $a_1$. Step $a_1$ can also be carried out by reacting potassium tert-butylate in ethanol with the derivative of formula (IV) and then adding diethyl oxalate as described above. The reaction is carried out at the reflux temperature of the solvent and gives the compound of formula (V) in which M=K and Alk=$CH_2CH_3$.

In the particular case where $R'_3$=$CH_3$, the alkali metal will preferably be lithium (M=Li) and the ketoester salt (V, Alk=$CH_2CH_3$) will be obtained by the process described in J. Heterocyclic Chem., 1989, 26, 1389–1392, using the lithium salt of hexamethyldisilazane in an inert solvent, such as diethyl ether or cyclohexane, to perform step $a_1$.

In step $c_1$ the compound of formula (V) prepared in this way and excess hydrazine (hydrazine monohydrate or aqueous hydrazine solution) are refluxed in acetic acid. Precipitation in iced water gives the pyrazole-3-carboxylates of formula (VI).

In step $d_1$ the compound of formula (VI) obtained in this way is treated with a strong base, such as sodium hydride or sodium amide in a solvent, to give an anion; this is reacted with a compound of formula (VII), in which Hal is a halogen, preferably chlorine, bromine or iodine, $R_4$ is hydrogen and $w_2$, $w_3$, $w_4$, $w_5$, $w_6$ and $R_5$ are as defined for the compounds of formula (I), to give the compound of formula (IX). The reaction is preferably carried out in toluene at a temperature between room temperature and the reflux temperature of the solvent so as to obtain the expected compound of formula (IX) in majority. When the reaction is carried out in N,N-dimethylformamide at a temperature between 0° C. and room temperature, it is observed that the position isomer of the formula:

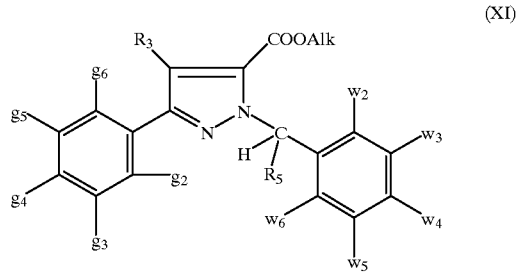

is formed in majority.

Alternatively, in step $e_1$ the compound of formula (V) and an excess of the hydrazine derivative of formula (VIII), in which $R_4$, $R_5$, $w_2$, $w_3$, $w_4$, $w_5$ and $w_6$ are as defined for the compounds of formula (I), are refluxed in acetic acid; precipitation in iced water gives the compounds of formula (IX).

In step $f_1$ hydrolysis of the compounds of formula (IX) in an alkaline medium, followed by acidification, gives the expected compounds of formula (II). The hydrolysis is carried out using for example an alkali metal hydroxide such as potassium hydroxide, sodium hydroxide or lithium hydroxide, in an inert solvent such as water, methanol, ethanol, dioxane or a mixture of these solvents, at a temperature between 0° C. and the reflux temperature of the solvent.

The compounds of formula (IX) in which $R_4$ is hydrogen are preferably prepared using steps $c_1$ and then $d_1$ described above.

The compounds of formula (IX) in which $R_4$ and $R_5$ are other than hydrogen are preferably prepared using step $e_1$ described above.

The compounds of formula (IX) in which $R'_3$=$CH_2$-($C_1$–$C_4$)alkyl are preferably prepared either from the compounds of formula (IX) themselves, if $R_4$ and $R_5$ are other than hydrogen, or from the compounds of formula (VI), if $R_4$=H, according to SCHEME 2 below:

SCHEME 2

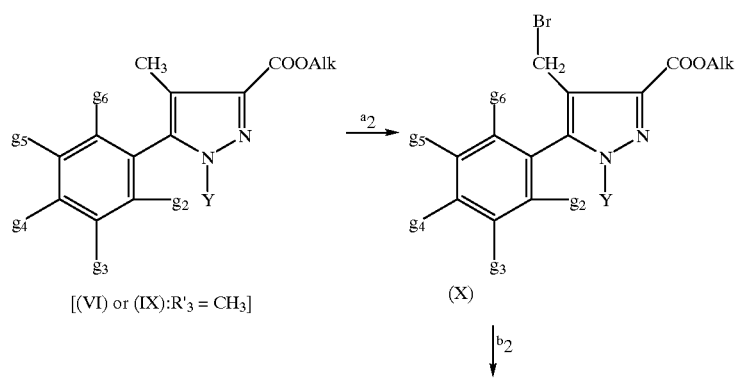

-continued

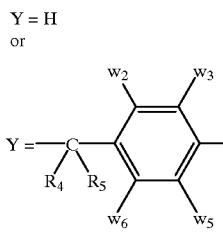

with $R_4$ and $R_5 \neq H$

Alk = $CH_3$, $CH_2CH_3$
Alk' = $(C_1-C_4)$alkyl

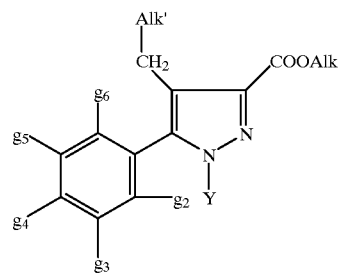

[(VI) or (IX): $R'_3$ = $CH_2$—$(C_1-C_4)$alkyl]

Step $a_2$ consists in preparing a 4-bromomethylpyrazole-3-carboxylate of formula (X) by reacting N-bromosuccinimide with a compound of formula (VI) or (IX) in which $R'_3$ is a methyl group. The reaction is carried out in an inert solvent such as carbon tetrachloride, in the presence of dibenzoyl peroxide, at the reflux temperature of the solvent.

When a compound of formula (VI) is used, bromination in step $a_2$ is preferably carried out with a compound whose nitrogen atom of the pyrazole is protected (Y=N-protective group). Conventional N-protective groups well known to those skilled in the art, such as tert-butoxycarbonyl, are used as N-protective group.

Step $b_2$ consists in preparing a compound of formula (VI) or (IX) in which $R'_3$ is a $CH_2$-$(C_1-C_4)$alkyl group by reaction with an organocuprate $(Alk')_2CuLi$, in which Alk' is a $(C_1-C_4)$alkyl group. The reaction is carried out by the process described in patent application EP-A-0658546.

When a compound of formula (VI), whose nitrogen atom of the pyrazole is protected, is optionally used, the N-protective group is removed after step $b_2$ according to the methods known to those skilled in the art.

The compounds of formula (II) in which $R_4$ is hydrogen and $R_3=R''_3$ and is a group —$CH_2R_6$ in which $R_6$ is other than hydrogen or than a $(C_1-C_4)$alkyl are prepared according to SCHEME 3 below:

SCHEME 3

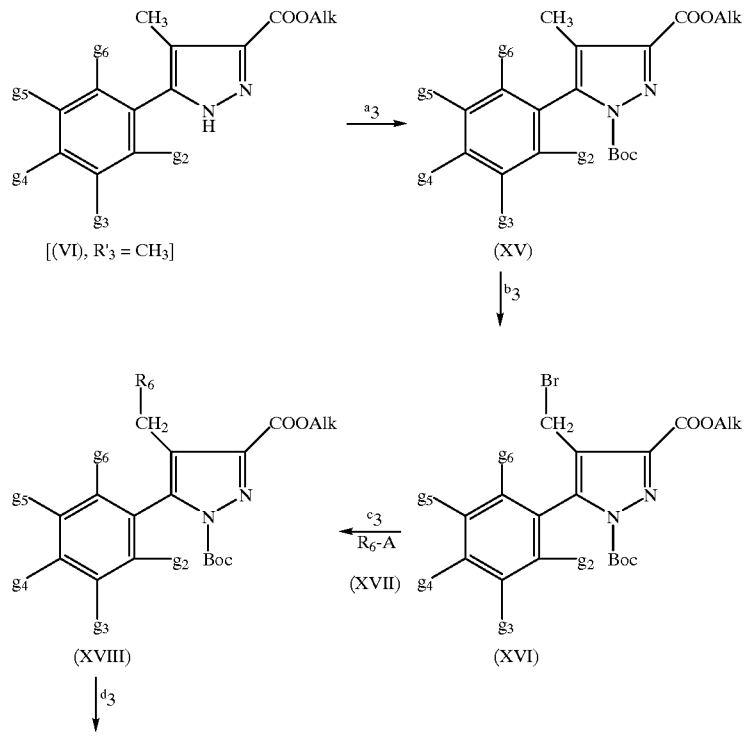

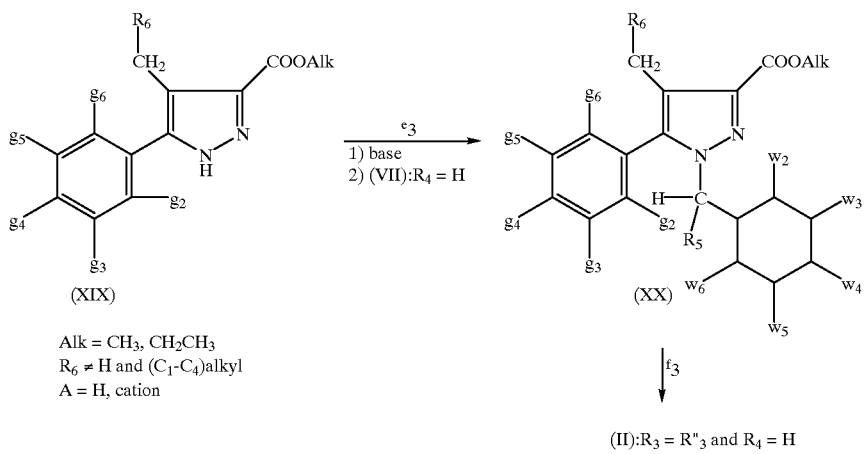

Alk = CH₃, CH₂CH₃
R₆ ≠ H and (C₁-C₄)alkyl
A = H, cation (II):R₃ = R"₃ and R₄ = H In step a₃ the nitrogen atom of the compound of formula (VI) (R'₃=CH₃) is protected by a N-protective group such as tert-butoxycarbonyl (Boc) according to the methods known to those skilled in the art.

Step b₃ consists in preparing a 4-bromomethylpyrazole-3-carboxylate of formula (XVI) according to the method previously described in step a₂ of SCHEME 2.

In step c₃ the compound of formula (XVI) is treated with a compound of formula R₆—A (XVII) in which R₆, as defined for (I), is other than hydrogen or than a (C₁-C₄)alkyl and A is hydrogen or a cation such as an alkali or alkaline earth metal cation or a quaternary ammonium group such as tetraethylammonium.

A compound of formula (XVIII) in which R₆ is a (C₁-C₅) alkoxy or a hydroxy(C₁-C₅)alkoxy is prepared using a (C₁-C₅)-alcohol or -dialcohol as reagent of formula (XVII) in the presence of a non nucleophilic base such as a metal hydride, for example sodium or potassium hydride.

A mixture of esters, which is saponified in step f₃ to give the acid of formula (II), can be obtained in step c₃ of the process depending on the values of R₆.

A compound of formula (XVIII) in which R₆ is a (C₁-C₅) alkylthio is prepared using a (C₁-C₅)thioalcohol as reagent of formula (XVII) in the presence of a non nucleophilic base such as a metal hydride, for example sodium or potassium hydride.

If need be, the ester of formula (XVIII) obtained in step c₃, in which R₆ is a (C₁-C₅)alkylthio, can be converted by the action of an oxidizing agent such as hydrogen peroxide or meta-chloroperbenzoic acid to give a compound of formula (XVIII) in which R₆ is a (C₁-C₅)alkylsulfinyl or a (C₁-C₅)alkylsulfonyl.

A compound of formula (XVIII) in which R₆ is a cyano can be prepared using a quaternary ammonium cyanide, for example tetraethylammonium cyanide or a metal cyanide such as sodium cyanide, as reagent of formula (XVII); in the latter case the nucleophilic substitution reaction of step c₃ is carried out in the presence of a phase transfer catalyst.

A compound of formula (XVIII) in which R₆ is fluorine can be prepared using a fluorination agent as reagent of formula (XVII); a metal fluoride, for example potassium fluoride, used in the presence of a complexing agent such as Kryptofix®, may be cited as fluorination agent.

A compound of formula (XVIII) in which R₆=OH is prepared using an alkali or alkaline earth metal hydroxide such as sodium or potassium hydroxide as reagent (XVII).

In step d₃, the N-protective group is removed according to the methods known to those skilled in the art.

In step e₃ the resulting compound (XIX) is treated with a strong base such as sodium hydride or sodium amide in a solvent to give an anion; this is reacted with a compound of formula (VII) in which Hal is a halogen, preferably chlorine, bromine or iodine, R₄ is hydrogen and w₂, w₃, w₄, w₅, w₆ and R₅ are as defined for the compounds of formula (I) to give the compound of formula (XX). The reaction is preferably carried out in toluene at a temperature between room temperature and the reflux temperature of the solvent so as to obtain the expected compound of formula (XX) in majority. When the reaction is carried out in N,N-dimethylformamide at a temperature between 0° C. and room temperature, it is observed that the position isomer of the formula:

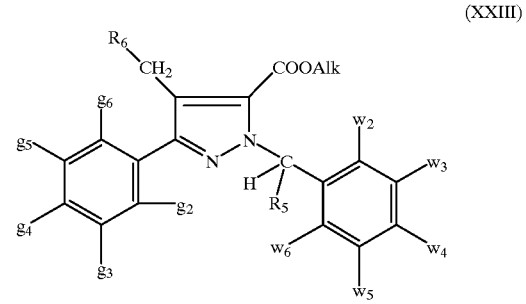

(XXIII)

is formed in majority.

In step f₃ the expected compounds of formula (II) are obtained by hydrolysis of the compounds of formula (XX) in an alkaline medium followed by acidification. The hydrolysis is carried out using for example an alkali metal hydroxide such as potassium hydroxide, sodium hydroxide or lithium hydroxide in an inert solvent such as water, methanol, ethanol, dioxane or a mixture of these solvents, at a temperature between 0° C. and the reflux temperature of the solvent.

The compounds of formula (II) in which R₃=R"₃ and is a group —CH₂R₆ in which R₆ is other than hydrogen or than a (C₁-C₄)alkyl and R₄ and R₅ are both different from hydrogen are prepared according to SCHEME 4 below in which Alk is a methyl group or an ethyl group.

SCHEME 4

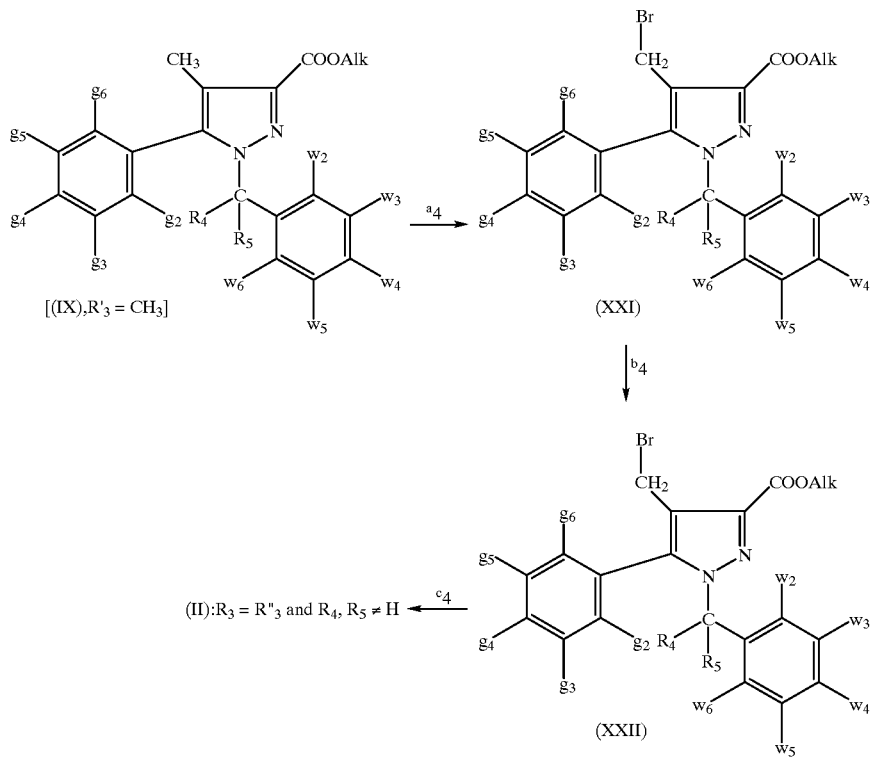

Step $a_4$ consists in preparing a 4-bromomethylpyrazole-3-carboxylate of formula (XXI) according to the method previously described in step $a_2$ of SCHEME 2.

In step $b_4$ the compound of formula (XXI) is treated with a compound of formula $R_6$—A (XVII) as previously defined according to the procedures described in step $c_3$ of SCHEME 3.

In step $c_4$ the expected compounds of formula (II) are obtained by hydrolysis of the compounds of formula (XXII) in an alkaline medium followed by acidification. The hydrolysis is carried out according to the methods described in step $f_1$ of SCHEME 1.

In step $d_1$ of SCHEME 1 or in step $e_3$ of SCHEME 3, the reaction of the compound of formula (VI) or of the compound of formula (XIX) with the halogenated derivative of formula (VII) can give a mixture of variable proportions of the compound of formula (IX) or of the compound of formula (XX) and their respective isomers of the formulae

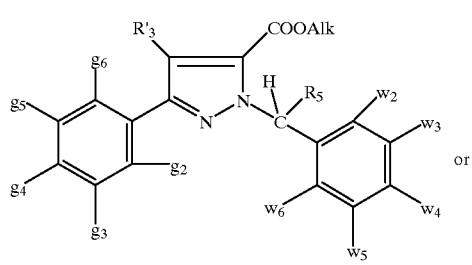

(XI)

-continued

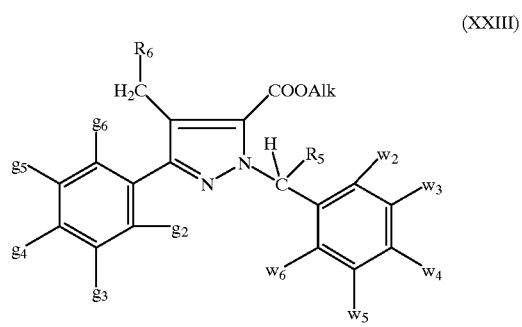

(XXIII)

The two isomers (IX) and (XI) or the two isomers (XX) and (XXIII) can be separated by the conventional methods of chromatography on silica gel. The two isomers (IX) and (XI) or (XX) and (XXIII) are characterized by their NMR spectra, especially by studying the Overhauser effect (NOE).

Step $f_1$ or step $f_3$ of the process, as described in SCHEME 1 or SCHEME 3, can also be carried out on the mixture of isomers to give a mixture of the acid of formula (II) and its isomer of the formula

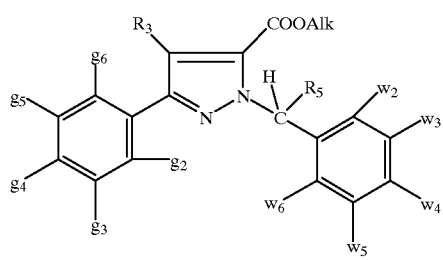
(XII)

The process according to the invention, described above, is then applied to the mixture of the two isomers (II) and (XII) to give a mixture of a compound of formula (I) in which $R_4$=H and its isomer of the formula

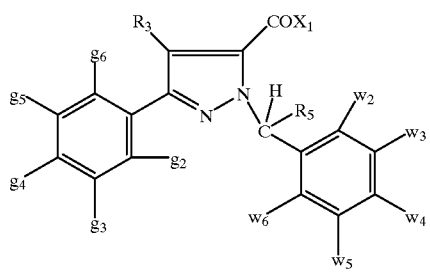
(XIII)

The two isomers are then separated by the conventional methods, such as for example chromatography on silica gel or crystallization, ultimately giving the compound of formula (I) according to the invention.

According to another of its features, the present invention relates to compounds of the formula:

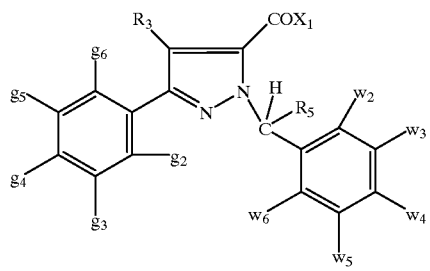
(XIII)

in which:

$X_1$, $g_2$, $g_3$, $g_4$, $g_5$, $g_6$, $w_2$, $w_3$, $w_4$, $w_5$, $w_6$, $R_3$ and $R_5$ are as defined for the compounds of formula (I), and their optional salts;

said compounds being sub-products of the process for the preparation of the compounds of formula (I).

According to another of its features, the present invention relates to a process for the preparation of the intermediate compounds of formula (II) and the compounds of formula (XII), which are useful for the preparation of the compounds of formula (I) in which $R_4$=H and the compounds of formula (XIII), which comprises the steps of:

1) treating a compound of the formula:

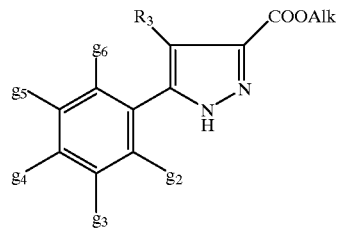
(XXV)

in which $g_2$, $g_3$, $g_4$, $g_5$, $g_6$ and $R_3$ are as defined for the compounds of formula (I) and Alk is a methyl or ethyl group, with a strong base in a solvent, and then reacting the resulting anion with a compound of the formula:

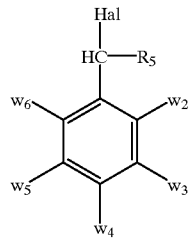
(VII)

in which $w_2$, $w_3$, $w_4$, $w_5$, $w_6$ and $R_5$ are as defined for the compounds of formula (I) and Hal is a halogen atom, to give:
either a compound of the formula:

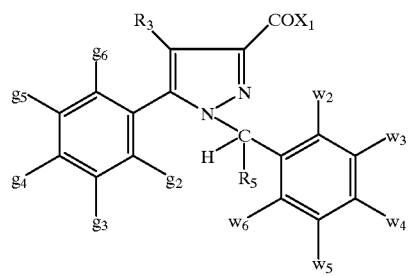
(XXVI)

when the reaction is carried out in toluene at a temperature between room temperature and the reflux temperature of the solvent;
or a compound of the formula:

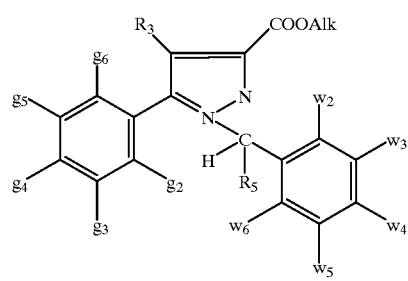
(XXVII)

when the reaction is carried out in N,N-dimethylformamide at a temperature between 0° C. and room temperature; and 2) hydrolyzing either the compound of formula (XXVI) or the compound of formula (XXVII) in an alkaline medium to give respectively:

either the compound of the formula:

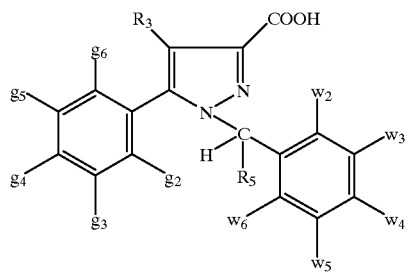

(II:R$_4$ = H)

or the compound of the formula:

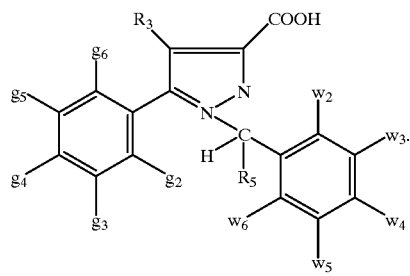

(XII)

According to another of its features, the present invention relates to a process for the preparation of the compounds of formula (XIII) and their salts, which comprises the steps of:

1) treating a functional derivative of the acid of the formula:

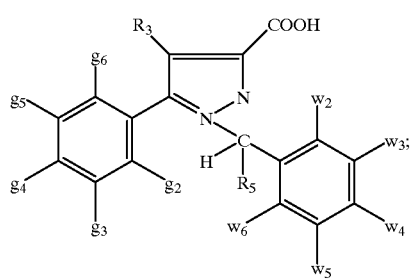

(XII)

in which g$_2$, g$_3$, g$_4$, g$_5$, g$_6$, w$_2$, w$_3$, w$_4$, w$_5$, w$_6$, R$_3$ and R$_5$ are as defined for the compounds of formula (I), with a compound of the formula:

HX$_1$           (XXIV)

in which X$_1$ is as defined for the compounds (I) to give the compound of the formula:

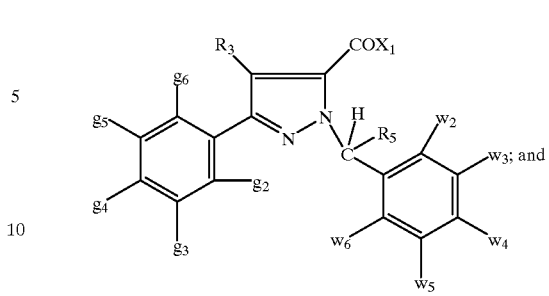

(XIII)

2/ optionally converting the resulting compound to one of its salts.

The benzyl halides of formula (VII) are known or are prepared by known methods.

In general, the compounds of formula (VII) in which Hal is a bromine atom can be prepared by reacting N-bromosuccinimide with the corresponding methylbenzene derivatives in the presence of dibenzoyl peroxide. It is also possible to prepare a benzyl bromide from a corresponding benzyl alcohol by reaction with aqueous hydrobromic acid solution or a solution of hydrobromic acid in acetic acid. Another possibility is to react phosphorus tribromide with a corresponding benzyl alcohol in order to prepare a compound of formula (VII) in which Hal is a bromine atom.

The compounds of formula (VII) in which Hal is an iodine atom can be prepared by reacting sodium iodide with a compound of formula (VII) in which Hal is a chlorine atom in a solvent such as acetone or butan-2-one.

The compounds of formula (VII) in which Hal is a chlorine atom can be prepared by reacting thionyl chloride with a corresponding benzyl alcohol.

In particular, the compounds of formula (VII) in which R$_5$ is a trifluoromethyl and Hal is a chlorine atom can be prepared by the method described in J. Fluorine Chem., 1986, 32 (4), 361–366.

The compounds of formula (VII) in which R$_5$ is a trifluoromethyl can also be prepared from the corresponding α-(trifluoromethyl)benzyl alcohols by the methods described above. The α-(trifluoromethyl)benzyl alcohols can be prepared according to Tetrahedron, 1989, 45 (5), 1423, or J. Org. Chem., 1991, 56 (1), 2.

The compounds of formula (VIII) are known or are prepared by known methods such as those described in J. Org. Chem., 1988, 53, 1768–1774, or J. Am. Chem. Soc., 1958, 80, 6562–6568.

The amines of the formula HNR$_1$R$_2$ are either commercially available, or described in the literature, or prepared by known methods according to the Preparations described below:

endo- and exo-bicyclo[3.2.1]octan-2-ylamine prepared according to H. Maskill et al., J. Chem. Soc. Perkin II, 1984, 119;

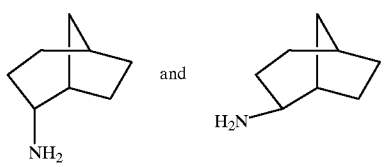

bicyclo[2.2.2]octan-2-ylamine prepared according to R. Seka et al., Ber., 1942, 1379;

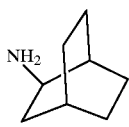

endo- and exo-bicyclo[3.2.1]octan-3-ylamine prepared according to H. Maskill et al., J. Chem. Soc. Perkin Trans. II, 1984, 1369;

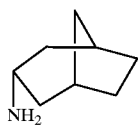 and 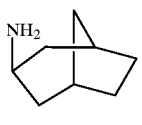

endo-tricyclo[5.2.1.0$^{2,6}$]decan-8-ylamine prepared according to G. Buchbauer et al., Arch. Pharm., 1990, 323, 367;

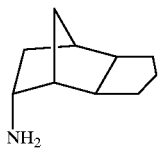

endo- and exo-, 1R- and 1S-1,3,3-trimethylbicyclo[2.2.1]heptan-2-ylamine prepared according to Ingersoll et al., J. Am. Chem. Soc., 1951, 73, 3360, or J. A. Suchocki et al., J. Med. Chem., 1991, 34, 1003–1010;

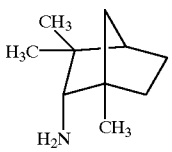 and 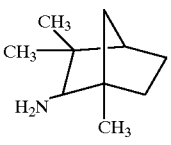

3-methylcyclohexylamine prepared according to Smith et al., J. Org. Chem., 1952, 17, 294;

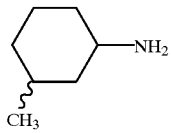

2,6-dimethylcyclohexylamine prepared according to Cornubert et al, Bull. Soc. Chim. Fr., 1945, 12, 367;

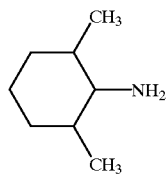

2-methoxycyclohexylamine prepared according to Noyce et al., J. Am. Chem. Soc., 1954, 76, 768;

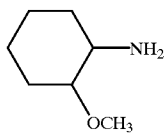

4-ethylcyclohexylamine prepared according to A. Shirahata et al., Biochem. Pharmacol., 1991, 41, 205;

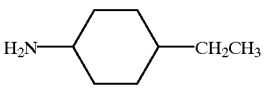

bicyclo[2.2.2]oct-2-en-5-amine prepared according to H. L. Goering et al., J. Am. Chem. Soc., 1961, 83, 1391;

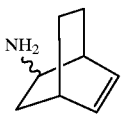

N-ethyl-1-adamantylamine prepared according to V. L. Narayanan et al., J. Med. Chem., 1972, 15, 443;

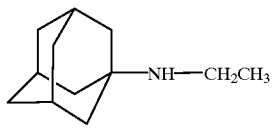

tricyclo[2.2.1.0$^{2,6}$]heptan-3-ylamine prepared according to G. Muller et al., Chem. Ber., 1965, 98, 1097;

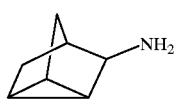

N-methyl-exo-bicyclo[2.2.1]heptan-2-ylamine prepared according to W. G. Kabalka et al., Synth. Commun., 1991, 20, 231;

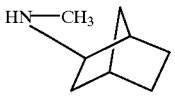

2,2,6,6-tetramethylcyclohexylamine prepared according to J. Chem. Soc., C, 1970, 1845.

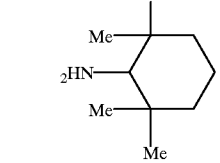

The alcohols of formula HOR$_2$ are either commercially available, or described in the literature, or prepared by known methods. For example, the alcohols of formula (XIV)

can be obtained by reduction of the corresponding ketones. The reduction is carried out by means of a reducing agent such as sodium borohydride in a solvent such as methanol or lithium aluminum hydride in a solvent such as tetrahydrofuran or diethyl ether, at a temperature between room temperature and the reflux temperature of the solvent.

Particularly, 2,2,6,6-tetramethylcyclohexanol is prepared according to the weekly proceedings of the sessions of the Académie des Sciences (Paris), 156, 1201.

The compounds of formula (I) can be obtained in enantiomerically pure form by using the compounds of formula (III) in enantiomerically pure form in step 1) of the process A or the compound of formula (XIV) in enantiomerically pure form in step 1) of the process B and using the compounds of formula (VII) or (VIII) in enantiomerically pure form in steps $d_1$ and $e_1$ of SCHEME 1 or in step $e_3$ of SCHEME 3 for the preparation of the compound of formula (II).

The racemic mixtures of the compounds of formula (III), (VII), (VIII) or (XIV) are resolved by the methods well known to those skilled in the art.

The compounds of formula (I) have a very good in vitro affinity for the $CB_2$ receptors under the experimental conditions described by Bouaboula et al., Eur. J. Biochem., 1993, 214, 173–180.

More particularly, the compounds of the present invention and their optional salts, are potent and selective ligands for the $CB_2$ receptors, having a Ki of generally between 0.1 and 100 nM. They are generally between 10 and 1000 times more active on the $CB_2$ receptors than on the $CB_1$ receptors and are active when administered orally.

The compounds (I) according to the invention are antagonists of the $CB_2$ receptors. The antagonistic activity of these compounds towards the $CB_2$ receptor was determined using various models. It is known that cannabinoid receptor agonists ($\Delta^9$-THC, WIN 55212-2 or CP 55940) are capable of inhibiting the adenylate cyclase activity induced by Forskoline as described by M. Rinaldi-Carmona et al., Journal of Pharmacology and Experimental Therapeutics, 1996, 278, 871–878. In this model the compounds (I) according to the invention are capable of totally blocking the effect of the cannabinoid receptor agonists.

It is further known that, at nanomolar concentrations, cannabinoid receptor agonists (WIN 55212-2 or CP 55940) are capable of increasing the DNA synthesis rate of human B cells co-stimulated with anti-Ig antibodies, resulting in an increase of about 40% in the thymidine incorporation (J. M. Derocq et al., FEBS Letters, 1995, 369, 177–182). If the compounds (I) according to the invention or one of their optional salts are used over a wide concentration range, from $10^{-10}$ M to $10^{-5}$ M, it is observed that they block the increase in the DNA synthesis rate of human B cells (stimulated as described above) induced by cannabinoid receptor agonists (WIN 55212-2 or CP 55940).

Also, cannabinoid receptor agonists (CP 55940 or WIN 55212-2) induce the activation of the mitogen activated protein kinases (MAPKs) in cells expressing the $CB_2$ receptor. The compounds (I) according to the invention specifically block this activation of the MAPKs which is induced by cannabinoid receptor agonists (CP 55940 or WIN 55212-2).

The compounds according to the invention or their optional salts, also have an in vivo affinity for the $CB_2$ cannabinoid receptors present in mouse spleen when they are administered intravenously, intraperitoneally or orally. Their activity was demonstrated by means of ex vivo binding experiments with [$^3$H]-CP 55940. The tests were performed under the experimental conditions described by M. Rinaldi-Carmona et al., Life Sciences, 1995, 56, 1941–1947.

The toxicity of the compounds of the present invention is compatible with their use as drugs.

By virtue of their remarkable properties, especially their high affinity and their selectivity for the $CB_2$ peripheral receptor, the compounds of formula (I) can be used as active principles of drugs, either as such or in the form of pharmaceutically acceptable salts.

The diseases which can be treated by the compounds (I) and their optional pharmaceutically acceptable salts are the pathologies involving immune system cells, or immune disorders, for example autoimmune diseases, diseases associated with organ transplants, infectious diseases, allergic diseases and the diseases of the gastrointestinal system, for example Crohn's disease. The following autoimmune diseases may be mentioned more particularly: systemic lupus erythematosus, connective tissue diseases, Sjögren's syndrome, ankylosing spondylarthritis, reactive arthritis, rheumatoid arthritis, undifferentiated spondylarthritis, Behcet's disease, hemolytic autoimmune anemia, multiple sclerosis and psoriasis. The allergic diseases to be treated can be of the immediate hypersensitivity or asthma type, for example. Likewise, the compounds (I) and their optional pharmaceutically acceptable salts, can be used to treat vascularitis, parasitic infections, viral infections, bacterial infections, amyloidosis and diseases affecting the lymphohematopoietic system lines.

Thus, according to another of its feaures, the present invention relates to method of treating the above diseases which comprises administering to a patient in need thereof an effective amount of a compound of formula (I) or one of its pharmaceutically acceptable salts.

According to another of its features, the present invention also relates to the use of the compounds of formula (I) for the preparation of drugs intended for the treatment of disorders involving the $CB_2$ cannabinoid receptors, and more particularly immune disorders as well as diseases in which the immune system is involved.

Furthermore, the compounds (I) or (XIII) according to the invention, either as such or in radiolabeled form, can be used as pharmacological tools in humans or animals for the detection and labeling of the $CB_2$ peripheral cannabinoid receptors. This constitutes a subsequent feature of the present invention.

The compounds of the present invention are generally administered in dosage units. Said dosage units are preferably formulated in pharmaceutical compositions in which the active principle is mixed with a pharmaceutical excipient.

Thus, according to another of its features, the present invention relates to pharmaceutical compositions in which a compound of formula (I) or one of its pharmaceutically acceptable salts is present as the active principle.

The compounds of formula (I) above and their pharmaceutically acceptable salts can be used in daily doses of 0.01 to 100 mg per kilogram of body weight of the mammal to be treated, preferably in daily doses of 0.1 to 50 mg/kg. In humans the dose can preferably vary from 0.5 to 4000 mg per day, more particularly from 2.5 to 1000 mg, depending on the age of the subject to be treated or the type of treatment: prophylactic or curative.

In the pharmaceutical compositions of the present invention for oral or sublingual administration, administration by inhalation, or subcutaneous, intra-muscular, intravenous, transdermal, local or rectal administration, the active principles can be administered to animals and humans in unit forms of administration, mixed with conventional pharmaceutical carriers. The appropriate unit forms of administration include oral forms such as tablets, gelatin capsules, powders, granules and solutions or suspensions to be taken orally, sublingual and buccal forms of administration, aerosols, implants, subcutaneous, intramuscular, intravenous, intranasal or intraocular forms of administration and rectal forms of administration.

When a solid composition is prepared in the form of tablets, a wetting agent such as sodium laurylsulfate can be added to the micronized or non-micronized active principle and the whole is mixed with a pharmaceutical vehicle such as silica, gelatine, starch, lactose, magnesium stearate, talc, gum arabic or the like. The tablets can be coated with sucrose, various polymers or other appropriate substances, or else they can be treated so as to have a prolonged or delayed activity and so as to release a predetermined amount of active principle continuously.

A preparation in the form of gelatin capsules is obtained by mixing the active principle with a diluent, such as a glycol or a glycerol ester, and incorporating the resulting mixture into soft or hard gelatin capsules.

A preparation in the form of a syrup or elixir can contain the active principle together with a sweetener, which is preferably calorie-free, methylparaben and propylparaben as antiseptics, a flavoring and an appropriate color.

The water-dispersible powders or granules can contain the active principle mixed with dispersants, wetting agents or suspending agents, such as polyvinylpyrrolidone, as well as with sweeteners or taste correctors.

Rectal administration is effected using suppositories, which are prepared with binders melting at the rectal temperature, for example cocoa butter or polyethylene glycols.

Parenteral, intranasal or intraocular administration is effected using aqueous suspensions, isotonic saline solutions or sterile and injectable solutions containing pharmacologically compatible dispersants and/or solubilizers, for example propylene glycol or polyethylene glycol.

Thus, to prepare an aqueous solution injectable intravenously, it is possible to use a co-solvent, namely an alcohol such as ethanol or a glycol such as polyethylene glycol or propylene glycol, and a hydrophilic surfactant such as Tween® 80. An oily solution injectable intramuscularly can be prepared by solubilizing the active principle with a triglyceride or a glycerol ester.

Local administration can be effected using creams, ointments or gels.

Transdermal administration can be effected using patches in the form of a multilaminate, or with a reservoir, in which the active principle can be in alcoholic solution.

Administration by inhalation can be effected using an aerosol containing sorbitan trioleate or oleic acid, for example, together with trichlorofluoromethane, dichlorofluoromethane, dichlorotetrafluoroethane or any other biologically compatible propellant gas; it is also possible to use a system containing the active principle, by itself or associated with an excipient, in powder form.

The active principle can also be formulated as microcapsules or microspheres, optionally with one or more carriers or additives.

The active principle can also be presented in the form of a complex with a cyclodextrin, for example α-, β- or γ-cyclodextrin, 2-hydroxypropyl-β-cyclodextrin or methyl-β-cyclodextrin.

Implants are among the prolonged release forms which can be used in the case of chronic treatments. They can be prepared in the form of an oily suspension or in the form of a suspension of microspheres in an isotonic medium.

In each dosage unit the active principle of formula (I) is present in amounts which are appropriate for the contemplated daily doses. In general each unit dosage is suitably adjusted depending on the dosage and the mode of administration envisioned, for example tablets, gelatine capsules and the like, sachets, vials, syrups and the like or drops so that such dosage unit contains from 0.5 to 1000 mg, preferably from 2.5 to 250 mg of active principle, to be administered once to four times a day.

The Examples which follow illustrate the invention without however implying a limitation.

The melting or decomposition points of the products, m.p., are measured in a capillary tube with a Tottoli apparatus.

The proton NMR spectra are run at 200 MHz in DMSO-$d_6$.

The apparatus used in preparative HPLC is a Prochrom LC 50 model with a column diameter of 50 mm and a maximum bed height between 35 and 40 cm. The conditions used are:

| | | | |
|---|---|---|---|
| * stationary phase: | Kromasil C 18-100 Å 10 μm | | |
| * mobile phase: | Eluent A: $H_2O$ | | |
| | Eluent B: $MeOH/H_2O$ (90/10; v/v) | | |
| * rate: | 114 ml/mm; position of the pumps: 8 mm | | |
| * elution gradient: | Time (min.) | % A | % B |
| | 0 | 10 | 90 |
| | 5 | 10 | 90 |
| | 80 | 4 | 96 |
| * Uv detection (λ: 230 nm); attenuation: 0.5 AUFS | | | |
| * Length of the cell . . . O | | | |

The apparatus used in analytical HPLC is a Hewlett Packard HPLC line. The conditions used are:

| | | | |
|---|---|---|---|
| * column: | Kromasil (Waters) statioilary phase C 18-100 Å 10 μm | | |
| * mobil phase: | Eluent A: $H_2O$ | | |
| | Eluent B: MeOH | | |
| * elution gradient | Time (min.) | % A | % B |
| | 0 | 20 | 80 |
| | 5 | 20 | 80 |
| | 50 | 7 | 93 |
| * rate: 1 ml/mm | | | |
| * UV detection (λ: 230 mm); attenuation = 8 | | | |
| * injected volume: 30 μl. | | | |

The following abbreviations are used in the Preparations and in the EXAMPLES:

Me, OMe: methyl, methoxy

Et, OEt: ethyl, ethoxy

EtOH: ethanol

MeOH: methanol

Ether: diethyl ether

Iso ether: diisopropyl ether

DMF: dimethylformamide

DMSO: dimethyl sulfoxide

DCM: dichloromethane $CCl_4$: carbon tetrachloride

THF: tetrahydrofuran

AcOEt: ethyl acetate $K_2CO_3$: potassium carbonate $Na_2CO_3$: sodium carbonate KHCO$_3$: potassium hydrogencarbonate
NaHCO$_3$: sodium hydrogencarbonate
NaCl: sodium chloride
Na$_2$SO$_4$: sodium sulfate
MgSO$_4$: magnesium sulfate
NaOH: sodium hydroxide
KOH: potassium hydroxide
AcOH: acetic acid
H$_2$SO$_4$: sulfuric acid
HCl: hydrochloric acid
HBr: hydrobromic acid
BOP: benzotriazol-1-yloxytris(dimethylamino) phosphonium hexafluorophosphate
DBU: 1,8-diazabicyclo[5.4.0]undec-7-ene
NH$_4$Cl: ammonium chloride
M.p.: melting point
B.p.: boiling point
RT: room temperature
Silica H: silica gel 60H marketed by Merck (DARMSTADT)
HPLC: high performance liquid chromatography
RTi: retention time
NMR: nuclear magnetic resonance
δ: chemical shift expressed in parts per million
s: singlet; bs: broad singlet; ss: split singlet; d: doublet; dd: doublet of doublets; t: triplet; qd: quadruplet; sept: septuplet; mt: multiplet; u: unresolved signals.

PREPARATIONS

Preparation 1.1

1-(3,4-Dichlorobenzyl)-5-(4-methylphenyl)pyrazole-3-carboxylic acid

A) Sodium salt of methyl 4-(4-methylphenyl)-2-oxo-4-oxidobut-3-enoate 6.24 g of sodium are dissolved in 150 ml of MeOH. After cooling to RT, 36.4 ml of 4'-methylacetophenone and then a solution of 37 ml of diethyl oxalate in 50 ml of MeOH are added. 100 ml of MeOH are then added to fluidize the reaction mixture, which is stirred for 2 hours at RT. 500 ml of ether are added and the mixture is stirred for 30 minutes at RT. The precipitate formed is filtered off, washed with ether and dried to give 57.4 g of the expected product.

B) Methyl 5-(4-methylphenyl)pyrazole-3-carboxylate

A mixture of 30 g of the compound obtained in the previous step and 100 ml of AcOH is cooled in an ice bath and 7.94 ml of 55% aqueous hydrazine solution are added dropwise. The reaction mixture is then refluxed for 5 hours and stirred overnight at RT. The precipitate formed is filtered off and washed with water to give a first crop. The filtrate is poured into a water/ice mixture and the precipitate formed is filtered off, washed with water and dried to give a second crop. The first and second crops are combined, washed with AcOEt and dried under vacuum to give 21.44 g of the expected product.

C) Methyl 1-(3,4-dichlorobenzyl)-5-(4-methylphenyl)pyrazole-3-carboxylate 2.03 g of a 60% dispersion of sodium hydride in oil are added in portions at RT to a suspension of 5 g of the compound obtained in the previous step in 50 ml of toluene and the reaction mixture is then heated at 65° C. for 1 hour. After cooling to RT, 5.82 g of 3,4-dichlorobenzyl bromide are added dropwise and the reaction mixture is then refluxed for 20 hours. It is cooled to RT and 100 ml of 50% aqueous NH$_4$Cl solution are added dropwise. After decantation, the organic phase is washed with saturated NaCl solution and dried over MgSO$_4$ and the solvent is evaporated off under vacuum. The residue is chromatographed on silica using a cyclohexane/AcOEt mixture (75/25; v/v) as the eluent to give 5.28 g of the expected product. M.p.=98.6° C.

D) 1-(3,4-Dichlorobenzyl)-5-(4-methylphenyl)pyrazole-3-carboxylic acid

A solution of 1.16 g of KOH in 20 ml of water is added at RT to a solution of 5.2 g of the compound obtained in the previous step in 100 ml of EtOH and the reaction mixture is then refluxed for 5 hours. It is stirred overnight at RT, 200 ml of N aqueous HCl solution are added and the precipitate formed is filtered off and dried under vacuum to give 5.12 g of the expected product. M.p.=171.5° C.

NMR: δ (ppm): 2.4 : s : 3H; 5.5 : s : 2H; 6.9 : s : 1H; 7.0 : dd : 1H; 7.3 : d : 1H; 7.35 : AA'-BB' system: 4H; 7.65 : d : 1H; 13.0 : bs : 1H An Overhauser effect (NOE) is observed between the benzyl protons (R$_4$R$_5$=H) and the protons g$_2$=g$_6$=H.

Preparation 1.2

1-(3-Chloro-4-methylbenzyl)-5-(4-methylphenyl) pyrazole-3-carboxylic acid

A) Methyl 1-(3-chloro-4-methylbenzyl)-5-(4-methylphenyl)pyrazole-3-carboxylate

This compound is prepared by the procedure described in step C of Preparation 1.1 from 5 g of the compound obtained in step B of Preparation 1.1, 2.03 g of a 60% dispersion of sodium hydride in oil, 100 ml of toluene and 4.22 g of 3-chloro-4-methylbenzyl chloride. 1.52 g of the expected product are obtained.

B) 1-(3-Chloro-4-methylbenzyl)-5-(4-methylphenyl) pyrazole-3-carboxylic acid

A solution of 0.36 g of KOH in 10 ml of water is added at RT to a solution of 1.52 g of the compound obtained in the previous step in 50 ml of EtOH and the reaction mixture is then refluxed overnight. It is concentrated under vacuum, the residue is taken up with water, the aqueous phase is washed with ether and acidified to pH 2 by the addition of 6 N HCl solution and the precipitate formed is filtered off, washed with water and dried under vacuum to give 1.42 g of the expected product. M.p.=108.5° C.

NMR: δ (ppm): 2.1 to 2.45 : 2s : 6H; 5.4 : s : 2H; 6.7 to 7.5 : u : 8H; 12.85 : bs : 1H Preparation 1.3

1-(3-Fluoro-4-methylbenzyl)-5-(4-methylphenyl) pyrazole-3-carboxylic acid and 1-(3-fluoro-4-methylbenzyl)-3-(4-methylphenyl)pyrazole-5-carboxylic acid A) Methyl 1-(3-fluoro-4-methylbenzyl)-5-(methylphenyl)pyrazole-3-carboxylate and methyl 1-(3-fluoro-4-methylbenzyl)-3-(methylphenyl)pyrazole-5-carboxylate 1.01 g of a 60% dispersion of sodium hydride in oil are added in portions at RT to a suspension of 2.5 g of the compound obtained in step B of Preparation 1.1 in 100 ml of toluene and the reaction mixture is then heated at 65° C. for 1 hour. After cooling to RT, 2.45 g of 3-fluoro-4-methylbenzyl bromide (Preparation 3.1) are added dropwise and the mixture is then refluxed for 48 hours. After cooling to RT, 50 ml of 50% aqueous NH₄Cl solution are added dropwise. After decantation, the organic phase is washed with saturated NaCl solution and dried over MgSO₄ and the solvent is evaporated off under vacuum. The residue is chromatographed on silica using an AcOEt/cyclohexane mixture (50/50; v/v) as the eluent to give 1.29 g of a mixture of the expected products.

B) 1-(3-Fluoro-4-methylbenzyl)-5-(4-methylphenyl)pyrazole-3-carboxylic acid and 1-(3-fluoro-4-methylbenzyl)-3-(4-methylphenyl)pyrazole-5-carboxylic acid A solution of 0.3 g of KOH in 10 ml of water is added at RT to a solution of 1.2 g of the mixture of compounds obtained in the previous step in 50 ml of EtOH and the reaction mixture is then refluxed for 5 hours and stirred overnight at RT. It is concentrated under vacuum, the residue is taken up with water, the aqueous phase is washed with AcOEt and acidified to pH 2 by the addition of 6 N HCl solution and the precipitate formed is filtered off, washed with water and dried under vacuum to give 0.95 g of a mixture of the expected products.

Preparation 1.4

1-(3,4-Dichlorobenzyl)-5-(4-methoxyphenyl)pyrazole-3-carboxylic acid

A) Sodium salt of methyl 4-(4-methoxyphenyl)-2-oxo-4-oxidobut-3-enoate 3.9 g of sodium are dissolved in 100 ml of MeOH. After cooling to RT, 25.4 g of 4'-methoxyacetophenone and then a solution of 23 ml of diethyl oxalate in 50 ml of MeOH are added and the mixture is stirred for 2 hours at RT. 500 ml of ether are added and the mixture is stirred for 30 minutes at RT. The precipitate formed is filtered off, washed with ether and dried to give 33.4 g of the expected product.

B) Methyl 5-(4-methoxyphenyl)pyrazole-3-carboxylate

A mixture of 9 g of the compound obtained in the previous step and 100 ml of AcOH is cooled in an ice bath and 2.2 ml of hydrazine monohydrate are added dropwise. The reaction mixture is then refluxed for 5 hours and stirred overnight at RT. It is poured into a water/ice mixture and the precipitate formed is filtered off and washed with water. It is taken up with DCM, an insoluble material is filtered off, the filtrate is dried over MgSO₄ and the solvent is evaporated off under vacuum to give 7.1 g of the expected product.

C) Methyl 1-(3,4-dichlorobenzyl)-5-(4-methoxyphenyl)pyrazole-3-carboxylate

This compound is prepared by the procedure described in step C of Preparation 1.1 from 3.5 g of the compound obtained in the previous step, 1.32 g of a 60% dispersion of sodium hydride in oil, 150 ml of toluene and 3.77 g of 3,4-dichlorobenzyl bromide. The product is chromatographed on silica using a cyclohexane/AcOEt mixture (60/40; v/v) as the eluent to give 2.4 g of the expected product. M.p.=95.5° C.

NMR: δ (ppm): 3.8 : 2s : 6H; 5.45 : s : 2H; 6.8 to 7.1 : u : 4H; 7.25 : d : 1H; 7.35 : d : 2H; 7.55 : d : 1H D) 1-(3,4-Dichlorobenzyl)-5-(4-methoxyphenyl)pyrazole-3-carboxylic acid This compound is prepared by the procedure described in step B of Preparation 1.2 from 2.4 g of the compound obtained in the previous step, 50 ml of EtOH, 0.51 g of KOH and 10 ml of water. 2.23 g of the expected product are obtained.

Preparation 1.5

1-(3-Chloro-4-methylbenzyl)-5-(4-methoxyphenyl)pyrazole-3-carboxylic acid and 1-(3-chloro-4-methylbenzyl)-3-(4-methoxyphenyl)pyrazole-5-carboxylic acid A) Methyl 1-(3-chloro-4-methylbenzyl)-5-(4-methoxyphenyl)pyrazole-3-carboxylate and methyl 1-(3-chloro-4-methylbenzyl)-3-(4-methoxyphenyl)pyrazole-5-carboxylate A mixture of these two compounds is prepared by the procedure described in step A of Preparation 1.3 from 3.5 g of the compound obtained in step B of Preparation 1.4, 1.32 g of a 60% dispersion of sodium hydride in oil, 100 ml of toluene and 2.75 g of 3-chloro-4-methylbenzyl chloride. 1.93 g of a mixture of the expected products are obtained.

B) 1-(3-Chloro-4-methylbenzyl)-5-(4-methoxyphenyl)pyrazole-3-carboxylic acid and 1-(3-chloro-4-methylbenzyl)-3-(4-methoxyphenyl)pyrazole-5-carboxylic acid A mixture of these two compounds is prepared by the procedure described in step B of Preparation 1.3 from 1.9 g of the mixture of compounds obtained in the previous step, 50 ml of EtOH, 0.43 g of KOH and 10 ml of water. 1.73 g of a mixture of the expected products are obtained.

Preparation 1.6

1-(3-Chloro-4-methylbenzyl)-5-(4-fluorophenyl)pyrazole-3-carboxylic acid

A) Sodium salt of methyl 4-(4-fluorophenyl)-2-oxo-4-oxidobut-3-enoate

This compound is prepared by the procedure described in step A of Preparation 1.1 from 4.16 g of sodium in 100 ml of MeOH, 21.87 ml of 4'-fluoroacetophenone and 24.72 ml of diethyl oxalate in 50 ml of MeOH. 42.68 g of the expected product are obtained.

B) Methyl 5-(4-fluorophenyl)pyrazole-3-carboxylate

This compound is prepared by the procedure described in step B of Preparation 1.1 from 15 g of the compound obtained in the previous step, 100 ml of AcOH and 3.73 ml of 55% aqueous hydrazine solution. After stirring overnight at RT, the reaction mixture is poured into a water/ice mixture and the precipitate formed is filtered off, washed with water and dried to give 10.74 g of the expected product.

C) Methyl 1-(3-chloro-4-methylbenzyl)-5-(4-fluorophenyl)pyrazole-3-carboxylate

This compound is prepared by the procedure described in step C of Preparation 1.1 from 3.5 g of the compound obtained in the previous step, 1.4 g of a 60% dispersion of sodium hydride in oil, 100 ml of toluene and 4.45 g of 3-chloro-4-methylbenzyl iodide (Preparation 3.2) in 50 ml of toluene. The product is chromatographed on silica using a cyclohexane/AcOEt mixture (70/30; v/v) as the eluent to give 1.57 g of the expected product. M.p.=110° C.

D) 1-(3-Chloro-4-methylbenzyl)-5-(4-fluorophenyl)pyrazole-3-carboxylic acid

This compound is prepared by the procedure described in step B of Preparation 1.2 from 1.55 g of the compound obtained in the previous step, 50 ml of EtOH, 0.36 g of KOH and 10 ml of water. 1.46 g of the expected product are obtained. M.p.=120° C.

Preparation 1.7

1-(2,4-Dichlorobenzyl)-5-(4-chlorophenyl)pyrazole-3-carboxylic acid

A) Sodium salt of methyl 4-(4-chlorophenyl)-2-oxo-4-oxidobut-3-enoate

This compound is prepared by the procedure described in step A of Preparation 1.1 from 12.66 g of sodium in 270 ml of MeOH, 68.4 ml of 4-chloroacetophenone and 71.8 ml of diethyl oxalate in 110 ml of MeOH. 97 g of the expected product are obtained.

B) Methyl 5-(4-chlorophenyl)pyrazole-3-carboxylate

This compound is prepared by the procedure described in step B of Preparation 1.4 from 15 g of the compound obtained in the previous step, 65 ml of AcOH and 3.05 ml of hydrazine monohydrate. The precipitate obtained is triturated in a mixture of 100 ml of DCM and 50 ml of AcOEt, filtered off and dried to give 8.13 g of the expected product. M.p.=215° C.

C) Methyl 1-(2,4-dichlorobenzyl)-5-(4-chlorophenyl)pyrazole-3-carboxylate

A solution of 5.07 g of the compound obtained in the previous step in 100 ml of toluene is added dropwise at RT to a suspension in 100 ml of toluene of 1.02 g of a 60% dispersion of sodium hydride in oil and the mixture is then heated at 65° C. for 1 hour. 3.12 ml of 2,4-dichlorobenzyl chloride are then added and the reaction mixture is refluxed for 20 hours. It is cooled to RT and 100 ml of 50% aqueous NH$_4$Cl solution are added. After decantation, the organic phase is washed with saturated NaCl solution and dried over MgSO$_4$ and the solvent is evaporated off under vacuum. The residue is chromatographed on silica using a toluene/DCM/AcOEt mixture (80/10/10; v/v/v) as the eluent to give 3.68 g of the expected product. M.p.=105° C.

D) 1-(2,4-Dichlorobenzyl)-5-(4-chlorophenyl)pyrazole-3-carboxylic acid

This compound is prepared by the procedure described in step D of Preparation 1.1 from 3.6 g of the compound obtained in the previous step, 60 ml of MeOH, 1.27 g of KOH and 6 ml of water. 3.52 g of the expected product are obtained. M.p.=185° C.

Preparation 1.8

1-(3-Chloro-4-methylbenzyl)-5-(3,4-dimethylphenyl)pyrazole-3-carboxylic acid

A) Sodium salt of methyl 4-(3,4-dimethylphenyl)-2-oxo-4-oxidobut-3-enoate

This compound is prepared by the procedure described in step A of Preparation 1.1 from 3.9 g of sodium in 100 ml of MeOH, 25 g of 3',4'-dimethylacetophenone and 23 ml of diethyl oxalate in 50 ml of MeOH. 39.42 g of the expected product are obtained.

B) Methyl 5-(3,4-dimethylphenyl)pyrazole-3-carboxylate

This compound is prepared by the procedure described in step B of Preparation 1.6 from 10 g of the compound obtained in the previous step in 150 ml of AcOH and 2.2 ml of 55% aqueous hydrazine solution. 9 g of the expected product are obtained.

C) Methyl 1-(3-chloro-4-methylbenzyl)-5-(3,4-dimethylphenyl)pyrazole-3-carboxylate This compound is prepared by the procedure described in step C of Preparation 1.1 from 1.52 g of a 60% dispersion of sodium hydride in oil, 4 g of the compound obtained in the previous step, 70 ml of toluene and 5.8 g of 3-chloro-4-methylbenzyl iodide (Preparation 3.2). The product obtained is purified by trituration in hexane and then filtration and washing with hexane to give 2.84 g of the expected product. M.p.=88° C.

NMR: δ (ppm): 2.0 to 2.35 : u : 9H; 3.95 : s : 3H; 5.3 : s : 2H; 6.6 to 7.4 : u : 7H D) 1-(3-Chloro-4-methylbenzyl)-5-(3,4-dimethylphenyl)pyrazole-3-carboxylic acid This compound is prepared by the procedure described in step B of Preparation 1.2 from 1.8 g of the compound obtained in the previous step in 30 ml of EtOH and 0.392 g of KOH in 30 ml of water. 1.6 g of the expected product are obtained. M.p.=163° C.

Preparation 1.9

1-(3-Chloro-4-fluorobenzyl)-5-(3,4-dimethylphenyl)pyrazole-3-carboxylic acid

A) Methyl 1-(3-chloro-4-fluorobenzyl)-5-(3,4-dimethylphenyl)pyrazole-3-carboxylate This compound is prepared by the procedure described in step C of Preparation 1.1 from 2.5 g of the compound obtained in step B of Preparation 1.8, 50 ml of toluene, 0.88 g of a 60% dispersion of sodium hydride in oil and 2.5 g of 3-chloro-4-fluorobenzyl bromide (Preparation 3.3). The product is purified by trituration in AcOEt and then filtration and drying to give 3.6 g of the expected product.

B) 1-(3-Chloro-4-fluorobenzyl)-5-(3,4-dimethylphenyl)pyrazole-3-carboxylic acid

This compound is prepared by the procedure described in step B of Preparation 1.2 from 1.6 g of the compound obtained in the previous step in 25 ml of EtOH and 0.481 g of KOH in 10 ml of water. 1.22 g of the expected product are obtained.

NMR: δ (ppm): 2.2 : 2s : 6H; 5.35 : s : 2H; 6.6 to 7.4 : u : 7H

Preparation 1.10

1-(4-Methylbenzyl)-5-(4-chloro-3-methylphenyl)pyrazole-3-carboxylic acid

A) Sodium salt of methyl 4-(4-chloro-3-methylphenyl)-2-oxo-4-oxidobut-3-enoate

This compound is prepared by the procedure described in step A of Preparation 1.1 from 7.6 g of sodium in 100 ml of MeOH, 55.6 g of 4'-chloro-3'-methylacetophenone and 45 ml of diethyl oxalate in 100 ml of MeOH. 85.8 g of the expected product are obtained.

B) Methyl 5-(4-chloro-3-methylphenyl)pyrazole-3-carboxylate

This compound is prepared by the procedure described in step B of Preparation 1.4 from 15 g of the compound obtained in the previous step in 150 ml of AcOH and 2.9 ml of hydrazine monohydrate. After stirring overnight at RT, the reaction mixture is poured into iced water and the precipitate formed is filtered off and washed with water to give 13 g of the expected product after drying.

C) Methyl 1-(4-methylbenzyl)-5-(4-chloro-3-methylphenyl)pyrazole-3-carboxylate

This compound is prepared by the procedure described in step C of Preparation 1.1 from 5 g of the compound obtained in the previous step in 50 ml of toluene, 1.8 g of a 60% dispersion of sodium hydride in oil and 4.07 g of 4-methylbenzyl bromide. 4.6 g of the expected product are obtained. M.p.=98° C.

NMR: δ (ppm): 2.0 to 2.4 : 2s : 6H; 3.8 : s : 3H; 5.4 : s : 2H; 6.7 to 7.6 : u : 8H D) 1-(4-Methylbenzyl)-5-(4-chloro-3-methylphenyl) pyrazole-3-carboxylic acid This compound is prepared by the procedure described in step B of Preparation 1.2 from 4 g of the compound obtained in the previous step in 100 ml of EtOH and 0.95 g of KOH in 20 ml of water. 3.4 g of the expected product are obtained. M.p.=180° C.

NMR: δ (ppm): 2.25 : s : 3H; 2.35 : s : 3H; 5.4 : s : 2H; 6.7 to 7.15 : u : 5H; 7.25 : dd : 1H; 7.4 to 7.6 : u : 22H The esters and then the acids described in TABLE 1 below are prepared by the procedures described in step C (from the compound obtained in step B of Preparation 1.10 and the appropriate benzyl halides) and then in step D of Preparation 1.10.

TABLE 1

Z = OMe, OH

| Preparation | w₃ | w₄ |
|---|---|---|
| 1.11 | H | F |
| 1.12 | Cl | Me |
| 1.13 | Cl | F |

Preparation 1.11: Z=OMe

NMR: δ (ppm): 2.35 : s : 3H; 3.85 : s : 3H; 5.5 : s : 2H; 6.8 to 7.6 : u : 8H

Preparation 1.14

1-[1-(2,4-Dichlorophenyl)ethyl]-5-(4-chlorophenyl) pyrazole-3-carboxylic acid

A) Methyl 1-[1-(2,4-dichlorophenyl)ethyl]-5-(4-chlorophenyl)pyrazole-3-carboxylate 0.3 g of a 60% dispersion of sodium hydride in oil is added in portions at RT to a suspension of 1.5 g of the compound obtained in step B of Preparation 1.7 in 50 ml of toluene and the mixture is then heated at 65° C. for 30 minutes. After cooling to RT, 1.77 g of 1-(1-bromoethyl)-2,4-dichlorobenzene (Preparation 3.4) are added dropwise and the reaction mixture is then refluxed for 5 days. After cooling to RT, it is poured into 100 ml of 50% aqueous NH₄Cl solution cooled to 0° C. The mixture is extracted with AcOEt, the organic phase is washed with water and with saturated NaCl solution and dried over MgSO₄ and the solvent is evaporated off under vacuum. The residue is chromatographed on silica using a toluene/AcOEt mixture (95/5; v/v) as the eluent to give 1.02 g of the expected product.

B) 1-[1-(2,4-Dichlorophenyl)ethyl]-5-(4-chlorophenyl) pyrazole-3-carboxylic acid A solution of 0.35 g of KOH in 5 ml of water is added at RT to a solution of 1.02 g of the compound obtained in the previous step in 20 ml of MeOH and the reaction mixture is then refluxed for 2 hours. It is poured into 100 ml of 5% HCl solution cooled to 0° C. and the precipitate formed is filtered off, washed with water and dried under vacuum to give 0.74 g of the expected product. M.p.=80° C.

Preparation 1.15

1-(3,4-Dichlorobenzyl)-5-(2,6-dimethoxyphenyl) pyrazole-3-carboxylic acid

A) Potassium salt of ethyl 4-(2,6-dimethoxyphenyl)-2-oxo-4-oxidobut-3-enoate

A mixture of 18 g of 2',6'-dimethoxyacetophenone and 54 ml of EtOH is heated to 50° C. and a solution of 13.4 g of potassium tert-butylate in 72 ml of EtOH is added over 5 minutes. The reaction mixture is heated to the reflux point, 16.3 ml of diethyl oxalate are added over 10 minutes and reflux is continued for 1 hour. 40 ml of EtOH are distilled, the mixture is then stirred for 2 hours 30 minutes, the temperature being allowed to fall to RT, and the precipitate formed is filtered off, washed with EtOH and dried under vacuum at 60° C. to give 31 g of the expected product.

B) Methyl 5-(2,6-dimethoxyphenyl)pyrazole-3-carboxylate

This compound is prepared by the procedure described in step B of Preparation 1.4 from 4 g of the compound obtained in the previous step, 50 ml of AcOH and 0.7 ml of hydrazine monohydrate. After stirring overnight at RT, the reaction mixture is poured into a water/ice mixture and extracted with AcOEt, the organic phase is washed with saturated NaCl solution and dried over Na₂SO₄ and the solvent is partially concentrated under vacuum. The precipitate formed is filtered off and dried to give 2.53 g of the expected product.

C) 1-(3,4-Dichlorobenzyl)-5-(2,6-dimethoxyphenyl) pyrazole-3-carboxylic acid

This compound is prepared by the procedure described in step C of Preparation 1.1 from 2.5 g of the compound obtained in the previous step, 50 ml of toluene, 0.88 g of a 60% dispersion of sodium hydride in oil and 2.16 g of 3,4-dichlorobenzyl bromide. After refluxing overnight, the reaction mixture is cooled to RT, 50 ml of 50% aqueous NH₄Cl solution are added dropwise and the precipitate formed is filtered off and dried to give 1.1 g of the expected product.

NMR: δ (ppm): 3.5 : s : 6H; 4.8 : very broad signal : 1H; 4.95 : s : 2H; 6.25 : s : 1H; 6.6 : d : 2H; 6.85 : dd : 1H; 6.95 : d : 1H; 7.3 : t : 1H; 7.4 : d : 1H Preparation 1.16

1-(4-Fluorobenzyl)-5-(3,4-dimethylphenyl)pyrazole-3-carboxylic acid

A) Methyl 1-(4-fluorobenzyl)-5-(3,4-dimethylphenyl) pyrazole-3-carboxylate

This compound is prepared by the procedure described in step C of Preparation 1.1 from 2.3 g of the compound obtained in step B of Preparation 1.8, 50 ml of toluene, 0.88 g of a 60% dispersion of sodium hydride in oil and 2.08 g of 4-fluorobenzyl bromide. 1 g of the expected product is obtained. M.p.=93° C.

NMR: δ (ppm): 2.25 : 2s : 6H; 3.8 : s : 3H; 5.4 : s : 2H; 6.85 : s : 1H; 6.9 to 7.3 : u : 7H B) 1-(4-Fluorobenzyl)-5-(3,4-dimethylphenyl)pyrazole-3-carboxylic acid This compound is prepared by the procedure described in step B of Preparation 1.14 from 1 g of the compound obtained in the previous step, 15 ml of MeOH, 0.406 g of KOH and 15 ml of water. 0.94 g of the expected product is obtained. M.p.=141° C.

NMR: δ (ppm): 2 : 2s : 6H; 3.4 : bs : 1H; 5.35 : s : 2H; 6.75 : s : 1H; 6.8 to 7.3 : u : 7H Preparation 1.17

1-(2,4-Dichlorobenzyl)-5-(4-methylphenyl)pyrazole-3-carboxylic acid

A) Methyl 1-(2,4-dichlorobenzyl)-5-(4-methylphenyl)pyrazole-3-carboxylate

This compound is prepared by the procedure described in step C of Preparation 1.1 from 2.5 g of the compound obtained in step B of Preparation 1.1, 1 g of a 60% dispersion of sodium hydride in oil, 50 ml of toluene and 2.3 g of 2,4-dichlorobenzyl chloride. 2.53 g of the expected product are obtained. M.p.=105° C.

B) 1-(2,4-Dichlorobenzyl)-5-(4-methylphenyl)pyrazole-3-carboxylic acid

A solution of 0.5 g of KOH in 15 ml of water is added at RT to a suspension of 1.5 g of the compound obtained in the previous step in 15 ml of MeOH and the reaction mixture is then refluxed for 2 hours. It is concentrated under vacuum, the residue is poured into a 1N HCl/ice mixture, the precipitate formed is filtered off, washed with water and dried under vaccum to give 1.4 g of the expected product.

NMR: $\delta$ (ppm): 2.3 : s : 3H; 5.45 : s : 2H; 6.6 to 7.7 : u : 8H; 12.85 : bs : 1H.

Preparation 1.18

1-(4-Ethylbenzyl)-5-(4-chloro-3-methylphenyl)pyrazole-3-carboxylic acid

A) Methyl 1-(4-ethylbenzyl)-5-(4-chloro-3-methylphenyl)pyrazole-3-carboxylate

This compound is prepared by the procedure described in step C of Preparation 1.1 from 2.5 g of the compound obtained in step B of Preparation 1.10 in 50 ml of toluene, 0.88 g of a 60% dispersion of sodium hydride in oil and 2 g of 4-ethylbenzyl bromide (Preparation 3.5). After hydrolysis with 50% aqueous $NH_4Cl$ solution and then decantation, the organic phase is concentrated under vacuum. The residue is extracted with AcOEt, the organic phase is washed with saturated NaCl solution, dried over $Na_2SO_4$ and the solvent is evaporated off under vacuum. The residue is chromatographed on silica using a cyclohexane/AcOEt mixture (80/20; v/v) as the eluent to give 2.63 g of the expected product.

B) 1-(4-Ethylbenzyl)-5-(4-chloro-3-methylphenyl)pyrazole-3-carboxylic acid

This compound is prepared by the procedure described in step B of Preparation 1.17 from 2.5 g of the compound obtained in the previous step in 20 ml of MeOH and 0.57 g of KOH in 20 ml of water. 2.2 g of the expected product are obtained.

NMR: $\delta$ (ppm): 1.1 : t : 3H; 2.3 : s : 3H; 2.5 : mt : 2H; 5.4 : s : 2H; 6.7 to 7.7 : u : 8H; 12.9 : bs : 1H.

Preparation 1.19

1-(3,4-Dichlorobenzyl)-5-(4-chloro-3-methylphenyl)pyrazole-3-carboxylic acid 0.88 g of a 60% dispersion of sodium hydride in oil is added in portions at RT to a suspension of 2.5 g of the compound obtained in step B of Preparation 1.10 in 25 ml of toluene and the reaction mixture is then heated for 1 hour at 65° C. After cooling to RT, a solution of 2.4 g of 3,4-dichlorobenzyl bromide in 25 ml of toluene is added dropwise and the reaction mixture is then refluxed overnight. After cooling to RT, the precipitate formed is filtered off and dried to give 2 g of the expected product which is used as such.

Preparation 1.20

1-(2,4-Dichlorobenzyl)-5-(4-chloro-3-methylphenyl)pyrazole-3-carboxylic acid

A) Methyl 1-(2,4-dichlorobenzyl)-5-(4-chloro-3-methylphenyl)pyrazole-3-carboxylate This compound is prepared by the procedure described in step A of Preparation 1.18 from 2.5 g of the compound obtained in step B of Preparation 1.10 in 25 ml of toluene, 0.88 g of a 60% dispersion of sodium hydride in oil and 1.6 ml of 2,4-dichlorobenzyl chloride in 25 ml of toluene. 0.86 g of the expected product is obtained.

B) 1-(2,4-Dichlorobenzyl)-5-(4-chloro-3-methylphenyl)pyrazole-3-carboxylic acid

This compound is prepared by the procedure described in step B of Preparation 1.17 from 0.5 g of the compound obtained in the previous step in 15 ml of MeOH and 0.205 g of KOH in 15 ml of water. 0.31 g of the expected product is obtained.

NMR: $\delta$ (ppm): 2.25 : s : 3H; 5.4 : s : 2H; 6.6 to 7.6 : u : 7H; 3.33 : with DOH : 1H.

An Overhauser effect (NOE) is observed between the benzyl protons ($R_4=R_5H$) and the protons $g_2=g_6=H$.

Preparation 1.21

1-(4-Methylbenzyl)-5-(3,4-dichlorophenyl)pyrazole-3-carboxylic acid

A) Sodium salt of methyl 4-(3,4-dichlorophenyl)-2-oxo-4-oxidobut-3-enoate 15.17 g of sodium are dissolved in 500 ml of MeOH. After cooling to RT, 124.97 g of 3',4'-dichloroacetophenone and then a solution of 91 ml of diethyl oxalate in 400 ml of MeOH are added and the reaction mixture is stirred for 2 hours at RT, 1 liter of ether is added and the reaction mixture is stirred for 30 minutes at RT. The precipitate formed is filtered off, washed with ether and dried to give 140.77 g of the expected product.

B) Methyl 5-(3,4-dichlorophenyl)pyrazole-3-carboxylate

This compound is prepared by the procedure described in step B of Preparation 1.1 from 15 g of the compound obtained in the previous step in 150 ml of AcOH and 6 ml of 55% aqueous hydrazine solution. After stirring overnight at RT, the reaction mixture is poured into iced water, the precipitate formed is filtered off, washed with water and dried to give 12.9 g of the expected product.

C) Methyl 1-(4-methylphenyl)-5-(3,4-dichlorophenyl)pyrazole-3-carboxylate

This compound is prepared by the procedure described in step A of Preparation 1.18 from 2.5 g of the compound obtained in the previous step in 25 ml of toluene, 0.88 g of a 60% dispersion of sodium hydride in oil and 1.9 g of 4-methylbenzyl bromide in 25 ml of toluene. 0.82 g of the expected product is obtained.

D) 1-(4-Methylbenzyl)-5-(3,4-dichlorophenyl)pyrazole-3-carboxylic acid

This compound is prepared by the procedure described in step B of Preparation 1.17 from 0.7 g of the compound obtained in the previous step in 15 ml of MeOH and 0.252 g of KOH in 15 ml of water. 0.65 g of the expected product is obtained.

NMR: $\delta$ (ppm): 2.2 : s : 3H; 5.35 : s : 2H; 6.7 to 7.2 : u : 5H; 7.4 : dd : 1H; 7.6 to 7.8 : u : 2H; 12.85 : bs : 1H.

Preparation 1.22

1-(3-Chloro-4-methylbenzyl)-5-(3,4-dichlorophenyl)pyrazole-3-carboxylic acid

A) Methyl 1-(3-chloro-4-methylbenzyl)-5-(3,4-dichlorophenyl)pyrazole-3-carboxylate This compound is prepared by the procedure described in step A of Preparation 1.18 from 20.51 g of the compound obtained in step B of Preparation 1.21 in 350 ml of toluene, 2.18 g of a 60% dispersion of sodium hydride in oil and 21.96 g of 3-chloro-4-methylbenzyl iodide (Preparation 3.2). 21.79 g of the expected product are obtained after crystallization from hexane.

B) 1-(3-Chloro-4-methylbenzyl)-5-(3,4-dichlorophenyl)pyrazole-3-carboxylic acid

This compound is prepared by the procedure described in step B of Preparation 1.17 from 21.79 g of the compound obtained in the previous step in 50 ml of MeOH and 8.93 g of KOH in 50 ml of water. 17.43 g of the expected product, which is used as such, are obtained.

Preparation 1.23

1-(2,4-Dichlorobenzyl)-5-(4-methylthiophenyl)pyrazole-3-carboxylic acid

A) 4'-Methylthioacetophenone 11.8 ml of acetyl chloride are added dropwise at a temperature of between 0° C. and 10° C. to a suspension of 20.4 g of aluminum chloride in 85 ml of chloroform. 15 ml of thioanisole are then added dropwise at 0–5° C. and the reaction mixture is stirred for 1 hour 30 minutes at RT. It is cooled to 0° C., hydrolysed by the addition of 100 ml of water and extracted with chloroform. The organic phase is washed with water and dried over $Na_2SO_4$ and the solvent is evaporated off under vacuum to give 10.7 g of the expected product after crystallization from EtOH and recrystallization from heptane.

B) Sodium salt of methyl 4-(4-methylthiophenyl)-2-oxo-4-oxidobut-3-enoate 1.48 g of sodium are dissolved in 35 ml of MeOH and this solution is added quickly to a suspension of 10.7 g of the compound obtained in the previous step and 9.8 ml of diethyl oxalate in 80 ml of MeOH cooled to 0° C. The reaction mixture is stirred for 30 minutes at RT, refluxed for 1 hour and then stirred for 2 hours at RT. It is poured into 400 ml of ether, the mixture is stirred for 15 minutes and the precipitate formed is filtered off, washed with ether and dried to give 12.8 g of the expected product.

C) Methyl 5-(4-methylthiophenyl)pyrazole-3-carboxylate

This compound is prepared by the procedure described in step B of Preparation 1.1 from 15 g of the compound obtained in the previous step in 140 ml of AcOH and 7 ml of 55% aqueous hydrazine solution. After stirring overnight at RT, the reaction mixture is poured into a water/ice mixture, the precipitate formed is filtered off, washed with water and dried under vaccum over KOH to give 12.96 g of the expected product.

D) Methyl 1-(2,4-dichlorobenzyl)-5-(4-methylthiophenyl)pyrazole-3-carboxylate

This compound is prepared by the procedure described in step A of Preparation 1.18 from 5 g of the compound obtained in the previous step in 100 ml of toluene, 1.063 g of a 60% dispersion of sodium hydride in oil and 3.4 ml of 2,4-dichlorobenzyl chloride. 3.2 g of the expected product are obtained.

E) 1-(2,4-Dichlorobenzyl)-5-(4-methylthiophenyl)pyrazole-3-carboxylic acid

This compound is prepared by the procedure described in step B of Preparation 1.14 from 1.52 g of the compound obtained in the previous step in 30 ml of MeOH and 0.7 g of KOH in 25 ml of water. 1.4 g of the expected product are obtained after drying under vacuum.

NMR: δ (ppm): 2.5 : s : 3H; 5.4 : s : 2H; 6.6 to 7.6 : u : 8H; 12.8 : bs : 1H.

Preparation 1.24

1-(2,4-Dichlorobenzyl)-5-(4-trifluoromethylphenyl)pyrazole-3-carboxylic acid

A) Sodium salt of methyl 4-(4-trifluoromethylphenyl)-2-oxo-4-oxidobut-3-enoate

This compound is prepared by the procedure described in step A of Preparation 1.4 from 4'-trifluoromethylacetophenone.

B) Methyl 5-(4-trifluoromethylphenyl)pyrazole-3-carboxylate

This compound is prepared by the procedure described in step C of Preparation 1.23 from 6.37 g of the compound obtained in the previous step in 50 ml of AcOH and 3 ml of 55% aqueous hydrazine solution. 5.43 g of the expected product are obtained.

C) Methyl 1-(2,4-dichlorobenzyl)-5-(4-trifluoromethylphenyl)pyrazole-3-carboxylate This compound is prepared by the procedure described in step A of Preparation 1.18 from 2.5 g of the compound obtained in the previous step in 150 ml of toluene, 0.44 g of a 60% dispersion of sodium hydride in oil and 2 ml of 2,4-dichlorobenzyl chloride. 1.82 g of the expected product are obtained.

D) 1-(2,4-Dichlorobenzyl)-5-(4-trifluoromethylphenyl)pyrazole-3-carboxylic acid

This compound is prepared by the procedure described in step B of Preparation 1.14 from 1.6 g of the compound obtained in the previous step in 30 ml of MeOH and 0.63 g of KOH in 30 ml of water. 1.5 g of the expected product are obtained.

NMR: δ (ppm): 5.45 : s : 2H; 6.85 : d : 1H; 6.95 : s : 1H; 7.3 : dd : 1H; 7.5 : d : 1H; 7.55 to 7.8 : AA'-BB' system: 4H; 12.9 : bs : 1H Preparation 1.25

1-[1-(3,4-Dichlorophenyl)ethyl]-5-(4-methylphenyl)pyrazole-3-carboxylic acid

A) Methyl 1-[1-(3,4-dichlorophenyl)ethyl]-5-(4-methylphenyl)pyrazole-3-carboxylate 1 g of a 60% dispersion of sodium hydride in oil is added in portions at RT to a suspension of 2.5 g of the compound obtained in step B of Preparation 1.1 in 25 ml of toluene and the reaction mixture is then heated at 65° C. for 1 hour. A solution of 3 g of 1-(1-bromoethyl)-3,4-dichlorobenzene (Preparation 3.6) in 25 ml of toluene is then added dropwise and the mixture is then refluxed overnight. It is cooled to 0° C. and 100 ml of 50% aqueous $NH_4Cl$ solution are added dropwise. After decantation, the organic phase is washed with saturated NaCl solution and dried over $Na_2SO_4$ and the solvent is evaporated off under vacuum. The residue is chromatographed on silica using a cyclohexane/AcOEt mixture (75/25 ; v/v) as the eluent to give 1.6 g of the expected product.

B) 1-[1-(3,4-Dichlorophenyl)ethyl]-5-(4-methylphenyl)pyrazole-3-carboxylic acid

A solution of 0.5 g of KOH in 15 ml of water is added at RT to a suspension of 1.4 g of the compound obtained in the previous step in 15 ml of MeOH and the reaction mixture is refluxed for 2 hours. After concentration of MeOH under vacuum, it is poured into a 1N HCl/ice mixture, the precipitate formed is filtered off, washed with water and dried under vacuum over KOH to give 1.25 g of the expected product.

NMR: δ (ppm): 1.85 : d : 3H; 2.4 : s : 3H; 5.7 : qd : 1H; 6.85 : s : 1H; 7.05 : dd : 1H; 7.2 to 7.45 : u : 5H; 7.65 : d : 1H; 12.95 : bs : 1H.

Preparation 1.26

1-[1-(4-Methylphenyl)ethyl]-5-(4-chloro-3-methylphenyl)pyrazole-3-carboxylic acid A) Methyl 1-[1-(4-methylphenyl)ethyl]-5-(4-chloro-3-methylphenyl) pyrazole-3-carboxylate This compound is prepared by the procedure described in step A of Preparation 1.25 from 2.5 g of the compound obtained in step B of Preparation 1.10 in 25 ml of toluene, 0.88 g of a 60% dispersion of sodium hydride in oil and 2.3 g of 1-(1-bromoethyl)-4-methylbenzene (Preparation 3.7) in 25 ml of toluene. After addition of aqueous NH$_4$Cl solution and decantation, the organic phase is concentrated under vacuum, the residue is taken up with AcOEt, the organic phase is washed with saturated NaCl solution and dried over Na$_2$SO$_4$ and the solvent is evaporated off under vacuum. The residue is chromatographed on silica using a cyclohexane/AcOEt mixture (75/25 ; v/v) as the eluent to give 0.7 g of the expected product.

B) 1-[1-(4-Methylphenyl)ethyl]-5-(4-chloro-3-methylphenyl)pyrazole-3-carboxylic acid This compound is prepared by the procedure described in step B of Preparation 1.25 from 0.7 g of the compound obtained in the previous step in 15 ml of MeOH and a solution of 0.28 g of KOH in 15 ml of water. 0.63 g of the expected product is obtained.

Preparation 1.27

1-[1-(3,4-Dichlorophenyl)ethyl]-5-(4-chloro-3-methylphenyl)pyrazole-3-carboxylic acid A) Methyl 1-[1-(3,4-dichlorophenyl)ethyl]-5-(4-chloro-3-methyl phenyl)pyrazole-3 -carboxylate This compound is prepared by the procedure described in step A of Preparation 1.25 from 3 g of the compound obtained in step B of Preparation 1.10 in 25 ml of toluene, 1 g of a 60% dispersion of sodium hydride in oil and 3 g of 1-(1-bromoethyl)-3,4-dichlorobenzene (Preparation 3.6) in 25 ml of toluene. After addition of aqueous NH$_4$Cl solution and decantation, the organic phase is concentrated under vacuum, the residue is taken up with AcOEt, the organic phase is washed with saturated NaCl solution and dried over Na$_2$SO$_4$ and the solvent is evaporated off under vacuum. The residue is chromatographed on silica using a cyclohexane/AcOEt mixture (80/20; v/v) as the eluent to give 1.4 g of the expected product.

B) 1-[1-(3,4-Dichlorophenyl)ethyl]-5-(4-chloro-3-methylphenyl)pyrazole-3-carboxylic acid This compound is prepared by the procedure described in step B of Preparation 1.25. from 1 g of the compound obtained in the previous step in 20 ml of MeOH and a solution of 0.4 g of KOH in 20 ml of water. 0.96 g of the expected product is obtained.

NMR: δ (ppm): 1.8 : d : 3H; 2.35 : s : 3H; 5.7 : qd : 1H; 6.7 to 7.7 : u : 7H; 12.9 : bs : 1H.

An Overhauser effect (NOE) is observed between the benzyl proton (R$_4$=H) and the protons g$_2$=g$_6$=H.

Preparation 1.28

1-[1-(4-Methylphenyl)propyl]-5-(4-chloro-3-methylphenyl)pyrazole-3-carboxylic acid A) N,N'-Dipropylidenehydrazine 10 ml of water are added to 58 g of propionaldehyde cooled to 0° C. and 19.9 ml of hydrazine monohydrate are then added dropwise to the reaction mixture while maintaining the temperature below 10° C. 67.5 g of KOH pellets are then added in portions and the reaction mixture is left overnight at RT. After decantation, the organic phase is distilled off under reduced pressure to give 24.37 g of the expected product. B.p.=48° C. under 2400 Pa.

B) N-Propylidene-N'-[1-(4-methylphenyl)propyl] hydrazine 100 ml of a 1M p-tolylmagnesium bromide solution in ether are refluxed under a nitrogen atmosphere and a solution of 10 g of the compound obtained in the previous step in 40 ml of anhydrous ether is then added dropwise and the reaction mixture is stirred overnight at RT. It is cooled to 5° C. and saturated aqueous NH$_4$Cl solution is added. The mixture is decanted, the aqueous phase is extracted with ether, the combined organic phases are dried over MgSO$_4$ and the solvent is evaporated off under vacuum to give 6 g of the expected product. B.p.=102–103° C. under 20 Pa.

n$_D^{20}$=1.5180.

C) [1-(4-Methylphenyl)propyl]hydrazine oxalate

A solution of 6 g of the compound obtained in the previous step in 5 ml of ether is added to a solution of 4.78 g of oxalic acid in 20 ml of EtOH and 20 ml of ether and the reaction mixture is left overnight at 0–5° C. The crystallised product formed is filtered off and washed with ether to give 1.84 g of the expected product.

D) Methyl 1-[1-(4-methylphenyl)propyl]-5-(4-chloro-3-methylphenyl)pyrazole-3-carboxylate A solution of 1.84 g of the compound obtained in the previous step in 20 ml of water and 30 ml of EtOH is added at RT to a solution of 2 g of the compound obtained in step A of Preparation 1.10 in 100 ml of water and 100 ml of EtOH and the reaction mixture is stirred for 3 hours at RT. It is extracted with ether, the organic phase is dried over Na$_2$SO$_4$ and the solvent is evaporated off under vacuum. The residue is taken up with hexane, an insoluble material is filtered off and the filtrate is concentrated under vacuum. The residue is chromatographed on silica using a cyclohexane/AcOEt mixture (80/20; v/v) as the eluent to give 1.12 g of the expected product.

E) 1-[1-(4-Methylphenyl)propyl]-5-(4-chloro-3-methylphenyl)pyrazole-3-carboxylic acid A solution of 0.47 g of KOH in 10 ml of water is added at RT to a solution of 1.1 g of the compound obtained in the previous step in 40 ml of EtOH and the reaction mixture is then refluxed for 3 hours. It is concentrated under vacuum, the residue is taken up with 50 ml of water and acidified to pH 2 by the addition of 6N HCl solution, and the precipitate formed is filtered off, washed with water and dried to give 0.89 g of the expected product.

Preparation 1.29

1-[1-Methyl-1-(4-methylphenyl)ethyl]-5-(4-chloro-3-methylphenyl)pyrazole-3-carboxylic acid A) N,N'-Diisopropylidenehydrazine This compound is prepared by the procedure described in step A of Preparation 1.28 from 92 g of acetone, 20 ml of water, 39.7 ml of hydrazine monohydrate and 135 g of KOH. 66 g of the expected product are obtained ; b.p.=55° C. under 2100 Pa.

B) N-Isopropylidene-N'-[1-methyl-1-(4-methylphenyl)ethyl]hydrazine 100 ml of a 1M p-tolylmagnesium bromide solution in ether are refluxed under a nitrogen atmosphere and a solution of 8.46 g of the compound obtained in the previous step in 200 ml of anhydrous ether is then added dropwise and reflux is continued for 5 days. After cooling to 5° C., saturated aqueous $NH_4Cl$ solution is added, the reaction mixture is decanted, the aqueous phase is extracted with ether, the combined organic phases are dried over $Na_2SO_4$ and the solvent is evaporated off under vacuum. The residue is distilled off under reduced pressure to give 6.45 g of the expected product. B.p.=95° C. under 266.6 Pa.

C) [1-Methyl-1-(4-methylphenyl)ether]hydrazine oxalate

A solution of 6.45 g of the compound obtained in the previous step in 5 ml of ether is added to a solution of 5.12 g of oxalic acid in 24 ml of EtOH and 24 ml of ether and the reaction mixture is left overnight at RT. The crystallised product formed is filtered off and washed with hexane to give 2.57 g of the expected product.

D) Methyl 1-[1-methyl-1-(4-methylphenyl)ethyl]-5-(4-chloro-3-methylphenyl)pyrazole-3-carboxylate A solution of 2.54 g of the compound obtained in the previous step in 200 ml of water and 300 ml of EtOH is added at RT to a solution of 2.66 g of the compound obtained in step A of Preparation 1.10 in 600 ml of water and 1 liter of EtOH and the reaction mixture is stirred for 3 hours at RT and then left to stand for 24 hours. The precipitate formed is filtered off, washed with hexane and dried to give 3.46 g of the expected product.

E) 1-[1-Methyl-1-(4-methylphenyl)ethyl]-5-(4-chloro-3-methylphenyl)pyrazole-3-carboxylic acid A solution of 1.44 g of KOH in 20 ml of water is added at RT to a solution of 3.3 g of the compound obtained in the previous step in 80 ml of EtOH and the reaction mixture is then refluxed for 3 hours. An insoluble material is filtered off and the filtrate is concentrated to 20 ml. 30 ml of iced water and then 50 ml of DCM are added, the mixture is acidified to pH 3.5 by the addition of 1N HCl and decanted, the organic phase is dried over $Na_2SO_4$ and the solvent is evaporated off under vacuum to give 3.15 g of the expected product.

Preparation 1.30

1-(2,4-Dichlorobenzyl)-5-(4-chlorophenyl)-4-methylpyrazole-3-carboxylic acid

A) Lithium salt of ethyl 4-(4-chlorophenyl)-3-methyl-4-oxido-2-oxobut-3-enoate 154 ml of a 1M hexamethyldisilazane lithium salt solution in THF are added under a nitrogen atmosphere to 120 ml of cyclohexane cooled to 0° C. A solution of 21.6 g of 4'-chloropropiophenone in 60 ml of cyclohexane is then added dropwise over 30 minutes at 0° C. and the reaction mixture is stirred for 3 hours at RT. 21.4 g of diethyl oxalate are then added quickly while maintaining the temperature below 25° C. and the reaction mixture is stirred for 48 hours at RT. The precipitate formed is filtered off, washed with cyclohexane and dried to give 31.3 g of the expected product.

B) Ethyl 5-(4-chlorophenyl)-4-methylpyrazole-3-carboxylate 2.04 ml of hydrazine monohydrate are added dropwise at RT to a solution of 15 g of the compound obtained in the previous step in 100 ml of AcOH and the reaction mixture is then refluxed for 5 hours and stirred overnight at RT. It is poured into a water/ice mixture and the precipitate formed is filtered off, washed with water and then hexane and dried to give 11.47 g of the expected product.

C) Ethyl 1-(2,4-dichlorobenzyl)-5-(4-chlorophenyl)-4-methylpyrazole-3-carboxylate 0.72 g of a 60% dispersion of sodium hydride in oil is added in portions at RT to a solution of 2.17 g of the compound obtained in the previous step in 25 ml of toluene and the reaction mixture is then heated at 65° C. for 1 hour. After cooling to RT, a solution of 2.28 g of 2,4-dichlorobenzyl chloride in 25 ml of toluene is added dropwise and the reaction mixture is then refluxed for 20 hours. After cooling to RT, saturated aqueous $NH_4Cl$ solution is added, the mixture is decanted, the organic phase is washed with saturated NaCl solution and dried over $MgSO_4$ and the solvent is evaporated off under vacuum. The residue is extracted with AcOEt, the organic phase is washed with saturated $NaHCO_3$ solution, with a buffer solution of pH 2 and with water and dried over $MgSO_4$ and the solvent is evaporated off under vacuum. The residue is chromatographed on silica using a cyclohexane/AcOEt mixture (75/25; v/v) as the eluent to give 1.10 g of the expected product. M.p.=82° C.

NMR: δ (ppm): 1.2 : t : 3H; 2.0 : s : 3H; 4.2 : qd : 2H; 5.3 : s : 2H; 6.7 : d : 1H; 7.15 to 7.6 : u : 6H.

An Overhauser effect (NOE) is observed between the benzyl protons ($R_4=R_5=H$) and the protons $g_2=g_6=H$.

D) 1-(2,4-Dichlorobenzyl)-5-(4-chlorophenyl)-4-methylpyrazole-3-carboxylic acid

A solution of 0.166 g of KOH in 10 ml of water is added at RT to a solution of 0.8 g of the compound obtained in the previous step in 50 ml of EtOH and the reaction mixture is then refluxed for 4 hours. It is concentrated under vacuum, the residue is taken up with water, an insoluble material is filtered off, the filtrate is acidified to pH 2 by the addition of 6N HCl and the precipitate formed is filtered off, washed with water and dried to give 0.73 g of the expected product.

Preparation 1.31

1-(3,4-Dichlorobenzyl)-5-(4-chlorophenyl)-4-methylpyrazole-3-carboxylic acid

A) Ethyl 1-(3,4-dichlorobenzyl)-5-(4-chlorophenyl)-4-methylpyrazole-3-carboxylate This compound is prepared by the procedure described in step C of Preparation 1.30 from 2.17 g of the compound obtained in step B of Preparation 1.30 in 25 ml of toluene, 0.72 g of a 60% dispersion of sodium hydride in oil and 2.99 g of 3,4-dichlorobenzyl bromide in 25 ml of toluene. 1.87 g of the expected product are obtained; m.p.=117.5° C.

NMR: δ (ppm): 1.25 : t : 3H; 2.05 : s : 3H; 4.25 : qd : 2H; 5.3 : s : 2H; 6.8 : dd : 1H; 7.15 : s : 1H; 7.3 : d : 2H; 7.4 to 7.6 : u : 3H.

An Overhauser effect (NOE) is observed between the benzyl protons ($R_4=R_5=H$) and the protons $g_2=g_6=H$.

B) 1-(3,4-Dichlorobenzyl)-5-(4-chlorophenyl)-4-methylpyrazole-3-carboxylic acid

This compound is prepared by the procedure described in step D of Preparation 1.30 from 1.5 g of the compound obtained in the previous step in 50 ml of EtOH and 0.3 g of KOH in 10 ml of water. 1.31 g of the expected product are obtained.

Preparation 1.32

1-(3-Chloro-4-methylbenzyl)-5-(4-chlorophenyl)-4-methylpyrazole-3-carboxylic acid 0.72 g of a 60% dispersion of sodium hydride in oil is added in portions at RT to a solution of 2.17 g of the compound obtained in step B of Preparation 1.30 in 100 ml of toluene and the mixture is then heated at 65° C. for 1 hour. After cooling to RT, 2.2 g of 3-chloro-4-methylbenzyl iodide are added dropwise and the reaction mixture is then refluxed for 20 hours. After cooling to RT, saturated aqueous $NH_4Cl$ solution is added, the reaction mixture is decanted, the organic phase is washed with saturated NaCl solution and dried over MgSO$_4$ and the solvent is evaporated off under vacuum. The residue is extracted with AcOEt, the organic phase is washed with saturated NaHCO$_3$ solution, with a buffer solution of pH 2 and with water and dried over MgSO$_4$ and the solvent is evaporated off under vacuum. The residue is taken up with a cyclohexane/AcOEt mixture (75/25; v/v) and the precipitate is filtered off to give 1.38 g of crude product. It is dissolved in AcOEt, cyclohexane is added until a precipitate forms and the precipitate is filtered off to give 0.17 g of the purified expected product. M.p.= 162° C.

NMR: δ (ppm): 1.95 to 2.6 : u : 6H; 5.2 : s: 2H ; 6.6 to 7.7 : u : 7H 12.85 : bs : 1H.

An Overhauser effect (NOE) is observed between the benzyl protons (R$_4$=R$_5$=H) and the protons g$_2$=g$_6$=H.

Preparation 1.33

1-(4-Methylbenzyl)-5-(4-chloro-3-methylphenyl)-4-methylpyrazole-3-carboxylic acid A) 4'-chloro-3'-methylpropiophenone 16 g of propionyl chloride are added dropwise to a mixture of 18 ml of o-chlorotoluene and 22.7 g of aluminum chloride and the reaction mixture is then heated at 130° C. for 3 hours. After cooling to RT, it is poured into a mixture of 100 ml of concentrated HCl and ice, extracted with ether, the organic phase is washed with saturated NaHCO$_3$ solution and dried over Na$_2$SO$_4$ and the solvent is evaporated off under vacuum. The residue is distilled off under reduced pressure to give 20.7 g of the expected product which crystallizes. B.p.=95° C. under 5 Pa.

B) Lithium salt of ethyl 4-(4-chloro-3-methylphenyl)-3-methyl-4-oxido-2-oxobut-3-enoate This compound is prepared by the procedure described in step A of Preparation 1.30 from 50 ml of a 1M hexamethyl disilazane lithium salt solution in THF, 40 ml of cyclohexane, 10 g of the compound obtained in the previous step in 70 ml of cyclohexane and 9.8 g of diethyl oxalate. After stirring overnight at RT, the reaction mixture is concentrated under vacuum, the residue is taken up with ether and the solvent is evaporated off under vacuum. The residue is taken up with heptane and the precipitate formed is filtered off to give 15 g of the expected product.

C) Ethyl 5-(4-chloro-3-methylphenyl)-4-methylpyrazole-3-carboxylate 2.5 ml of hydrazine monohydrate are added dropwise to a solution of 15 g of the compound obtained in the previous step in 150 ml of AcOH cooled to 5° C. and the reaction mixture is then refluxed for 5 hours and stirred overnight at RT. It is poured into a water/ice mixture, extracted with AcOEt, the organic phase is washed three times with saturated NaCl solution and dried over Na$_2$SO$_4$ and the solvent is evaporated off under vacuum. The residue is taken up with iso ether and the precipitate formed is filtered off, washed with iso ether and dried to give 7.88 g of the expected product.

D) Ethyl 1-(4-methylbenzyl)-5-(4-chloro-3-methylphenyl)-4-methylpyrazole-3-carboxylate 0.98 g of a 60% dispersion of sodium hydride in oil is added in portions at RT to a suspension of 5 g of the compound obtained in the previous step in 70 ml of toluene and the reaction mixture is then heated at 65° C. for 1 hour. After cooling to RT, 3.7 g of 4-methylbenzyl bromide are added dropwise and the reaction mixture is then refluxed overnight. After cooling to RT, 50% aqueous NH$_4$Cl solution is added and the organic phase is decanted and concentrated under vacuum. The residue is extracted with AcOEt, the organic phase is washed twice with saturated NaCl solution and dried over Na$_2$SO$_4$ and the solvent is evaporated off under vacuum. The residue is chromatographed on silica using a cyclohexane/AcOEt mixture (80/20; v/v) as the eluent to give 2.1 g of the expected product.

E) 1-(4-Methylbenzyl)-5-(4-chloro-3-methylphenyl)-4-methylpyrazole-3-carboxylic acid A solution of 0.439 g of KOH in 20 ml of water is added at RT to a solution of 2 g of the compound obtained in the previous step in 20 ml of EtOH and the reaction mixture is then refluxed for 3 hours. After cooling to RT, it is poured into a 1N HCl/ice mixture and the precipitate formed is filtered off, washed with water and dried under vacuum to give 1.8 g of the expected product.

NMR: δ (ppm): 2 to 2.4 : u : 9H; 5.2 : s : 2H; 6.7 to 7.6 : u : 7H; 12.65 : bs : 1H.

Preparation 1.34

1-(3,4-Dichlorobenzyl)-5-(4-chloro-3-methylphenyl)-4-methylpyrazole-3-carboxylic acid A) Ethyl 1-(3,4-dichlorobenzyl)-5-(4-chloro-3-methylphenyl)-4-methylpyrazole-3-carboxylate This compound is prepared by the procedure described in step D of Preparation 1.33 from 2.5 g of the compound obtained in step C of Preparation 1.33 in 50 ml of toluene, 0.8 g of a 60% dispersion of sodium hydride in oil and 2.4 g of 3,4-dichlorobenzyl bromide. After hydrolysis by the addition of 50% aqueous NH$_4$Cl solution, the organic phase is decanted, an insoluble material is filtered off and the filtrate is concentrated under vacuum. The residue is extracted with AcOEt, the organic phase is washed twice with saturated NaCl solution and dried over Na$_2$SO$_4$ and the solvent is evaporated off under vacuum. The residue is chromatographed on silica using a cyclohexane/AcOEt mixture (80/20; v/v) as the eluent to give 3 g of the expected product.

B) 1-(3,4-Dichlorobenzyl)-5-(4-chloro-3-methylphenyl)-4-methylpyrazole-3-carboxylic acid This compound is prepared by the procedure described in step E of Preparation 1.33 from 3 g of the compound obtained in the previous step in 20 ml of EtOH and 0.56 g of KOH in 20 ml of water. 2.7 g of the expected product are obtained.

NMR: δ (ppm) 2 : s : 3H; 2.3 : u : 3H; 5.2 : s : 2H; 6.7 to 7.6 : u : 6H; 12.65 : bs : 1H.

Preparation 1.35

1-(4-Chloro-3-methylbenzyl)-5-(4-chlorophenyl)-4-(ethoxymethyl) pyrazole-3-carboxylic acid A) Ethyl 1-(tert-butoxycarbonyl)-5-(4-chlorophenyl)-4-methylpyrazole-3-carboxylate 4.62 ml of triethylamine, 6.57 g of di-tert-butyldicarbonate and 1.18 g of a 60% dispersion of sodium hydride in oil are added to a solution of 6 g of the compound obtained in step B of Preparation 1.30 in 150 ml of dioxane and the reaction mixture is then stirred for 72 hours at RT. An insoluble material is filtered off and the filtrate is concentrated under vacuum. The residue is taken up with cyclohexane and the precipitate formed is filtered off, washed with cyclohexane and dried to give 6.23 g of the expected product.

B) Ethyl 1-(tert-butoxycarbonyl)-5-(4-chlorophenyl)-4-(bromomethyl)pyrazole-3-carboxylate 3.18 g of N-bromosuccinimide and 0.02 g of dibenzoyl peroxide are added to a solution of 6.2 g of the compound obtained in the previous step in 150 ml of CCl$_4$ and the reaction mixture is then refluxed overnight. An insoluble material is filtered off and the filtrate is concentrated under vacuum. The residue is taken up with cyclohexane, the mixture is decanted and the solvent is evaporated off under vacuum to give 8.72 g of the expected product in the form of an oil.

C) Ethyl 5-(4-chlorophenyl)-4-(ethoxymethyl)pyrazole-3-carboxylate 0.23 g of sodium are dissolved in 100 ml of EtOH and 4.5 g of the compound obtained in the previous step are then added dropwise and the reaction mixture is refluxed overnight. It is concentrated under vacuum and the residue is chromatographed on silica using a cyclohexane/AcOEt mixture (60/40; v/v) as the eluent to give 2.26 g of the expected product.

D) Ethyl 1-(3-chloro-4-methylbenzyl)-5-(4-chlorophenyl)-4-(ethoxymethyl)pyrazole-3-carboxylate 0.254 g of a 60% dispersion of sodium hydride in oil is added in portions at RT to a solution of 1.65 g of the compound obtained in the previous step in 50 ml of toluene and the reaction mixture is then heated at 65° C. for 1 hour. After cooling to RT, 1.7 g of 3-chloro-4-methylbenzyl iodide are added dropwise and the reaction mixture is then refluxed for 20 hours. After cooling to RT, an insoluble material is filtered off and the filtrate is concentrated under vacuum. The residue is extracted with AcOEt, the organic phase is washed with saturated $NH_4Cl$ solution, with a buffer solution of pH 2 and with water and dried over $MgSO_4$ and the solvent is evaporated off under vacuum. The residue is chromatographed on silica using a cyclohexane/AcOEt mixture (75/25; v/v) as the eluent. 0.90 g of product is obtained which is rechromatographed on silica using a cyclohexane/AcOEt mixture (80/20; v/v) as the eluent to give 0.24 g of the expected product.

E) 1-(4-Chloro-3-methylbenzyl)-5-(4-chlorophenyl)-4-(ethoxymethyl) pyrazole-3-carboxylic acid A solution of 0.088 g of KOH in 10 ml of water is added at RT to a solution of 0.23 g of the compound obtained in the previous step in 10 ml of EtOH and the reaction mixture is then refluxed for 3 hours. It is concentrated under vacuum to a volume of 10 ml, 10 ml of water are added, the mixture is acidified to pH 2.5 by the addition of 1N HCl solution and the precipitate formed is filtered off and dried to give 0.21 g of the expected product.

Preparation 1.36

1-(5-Chloroindan-1-yl)-5-(4-chlorophenyl)pyrazole-3-carboxylic acid.

0.88 g of a 60% dispersion of sodium hydride in oil is added in portions to a suspension of 2.5 g of the compound obtained in step B of Preparation 1.7 in 20 ml of toluene and the reaction mixture is then heated at 65° C. for 1 hour. After cooling to RT, a solution of 2.3 g of 1-bromo-5-chloroindane (Preparation 3.8) in 10 ml of toluene is added dropwise and the reaction mixture is refluxed overnight. It is cooled to 5° C., 20 ml of 50% aqueous $NH_4Cl$ solution are added dropwise and the organic phase is decanted and concentrated under vacuum. The residue is extracted with AcOEt, the organic phase is washed with saturated NaCl solution and dried over $Na_2SO_4$ and the solvent is evaporated off under vacuum to give 1.04 g of the expected product which is used as such.

Preparation 1.37

1-(4-Methoxybenzyl)-5-(4-chloro-3-methylphenyl)pyrazole-3-carboxylic acid

A) Methyl 1-(4-methoxybenzyl)-5-(4-chloro-3-methylphenyl)pyrazole-3-carboxylate 0.53 g of a 60% dispersion of sodium hydride in oil is added in portions at RT to a suspension of 2.5 g of the compound obtained in step B of Preparation 1.10 in 25 ml of toluene and the reaction mixture is then heated at 65° C. for 1 hour. After cooling to RT, a solution of 1.7 g of 4-methoxybenzyl chloride in 25 ml of toluene is added-dropwise and the reaction mixture is then refluxed for 20 hours. After cooling to RT, 20 ml of 50% aqueous $NH_4Cl$ solution are added and the organic phase is decanted and evaporated off under vacuum. The residue is extracted with AcOEt, the organic phase is washed with saturated NaCl solution and dried over $MgSO_4$ and the solvent is evaporated off under vacuum. The residue is chromatographed on silica using a cyclohexane/AcOEt mixture (80/20; v/v) as the eluent to give 1.03 g of the expected product which is used as such.

B) 1-(4-Methoxybenzyl)-5-(4-chloro-3-methylphenyl)pyrazole-3-carboxylic acid

A solution of 0.23 g of KOH in 20 ml of water is added at RT to a solution of 1.03 g of the compound obtained in the previous step in 20 ml of MeOH and the reaction mixture is then refluxed for 3 hours. After cooling to RT, it is poured into a 1N HCl/ice mixture, extracted with ether and the organic phase is dried over $Na_2SO_4$ and the solvent is evaporated off under vacuum to give 0.8 g of the expected product which is used as such.

Preparation 1.38

1-(2,4-Dichlorobenzyl)-3-(4-chlorophenyl)pyrazole-5-carboxylic acid

A) Methyl 1-(2,4-dichlorobenzyl)-3-(4-chlorophenyl)pyrazole-5-carboxylate 0.16 g of a 60% dispersion of sodium hydride in oil is added in portions at RT to a solution of 0.8 g of the compound obtained in step B of Preparation 1.7 in 15 ml of DMF and the reaction mixture is stirred for 30 minutes at RT. It is cooled to 0° C., a solution of 0.49 ml of 2,4-dichlorobenzyl in 5 ml of DMF is added dropwise and the reaction mixture is then stirred for 16 hours at RT. It is poured into iced water, the aqueous phase is washed with DCM and the white precipitate is filtered off, washed with water and dried to give 0.86 g of the expected product. M.p.=120° C.

B) 1-(2,4-Dichlorobenzyl)-3-(4-chlorophenyl)pyrazole-5-carboxylic acid

A solution of 0.3 g of KOH in 5 ml of water is added to a solution of 0.85 g of the compound obtained in the previous step in 15 ml of MeOH and the reaction mixture is then refluxed for 3 hours. It is poured into 100 ml of iced water and the precipitate formed is filtered off, washed with water and dried under vacuum to give 0.79 g of the expected product. M.p. 218° C.

Preparation 2.1

(1S)-2endo-Amino-1,3,3-trimethylbicyclo[2.2.1]heptane hydrochloride

A) (1S)-1,3,3-Trimethylbicyclo[2.2.1]heptan-2-one oxime

A solution of 23 g of hydroxylamine hydrochloride and 41 g of sodium acetate in 200 ml of water is added at RT to a solution of 38.1 g of (1S)-(+)-fenchone in 120 ml of MeOH and the mixture is then refluxed for 48 hours. After cooling to RT, the precipitate formed is filtered off, washed with water and dried under vacuum to give 41 g of the expected product.

B) (1S)-2endo-Amino-1,3,3-trimethylbicyclo[2.2.1]heptane hydrochloride

A mixture of 8 g of the compound obtained in the previous step and 0.8 g of platinum oxide in 700 ml of EtOH and 20 ml of chloroform is hydrogenated in a Parr apparatus for 48 hours at RT and under a pressure of 6 bar. The catalyst is filtered off on Célite® and the filtrate is concentrated under vacuum. The residue is taken up with ether and the precipitate formed is filtered off to give 2.61 g of the expected product.

$[\alpha]_D^{20}=-4.6°$ (c=1; EtOH)

Preparation 2.2

(1S)-2endo,exo-Amino-1,3,3-trimethylbicyclo[2.2.1] heptane

A solution of 10 g of the compound obtained in step A of Preparation 2.1 in 70 ml of AcOH is cooled to 10° C., 25 g of Raney® nickel are added and the temperature of the mixture is allowed to return to RT. The mixture is then hydrogenated for 24 hours at RT and at atmospheric pressure. The catalyst is filtered off on Célite®, a mixture of 100 ml of water and ice is added to the filtrate, the pH is brought to 7 by the addition of concentrated NaOH solution, the mixture is extracted with ether, the organic phase is dried over MgSO₄ and the solvent is evaporated off under vacuum to give 7.37 g of the expected product (endo, exo mixture) in the form of an oil.

Preparation 2.3

(1R)-2endo,exo-Amino-1,3,3-trimethylbicyclo[2.2.1] heptane and (1R)-2-imino-1,3,3-trimethylbicyclo[2.2.1] heptane A) (1R)-1,3,3-Trimethylbicyclo[2.2.1]heptan-2-one oxime This compound is prepared by the procedure described in step A of Preparation 2.1 from (1R)-(−)-fenchone.

B) (1R)-2endo,exo-Amino-1,3,3-trimethylbicyclo[2.2.1] heptane and (1R)-2-imino-1,3,3-trimethylbicyclo[2.2.1] heptane A solution of 14 g of the compound obtained in the previous step in 100 ml of AcOH is cooled to 100° C., 35 g of Raney® nickel are added and the temperature of the mixture is allowed to return to RT. The mixture is then hydrogenated for 24 hours at RT and at atmospheric pressure. The catalyst is filtered off on Célite®, a mixture of 100 ml of water and ice is added to the filtrate, the pH is brought to 7 by the addition of concentrated NaOH solution, the mixture is extracted with ether, the organic phase is dried over MgSO₄ and the solvent is evaporated off under vacuum to give 10.77 g of a mixture of the expected products.

Preparation 2.4

2exo-(Propylamino)bicyclo[2.2.1]heptane hydrochloride

A) 2exo-(Propionylamino)bicyclo[2.2.1]heptane

A solution of 15 g of 2exo-aminonorbornane and 20.5 ml of triethylamine in 80 ml of DCM is cooled in an ice bath, a solution of 11.2 ml of propionyl chloride in 80 ml of DCM is added dropwise and the reaction mixture is stirred overnight at RT. After filtration, the filtrate is washed with saturated aqueous NaHCO₃ solution and with water, the organic phase is dried over MgSO₄ and the solvent is evaporated off under vacuum to give 23 g of the expected product.

B) 2exo-(Propylamino)bicyclo[2.2.1]heptane hydrochloride

A solution of 23 g of the compound obtained in the previous step in 100 ml of THF is added dropwise to a suspension of 7.6 g of lithium aluminum hydride in 100 ml of THF and the reaction mixture is then refluxed for 2 hours and stirred overnight at RT. It is hydrolyzed by the addition of 10 ml of water, followed by 5 ml of 15% NaOH solution and 14 ml of water. After stirring for 15 minutes, the inorganic salts are filtered off and the filtrate is concentrated under vacuum. The oil obtained is taken up with iso ether, a saturated solution of hydrochloric acid in ether is added until the pH is 1, and the precipitate formed is filtered off. It is taken up with AcOEt and extracted with water, the aqueous phase is rendered alkaline to pH 12 by the addition of 5 N NaOH solution and extracted with AcOEt, the organic phase is washed with water and dried over MgSO₄ and the solvent is evaporated off under vacuum. The product obtained is taken up with iso ether, a saturated solution of hydrochloric acid in ether is added until the pH is 1, and the precipitate formed is filtered off to give 14 g of the expected product. M.p.=230° C. (dec.).

Preparation 2.5

3endo-Aminobicyclo[3.2.1]octane hydrochloride

This compound is prepared by the procedure described by H. Maskill et al., J. Chem. Soc. Perkin Trans. II, 1984, 1369–1376.

Preparation 2.6

(1R)-2endo-Amino-1,3,3-trimethylbicyclo[2.2.1]heptane hydrochloride

A mixture of 15.5 g of the compound obtained in step A of Preparation 2.3 and 2 g of platinum oxide in 500 ml of EtOH and 14 ml of chloroform is hydrogenated in a Parr apparatus at RT and under a pressure of 8 bar. The catalyst is filtered off on Célite® and the filtrate is concentrated under vacuum. The residue is taken up with a saturated solution of hydrochloric acid in ether and the solvent is evaporated off under vacuum. The residue is taken up with hexane, an insoluble material is filtered off and the solvent is evaporated off under vacuum to give 5.64 g of an oil which crystallises in time. The crystals formed are filtered off, they are taken up with hexane, filtered off again and washed to give 0.85 g of the expected product.

$\alpha_D^{20}=+1°$ (c=1; EtOH)

Preparation 2.7

2,2,6,6-Tetramethylcyclohexylamine

A) 2,2,6,6-Tetramethylcyclohexanone-oxime

A solution of 2.3 g of hydroxylamine hydrochloride and 3.6 g of sodium acetate in 20 ml of water is added at RT to a solution of 3.4 g of 2,2,6,6-tetramethylcyclohexanone in 20 ml of MeOH and the reaction mixture is then refluxed for 48 hours. After cooling to RT, the precipitate formed is filtered off, washed with water and dried under vacuum to give 1.2 g of the expected product.

B) 2,2,6,6-Tetramethylcyclohexylamine

A solution of 1 g of the compound obtained in the previous step in 30 ml of AcOH is cooled to 0° C. under a nitrogen atmosphere, 2.5 g of Raney® nickel are added and the temperature of the mixture is allowed to rise to RT. The mixture thus obtained is hydrogenated for 24 hours and RT and under atmospheric pressure. The catalyst is filtered off on Célite®, a mixture water/ice is added to the filtrate, the pH is brought to 7 by the addition of concentrated NaOH solution, the mixture is extracted with AcOEt, the organic phase is dried over Na₂SO₄ and the solvent is evaporated off under vacuum to give 0.63 g of the expected product.

Preparation 3.1

3-Fluoro-4-methylbenzyl bromide

A) Ethyl 3-fluoro-4-methylbenzoate 150 ml of EtOH are cooled in an ice bath, 10 ml of thionyl chloride are added slowly, 10 g of 3-fluoro-4-methylbenzoic acid are then added and the reaction mixture is stirred, the temperature being allowed to rise to RT. It is refluxed for 2 hours and then concentrated under vacuum to give 10.45 g of the expected product in the form of an oil.

B) 3-Fluoro-4-methylbenzyl alcohol

A suspension of 3.26 g of lithium aluminum hydride in 100 ml of THF is cooled to 0° C., a solution of 10.45 g of the compound obtained in the previous step in 50 ml of THF is added dropwise and the reaction mixture is stirred until the temperature has risen to RT. It is then refluxed for 3 hours; a further 1.5 g of lithium aluminum hydride are added and reflux is continued for 48 hours. After cooling to RT, the reaction mixture is hydrolyzed by the addition of saturated aqueous $NH_4Cl$ solution and the organic phase is then decanted and retained. The aqueous phase is extracted with THF, the combined organic phases are then dried over $MgSO_4$ and the solvent is evaporated off under vacuum to give 7.87 g of the expected product in the form of an oil.

C) 3-Fluoro-4-methylbenzyl bromide

A mixture of 7.8 g of the compound obtained in the previous step and 112 ml of 47% aqueous HBr solution is heated at 100° C. for 2 hours. After cooling to RT, the reaction mixture is extracted with ether, the organic phase is dried over $MgSO_4$ and the solvent is evaporated off under vacuum to give 11.15 g of the expected product in the form of an oil, which is used as such.

Preparation 3.2

3-Chloro-4-methylbenzyl iodide

A solution of 8.5 g of sodium iodide in 25 ml of acetone is added dropwise at RT to a solution of 9.6 g of 3-chloro-4-methylbenzyl chloride in 15 ml of acetone and the mixture is stirred for 48 hours at RT. The sodium chloride formed is filtered off, the filtrate is dried over $Na_2SO_4$ and the solvent is evaporated off under vacuum to give 13 g of the expected product in the form of an oil, which is used as such.

Preparation 3.3

3-Chloro-4-fluorobenzyl bromide 0.05 g of dibenzoyl peroxide and then 6.1 g of N-bromosuccinimide are added to a mixture of 5 g of 3-chloro-4-fluorotoluene and 100 ml of $CCl_4$ and the reaction mixture is refluxed for 12 hours. The insoluble material is filtered off and washed with $CCl_4$. The filtrate is washed with water and with saturated NaCl solution, the organic phase is dried over $Na_2SO_4$ and the solvent is evaporated off under vacuum to give 7.5 g of the expected product in the form of an oil, which is used as such.

Preparation 3.4

1-(1-Bromoethyl)-2,4-dichlorobenzene 15 ml of a 33% solution of HBr in AcOH are cooled to 0° C., 2 ml of 2,4-dichloro-1-(1-hydroxyethyl)benzene are added dropwise and the reaction mixture is stirred for 30 minutes at 0° C. and then for 3 hours at RT. It is poured into iced water and extracted with AcOEt, the organic phase is washed with saturated aqueous $NaHCO_3$ solution, with water and with saturated NaCl solution and dried over $MgSO_4$ and the solvent is evaporated off under vacuum to give 3.4 g of the expected product.

Preparation 3.5

4-Ethylbenzyl bromide 35 ml of a 33% solution of HBr in AcOH are cooled to 0° C., 5 g of 4-ethylbenzyl alcohol are added dropwise and the reaction mixture is stirred for 30 minutes at 0° C. and then overnight at RT. It is poured into 200 ml of iced water, the mixture is extracted with AcOEt, the organic phase is washed with saturated aqueous $NaHCO_3$ solution and with saturated NaCl solution, dried over $Na_2SO_4$ and the solvent is evaporated off under vacuum to give 5.6 g of the expected product.

Preparation 3.6

1-(1-Bromoethyl)-3,4-dichlorobenzene

This compound is prepared by the procedure described in Preparation 3.4 from 25 ml of a 33% solution of HBr in AcOH and 5 g of 3,4-dichloro-1-(1-hydroxyethyl)benzene. 6.4 g of the expected product are obtained.

Preparation 3.7

1-(1-Bromoethyl)-4-methylbenzene

This compound is prepared by the procedure described in Preparation 3.4 from 30 ml of a 33% solution of HBr in AcOH and 7 ml of 1-(1-hydroxyethyl)-4-methylbenzene. 9 g of the expected product are obtained.

Preparation 3.8

1-Bromo-5-chloroindane

A) 1-Hydroxy-5-chloroindane

A mixture of 2.5 g of 5-chloroindan-1-one and 30 ml of THF is cooled to 0–5° C., 2.5 ml of concentrated NaOH solution and then, in portions, 0.88 g of sodium borohydride are added and the reaction mixture is stirred overnight at RT. It is poured into 100 ml of water, the mixture is acidified to pH 2 by the addition of concentrated HCl solution, extracted with AcOEt, the organic phase is washed with saturated NaCl solution and dried over $Na_2SO_4$ and the solvent is evaporated off under vacuum. The residue is chromatographed on silica using a cyclohexane/AcOEt mixture (80/20; v/v) to give 2.1 g of the expected product.

B) 1-Bromo-5-chloroindane 12 ml of a 33% solution of HBr in AcOH are cooled to 0° C., 2 g of the compound obtained in the previous step are added dropwise and the reaction mixture is stirred for 30 minutes at 0° C. and then for 3 hours at RT. It is poured into 200 ml of iced water, the mixture is extracted with AcOEt, the organic phase is washed with saturated $NaHCO_3$ solution, with saturated NaCl solution and dried over $Na_2SO_4$ and the solvent is evaporated off under vacuum to give 2.8 g of the expected product.

EXAMPLE 1

N-[(1S)-1,3,3-Trimethylbicyclo[2.2.1]hept-2endo-yl]-1-(3,4-dichlorobenzyl)-5-(4-methylphenyl)pyrazole-3-carboxamide A) 1-(3,4-Dichlorobenzyl)-5-(4-methylphenyl)pyrazole-3-carboxylic acid chloride 1.52 ml of thionyl chloride are added at RT to a solution of 5.1 g of the compound obtained in Preparation 1.1 in 50 ml of toluene and the reaction mixture is then refluxed for 4 hours and stirred overnight at RT. It is concentrated under vacuum, the residue is taken up with ether and the solvent is evaporated off under vacuum to give 5.17 g of the expected product in the form of an oil.

B) N-[(1S)-1,3,3-Trimethylbicyclo[2.2.1]hept-2endo-yl]-1-(3,4-dichlorobenzyl)-5-(4-methylphenyl)pyrazole-3-carboxamide 0.759 g of the compound obtained in the previous step is added at RT to a solution of 0.38 g of the compound obtained in Preparation 2.1 and 0.554 ml of triethylamine in 50 ml of DCM and the reaction mixture is stirred overnight at RT. It is concentrated under vacuum, the residue is extracted with AcOEt, the organic phase is washed with saturated aqueous $NaHCO_3$ solution, with a buffer solution of pH 2 and with water and dried over $MgSO_4$ and the solvent is evaporated off under vacuum. The residue is taken up with hexane and the precipitate formed is filtered off and dried to give 0.67 g of the expected product. M.p.=137° C.

$[\alpha]_D^{20} = +1°$ (c=1; EtOH)

EXAMPLE 2

N-[(1S)-1,3,3-Trimethylbicyclo[2.2.1]hept-2exo-yl]-1-(3,4-dichlorobenzyl)-5-(4-methylphenyl)pyrazole-3-carboxamide 1 g of the compound obtained in step A of EXAMPLE 1 is added at RT to a solution of 0.5 g of the compound obtained in Preparation 2.2 and 0.364 ml of triethylamine in 50 ml of DCM and the reaction mixture is stirred overnight at RT. It is concentrated under vacuum, the residue is extracted with AcOEt, the organic phase is washed with saturated aqueous NaHCO$_3$ solution, with a buffer solution of pH 2 and with water and dried over MgSO$_4$ and the solvent is evaporated off under vacuum. The residue is chromatographed on silica using a cyclohexane/AcOEt mixture (75/25; v/v) as the eluent. The following two isomers are separated:

the less polar isomer: compound of EXAMPLE 1;

the more polar isomer: 0.08 g of the expected compound; m.p.=101° C.

NMR: δ (ppm): 0.6 to 2 : u : 16H; 2.3 : s : 3H; 3.45 : d : 1H; 5.4 : s : 2H; 6.8 : s : 1H; 6.9 : dd : 1H; 7.1 to 7.4 : u : 6H; 7.5 d : 1H

EXAMPLE 3 and EXAMPLE 4

N-[(1R)-1,3,3-Trimethylbicyclo[2.2.1]hept-2endo-yl]-1-(3,4-dichlorobenzyl)-5-(4-methylphenyl)pyrazole-3-carboxamide (Example 3) and N-[(1R)-1,3,3-trimethylbicyclo[2.2.1]hept-2exo-yl]-1-(3,4-dichlorobenzyl)-5-(4-methylphenyl)pyrazole-3-carboxamide (Example 4)

1 g of the compound obtained in step A of EXAMPLE 1 is added at RT to a solution of 0.5 g of the mixture of compounds obtained in Preparation 2.3 and 0.364 g of triethylamine in 50 ml of DCM and the reaction mixture is stirred overnight at RT. It is concentrated under vacuum, the residue is extracted with AcOEt, the organic phase is washed with saturated aqueous NaHCO$_3$ solution, with a buffer solution of pH 2 and with water and dried over MgSO$_4$ and the solvent is evaporated off under vacuum. The residue is chromatographed on silica using a cyclohexane/AcOEt mixture (75/25; v/v) as the eluent. The following different compounds are separated:

the least polar compound: 0.07 g of the compound of EXAMPLE 3; m.p.=130° C.

NMR: δ (ppm): 0.6 to 1.9 : u : 16H; 2.3 : s : 3H; 3.65 : d : 1H; 5.4 : s : 2H; 6.85 : s : 1H; 6.9 : dd : 1H; 7.0 : d : 1H; 7.15 to 7.4 : u : 5H; 7.5 : d : 1H 0.09 g of the compound of EXAMPLE 4; m.p.=121° C.

NMR: δ (ppm): 0.6 to 2 : u : 16H; 2.3 : s : 3H; 3.4 : d : 1H; 5.4 : s : 2H; 6.8 : s : 1H; 6.9 : dd : 1H; 7.1 to 7.4 : u : 5H; 7.5 : d : 1H and the most polar compound: 0.54 g of N-[(1R)-1,3,3-trimethylbicyclo[2.2.1]hept-2-ylidene]-1-(3,4-dichlorobenzyl)-5-(4-methylphenyl)pyrazole-3-carboxamide.

EXAMPLE 5

N-[Bicyclo[2.2.1]hept-2exo-yl]-N-propyl-1-(3,4-dichlorobenzyl)-5-(4-methylphenyl)pyrazole-3-carboxamide 0.66 g of the compound obtained in step A of EXAMPLE 1 is added at RT to a solution of 0.266 g of the compound obtained in Preparation 2.4 and 0.48 ml of triethylamine in 50 ml of DCM and the reaction mixture is stirred overnight at RT. It is concentrated under vacuum, the residue is extracted with AcOEt, the organic phase is washed with saturated aqueous NaHCO$_3$ solution, with a buffer solution of pH 2 and with water and dried over MgSO$_4$ and the solvent is evaporated off under vacuum. The residue is chromatographed on silica using a cyclohexane/AcOEt mixture (70/30; v/v) as the eluent to give 0.5 g of the expected product. M.p.=108° C.

EXAMPLE 6

N-[(1S)-1,3,3-Trimethylbicyclo[2.2.1]hept-2endo-yl]-1-(3-fluoro-4-methylbenzyl)-5-(4-methylphenyl)pyrazole-3-carboxamide A) 1-(3-Fluoro-4-methylbenzyl)-5-(4-methylphenyl)pyrazole-3-carboxylic acid chloride and 1-(3-fluoro-4-methylbenzyl)-3-(4-methylphenyl)pyrazole-5-carboxylic acid chloride 0.3 ml of thionyl chloride is added at RT to a solution of 0.9 g of the mixture of compounds obtained in Preparation 1.3 in 50 ml of toluene and the reaction mixture is then refluxed for 5 hours and stirred overnight at RT. It is concentrated under vacuum, the residue is taken up with ether and the solvent is evaporated off under vacuum to give 1 g of a mixture of the expected products.

B) N-[(1S)-1,3,3-Trimethylbicyclo[2.2.1]hept-2endo-yl]-1-(3-fluoro-4-methylbenzyl)-5-(4-methylphenyl)pyrazole-3-carboxamide 0.63 g of the mixture of compounds obtained in the previous step is added at RT to a solution of 0.33 g of the compound obtained in Preparation 2.1 and 0.48 ml of triethylamine in 50 ml of DCM and the reaction mixture is stirred for 48 hours at RT. It is concentrated under vacuum, the residue is extracted with AcOEt, the organic phase is washed with saturated aqueous NaHCO$_3$ solution, with a buffer solution of pH 2 and with water and dried over MgSO$_4$ and the solvent is evaporated off under vacuum. The residue is chromatographed on silica using a cyclohexane/AcOEt mixture (75/25; v/v) as the eluent. The following two compounds are separated:

the less polar compound: 0.5 g of the compound of EXAMPLE 6; m.p.=53° C.

$[\alpha]_D^{20}$=−3.3° (c=1; EtOH)

the more polar compound: N-[(1S)-1,3,3-trimethylbicyclo[2.2.1]hept-2endo-yl]-1-(3-fluoro-4-methylbenzyl)-3-(4-methylphenyl)pyrazole-5-carboxamide

EXAMPLE 7

N-[(1S)-1,3,3-Trimethylbicyclo[2.2.1]hept-2endo-yl]-1-(3-chloro-4-methylbenzyl)-5-(4-methoxyphenyl)pyrazole-3-carboxamide A) 1-(3-Chloro-4-methylbenzyl)-5-(4-methoxyphenyl)pyrazole-3-carboxylic acid chloride and 1-(3-chloro-4-methylbenzyl)-3-(4-methoxyphenyl)pyrazole-5-carboxylic acid chloride A mixture of these two compounds is prepared by the procedure described in step A of EXAMPLE 6 from 1.7 g of the mixture of compounds obtained in Preparation 1.5, 0.54 ml of thionyl chloride and 50 ml of toluene. 1.77 g of a mixture of the expected products are obtained.

B) N-[(1S)-1,3,3-Trimethylbicyclo[2.2.1]hept-2endo-yl]-1-(3-chloro-4-methylbenzyl)-5-(4-methoxyphenyl)pyrazole-3-carboxamide This compound is prepared by the procedure described in step B of EXAMPLE 6 from 0.531 g of the compound obtained in Preparation 2.1, 0.775 ml of triethylamine, 100 ml of DCM and 1 g of the mixture of compounds obtained in the previous step. The product is chromatographed on silica using a cyclohexane/AcOEt mixture (75/25; v/v) as the eluent. The following two compounds are separated:

the less polar compound: 0.77 g of the compound of EXAMPLE 7; m.p.=116° C.

$[\alpha]_D^{20}$=−1.1° (c=1; EtOH)

the more polar compound: N-[(1S)-1,3,3-trimethylbicyclo[2.2.1]hept-2endo-yl]-1-(3-chloro-4-methylbenzyl)-3-(4-methoxyphenyl)pyrazole-5-carboxamide

EXAMPLE 8

N-(Adamant-2-yl)-1-(2,4-dichlorobenzyl)-5-(4-chlorophenyl)pyrazole-3-carboxamide A) 1-(2,4-Dichlorobenzyl)-5-(4-chlorophenyl)pyrazole-3-carboxylic acid chloride This compound is prepared by the procedure described in step A of EXAMPLE 1 from 3.27 g of the compound obtained in Preparation 1.7, 2.2 ml of thionyl chloride and 60 ml of toluene. This gives 3.25 g of the expected product, which is used as such.

B) N-(Adamant-2-yl)-1-(2,4-dichlorobenzyl)-5-(4-chlorophenyl)pyrazole-3-carboxamide A solution of 0.39 g of 2-aminoadamantane hydrochloride and 0.58 ml of triethylamine in 15 ml of DCM is cooled to 0° C., a solution of 0.8 g of the compound obtained in the previous step in 15 ml of DCM is added dropwise and the reaction mixture is stirred for 16 hours at RT. It is poured into 50 ml of iced water, the organic phase is decanted, washed with water and with saturated NaCl solution and dried over $MgSO_4$ and the solvent is evaporated off under vacuum to give 0.42 g of the expected product after crystallization and then recrystallization from a DCM/iso ether mixture. M.p.=154° C.

EXAMPLE 9

N-[endo-Bicyclo[3.2.1]oct-3-yl]-1-(2,4-dichlorobenzyl)-5-(4-chlorophenyl)pyrazole-3-carboxamide This compound is prepared by the procedure described in step B of EXAMPLE 8 from 0.17 g of the compound obtained in Preparation 2.5, 0.3 ml of triethylamine in 10 ml of DCM and 0.41 g of the compound obtained in step A of EXAMPLE 8 in 10 ml of DCM. The product obtained is purified by chromatography on silica using a gradient of a toluene/AcOEt mixture (97/3; v/v to 95/5; v/v) as the eluent to give 0.43 g of the expected product. M.p.=130° C.

EXAMPLE 10

N-[(1S)-1,3,3-Trimethylbicyclo[2.2.1]hept-2endo-yl]-1-[(1R,S)-1-(2,4-dichlorophenyl)ethyl]-5-(4-chlorophenyl)pyrazole-3-carboxamide A) 1-[1-(2,4-Dichlorophenyl)ethyl]-5-(4-chlorophenyl)pyrazole-3-carboxylic acid chloride This compound is prepared by the procedure described in step A of EXAMPLE 1 from 0.68 g of the compound obtained in Preparation 1.14, 0.45 ml of thionyl chloride and 30 ml of toluene. 0.86 g of the expected product is obtained.

B) N-[(1S)-1,3,3-Trimethylbicyclo[2.2.1]hept-2endo-yl]-1-[(1R,S)-1-(2,4-dichlorophenyl)ethyl]-5-(4-chlorophenyl)pyrazole-3-carboxamide This compound is prepared by the procedure described in step B of EXAMPLE 8 from 0.34 g of the compound obtained in Preparation 2.1 and 0.5 ml of triethylamine in 15 ml of DCM and 0.72 g of the compound obtained in the previous step in 15 ml of DCM. The product obtained is purified by chromatography on silica using a toluene/AcOEt mixture (96/4; v/v) as the eluent to give 0.84 g of the expected product. M.p.=70° C.

EXAMPLE 11

N-[(1S)-1,3,3-Trimethylbicyclo[2.2.1]hept-2endo-yl]-1-(3,4-dichlorobenzyl)-5-(2,6-dimethoxyphenyl)pyrazole-3-carboxamide A) 1-(3,4-Dichlorobenzyl)-5-(2,6-dimethoxyphenyl)pyrazole-3-carboxylic acid chloride This compound is prepared by the procedure described in step A of EXAMPLE 1 from 1.1 g of the compound obtained in Preparation 1.15, 0.6 ml of thionyl chloride and 25 ml of toluene. 1 g of the expected product is obtained.

B) N-[(1S)-1,3,3-Trimethylbicyclo[2.2.1]hept-2endo-yl]-1-(3,4-dichlorobenzyl)-5-(2,6-dimethoxyphenyl)pyrazole-3-carboxamide This compound is prepared by the procedure described in step B of EXAMPLE 1 from 0.303 g of the compound obtained in Preparation 2.1 and 0.4 ml of triethylamine in 15 ml of DCM and 0.6 g of the compound obtained in the previous step in 15 ml of DCM. The product is purified by crystallization from a cyclohexane/AcOEt mixture (75/25; v/v) to give 0.53 g of the expected product.

$[\alpha]_D^{20}$=+1.2° (c=1; EtOH)

The compounds according to the invention collated in TABLE 2 below are prepared by the procedures described in the previous EXAMPLES from the appropriate acid chlorides, themselves obtained from the acids described in the Preparations, and the compound obtained in Preparation 2.1.

TABLE 2

(I)

(1(S), 2endo)

| Example | $g_3$ | $g_4$ | $w_2$ | $w_3$ | $w_4$ | M.p. ° C. | $[\alpha]_D^{20}$ |
|---|---|---|---|---|---|---|---|
| | | | | | | | (c = 1; EtOH) |
| 12 (a) | H | M | H | Cl | Me | 116 | −3.3° |
| 13 (a) | H | OMe | H | Cl | Cl | 55 | — |
| 14 (a) | H | F | H | Cl | Me | 114 | −1.7° |
| 15 (b) | H | Cl | Cl | H | Cl | — | +0.6° |
| 16 (c) | Me | Me | H | Cl | Me | 65 | −1.5° |
| 17 (a) | Me | Me | H | Cl | F | 138 | −1.5° |
| 18 (a) | Me | Cl | H | H | Me | 59 | −3.1° |
| 19 (a) | Me | Cl | H | H | F | 158 | −2.4° |
| 20 (a) | Me | Cl | H | Cl | Me | 74 | −2.4° |
| 21 (a) | Me | Cl | H | Cl | F | 125 | −2.5° |
| 22 (d) | Me | Me | H | H | F | 175 | −3.3° |
| | | | | | | | (c = 1; DMF) |
| 23 (e) | H | Me | Cl | H | Cl | 140 | +0.5° |
| 24 (f) | Me | Cl | H | H | Et | 80 | −2.1° |
| 25 (g) | Me | Cl | H | Cl | Cl | 112 | +0.4° |
| 26 (f) | Me | Cl | Cl | H | Cl | 64 | +1° |

TABLE 2-continued (I) [Structure shown: pyrazole-3-carboxamide with 1,3,3-trimethylbicyclo[2.2.1]hept-2-yl group (1(S), 2endo), substituents g3, g4 on one phenyl and w2, w3, w4 on benzyl phenyl]

| Example | g3 | g4 | w2 | w3 | w4 | M.p. °C. | $[\alpha]_D^{20}$ |
|---------|-----|-----|-----|-----|-----|----------|---------|
| 27 (f)  | Cl  | Cl  | H   | H   | Me  | 110      | −1.1°   |
| 28 (f)  | Cl  | Cl  | H   | Cl  | Me  | 49       | −1.2°   |
| 29 (f)  | H   | SMe | Cl  | H   | Cl  | 128.2    | +1.4°   |
| 30 (f)  | H   | CF₃ | Cl  | H   | Cl  | 113.8    | +1.3°   |
| 31 (f)  | Me  | Cl  | H   | H   | OMe | 115      | +2.3°   |

(a) This compound is prepared by the procedures described in step A and then step B of EXAMPLE 1. The product is purified by chromatography on silica using a cyclohexane/AcOEt mixture (75/25; v/v) as the eluent.
(b) This compound is prepared by the procedures described in step A and then step B of EXAMPLE 8. The product is purified by chromatography on silica using a toluene/AcOEt mixture (90/10; v/v) as the eluent.
(c) This compound is prepared by the procedures described in step A and then step B of EXAMPLE 1. The product is purified by chromatography on silica using a cyclohexane/AcOEt mixture (80/20; v/v) as the eluent.
(d) This compound is prepared by the procedures described in step A and then step B of EXAMPLE 1. The product is purified by crystallization from AcOEt.
(e) This compound is prepared by the procedures described in step A and then step B of EXAMPLE 1. The product is purified by crystallization from iso ether.
(f) This compound is prepared by the procedures described in step A and then step B of EXAMPLE 32 using the compound obtained in Preparation 2.1. The product is purified by chromatography on silica using a cyclohexane/AcOEt mixture (80/20; v/v) as the eluent.
(g) This compound is prepared by the procedures described in step A and then step B of EXAMPLE 32 using the compound obtained in Preparation 2.1. After drying over Na₂SO₄ the solvent is partially concentrated and the precipitate formed is filtered off, washed with iso ether and dried.

EXAMPLE 32

N-[(1R)-1,3,3-Trimethylbicyclo[2.2.1]hept-2endo-yl]-1-(4-methylbenzyl)-5-(4-chloro-3-methylphenyl)pyrazole-3-carboxamide A) 1-(4-methylbenzyl)-5-(4-chloro-3-methylphenyl)pyrazole-3-carboxylic acid chloride This compound is prepared by the procedure described in step A of EXAMPLE 1 from 2.8 g of the compound obtained in Preparation 1.10, 1.7 ml of thionyl chloride and 50 ml of toluene. 2.9 g of the expected product are obtained.

B) N-[(1R)-1,3,3-Trimethylbicyclo[2.2.1]hept-2endo-yl]-1-(4-methylbenzyl)-5-(4-chloro-3-methylphenyl)pyrazole-3-carboxamide A solution of 1.6 g of the compound obtained in the previous step in 20 ml of DCM is added dropwise at RT to a solution of 0.765 g of the compound obtained in Preparation 2.6 and 1 ml of triethylamine in 20 ml of DCM and the reaction mixture is stirred overnight at RT. It is concentrated under vacuum, the residue is taken up with AcOEt, an insoluble material is filtered off, the filtrate is washed with saturated aqueous NaHCO₃ solution, with a buffer solution of pH 2 and with saturated aqueous NaCl solution and dried over Na₂SO₄ and the solvent is evaporated off under vacuum. The residue is chromatographed on silica using a cyclohexane/AcOEt mixture (75/25; v/v) as the eluent to give 1.08 g of the expected product. M.p.=108° C.

$[\alpha]_D^{20}$=+0.3° (c=1; EtOH)

EXAMPLE 33

N-[(1R)-1,3,3-Trimethylbicyclo[2.2.1]hept-2exo-yl]-1-(4-methylbenzyl)-5-(4-chloro-3-methylphenyl)pyrazole-3-carboxamide 0.6 ml of triethylamine and then dropwise a solution of 0.66 g of the compound obtained in step A of EXAMPLE 32 in 10 ml of DCM are added to a solution of 0.4 g of the mixture of compounds obtained in Preparation 2.3 in 10 ml of DCM and the reaction mixture is stirred overnight at RT. It is concentrated under vacuum, the residue is extracted with AcOEt, an insoluble material is filtered off, the filtrate is washed twice with saturated aqueous NaHCO₃ solution, twice with a buffer solution of pH 2 and twice with saturated aqueous NaCl solution, the organic phase is dried over Na₂SO₄ and the solvent is evaporated off under vacuum. The residue is chromatographed on silica using a cyclohexane/AcOEt mixture (80/20; v/v) as the eluent. A mixture containing 58% of the compound of EXAMPLE 33 (exo form) and 41.6% of the compound of EXAMPLE 32 (endo form), as determined by analytical HPLC, is obtained. The two isomers are separated by preparative HPLC: 0.31 g of the sample to purify is dissolved in a mixture of 13 ml of the starting eluent (A/B: 10%/90%), 9 ml of MeOH and 4 ml of acetonitrile. The following compounds are obtained after freeze-drying:

0.084 g of the compound of EXAMPLE 33; purity: 100% (analytical HPLC), with a RTi=41 minutes.

$[\alpha]_D^{20}$=−8.8° (c=1; EtOH)

NMR: δ (ppm): 0.8 to 1.15 : 3s : 9H; 1.2 to 2 : u : 7H; 2.2 to 2.25 : u : 6H; 3.5 : d : 1H; 5.4 : s : 2H; 6.8 to 7.7 : u : 9H;

0.056 g of the compound of EXAMPLE 32; purity: 98% (analytical HPLC), with a RTi=43.9 minutes.

EXAMPLE 34

N-[(1S)-1,3,3-Trimethylbicyclo[2.2.1]hept-2exo-yl]-1-(4-methylbenzyl)-5-(4-chloro-3-methylphenyl)pyrazole-3-carboxamide 1.5 ml of triethylamine and then dropwise a solution of 1.6 g of the compound obtained in step A of EXAMPLE 32 in 20 ml of DCM are added to a solution of 0.853 g of the compound obtained in Preparation 2.2 in 20 ml of DCM and the reaction mixture is stirred overnight at RT. It is concentrated under vacuum, the residue is extracted with AcOEt, an insoluble material is filtered off, the filtrate is washed twice with saturated aqueous NaHCO₃ solution, twice with a buffer solution of pH 2 and twice with saturated aqueous NaCl solution, the organic phase is dried over Na₂SO₄ and the solvent is evaporated off under vacuum. The residue is chromatographed on silica using a cyclohexane/AcOEt mixture (80/20; v/v) as the eluent. A mixture containing 58% of the compound of EXAMPLE 34 (exo form) and 37% of the compound of EXAMPLE 18 (endo form), as determined by analytical HPLC, is obtained. The two isomers are separated by preparative HPLC: 0.23 g of the sample to purify is dissolved in a mixture of 13 ml of the starting eluent (A/B:10%/90%), 3 ml of MeOH and 9 ml of acetonitrile. The following compounds are obtained after freeze-drying:

0.16 g of the compound of EXAMPLE 34; purity: 99.6% (analytical HPLC), with a RTi=34.7 minutes; m.p.=49° C.

[α]$_D^{20}$=−6.8° (c=1; EtOH)

NMR: δ (ppm): 0.8 to 1.15 : 3s : 9H; 1.2 to 2 : u : 7H; 2.1 to 2.4 : u : 6H; 3.5 : d : 1H; 5.4 : s : 2H; 6.8 to 7.6 : u : 9H;

0.066 g of the compound of EXAMPLE 18; purity: 94.7% (analytical HPLC) with a RTi=37.2 minutes.

EXAMPLE 35

N-(2,2,6,6-Tetramethylcyclohex-1-yl)-1-(4-methylbenzyl)-5-(4-chloro-3-methylphenyl)pyrazole-3-carboxamide 0.4 ml of triethylamine and then dropwise a solution of 0.55 g of the compound obtained in step A of EXAMPLE 32 in 15 ml of DCM are added to a solution of 0.25 g of the compound obtained in Preparation 2.7 in 15 ml of DCM and the reaction mixture is stirred overnight at RT. It is concentrated under vacuum, the residue is extracted with AcOEt, the filtrate is washed twice with saturated aqueous NaHCO$_3$ solution, twice with a buffer solution of pH 2 and twice with saturated aqueous NaCl solution, the organic phase is dried over Na$_2$SO$_4$ and the solvent is evaporated off under vacuum. The residue is chromatographed on silica using a cyclohexane/AcOEt mixture (80/20; v/v) as the eluent to give 0.1 g of the expected product.

EXAMPLE 36

N-[Bicyclo[2.2.1]hept-2exo-yl]-1-(3-chloro-4-methylbenzyl)-5-(3,4-dichlorophenyl)pyrazole-3-carboxamide A) 1-(3-chloro-4-methylbenzyl)-5-(3,4-dichlorophenyl)pyrazole-3-carboxylic acid chloride This compound is prepared by the procedure described in step A of EXAMPLE 1 from 10 g of the compound obtained in Preparation 1.22, 5.5 ml of thionyl chloride and 125 ml of toluene. 9.41 g of the expected product are obtained.

B) N-[Bicyclo[2.2.1]hept-2exo-yl]-1-(3-chloro-4-methylbenzyl)-5-(3,4-dichlorophenyl)pyrazole-3-carboxamide A solution of 1.5 g of the compound obtained in the previous step in 15 ml of DCM is added at RT to a solution of 0.411 g of 2exo-aminonorbornane and 1 ml of triethylamine in 15 ml of DCM and the reaction mixture is stirred overnight at RT. It is concentrated under vacuum, the residue is extracted with AcOEt, an insoluble material is filtered off, the organic phase is washed with saturated aqueous NaHCO$_3$ solution and with a buffer solution of pH 2, dried over MgSO$_4$ and the solvent is evaporated off under vacuum. The residue is chromatographed on silica using a cyclohexane/AcOEt mixture (80/20; v/v) as the eluent to give 0.5 g of the expected product. M.p.=145.6° C.

EXAMPLE 37

N-[Bicyclo[2.2.1]hept-2exo-yl]-N-propyl-1-(3-chloro-4-methylbenzyl)-5-(3,4-dichlorophenyl)pyrazole-3-carboxamide This compound is prepared by the procedure described in step B of EXAMPLE 36 from 0.695 g of the compound obtained in Preparation 2.4, 1 ml of triethylamine in 15 ml of DCM and 1.5 g of the compound obtained in step A of EXAMPLE 36 in 15 ml of DCM. 0.417 g of the expected product is obtained.

EXAMPLE 38

N-(2-Methylcyclohex-1-yl)-1-(3-chloro-4-methylbenzyl)-5-(3,4-dichlorophenyl)pyrazole-3-carboxamide This compound is prepared by the procedure described in step B of EXAMPLE 36 from 1 ml of 2-methylcyclohexylamine, 1 ml of triethylamine in 15 ml of DCM and 1.5 g of the compound obtained in step A of EXAMPLE 36 in 15 ml of DCM. The compound is purified by chromatography on silica using a DCM/MeOH mixture (98/2; v/v) as the eluent to give 0.27 g of the expected product. M.p.=165° C.

EXAMPLE 39

N-(2,6-Dimethylcyclohex-1-yl)-1-(3-chloro-4-methylbenzyl)-5-(3,4-dichlorophenyl)pyrazole-3-carboxamide This compound is prepared by the procedure described in step B of EXAMPLE 36 from 0.605 g of 2,6-dimethylcyclohexylamine hydrochloride, 1 ml of triethylamine in 15 ml of DCM and 1.5 g of the compound obtained in step A of EXAMPLE 36 in 15 ml of DCM. 0.6 g of the expected product is obtained; m.p.=59.9° C.

EXAMPLE 40

N-[(1S)-1,3,3-Trimethylbicyclo[2.2.1]hept-2endo-yl]-1-[(1R,S)-1-(3,4-dichlorophenyl)ethyl]-5-(4-methylphenyl)pyrazole-3-carboxamide A) 1-[1-(3,4-Dichlorophenyl)ethyl]-5-(4-methylphenyl)pyrazole-3-carboxylic acid chloride 0.7 ml of thionyl chloride is added at RT to a suspension of 1.2 g of the compound obtained in Preparation 1.25 in 50 ml of toluene and the reaction mixture is then refluxed for 2 hours. After cooling to RT, it is concentrated under vacuum, the residue is taken up with toluene and the solvent is evaporated off under vacuum to give 1.3 g of the expected product.

B) N-[(1S)-1,3,3-Trimethylbicyclo[2.2.1]hept-2endo-yl]-1-[(1R,S)-1-(3,4-dichlorophenyl)ethyl]-5-(4-methylphenyl)pyrazole-3-carboxamide 0.6 ml of triethylamine and then dropwise a solution of 0.7 g of the compound obtained in the previous step in 15 ml of DCM are added to a solution of 0.341 g of the compound obtained in Preparation 2.1 in 15 ml of DCM and the reaction mixture is stirred overnight at RT. It is concentrated under vacuum, the residue is taken up with AcOEt, an insoluble material is filtered off, the filtrate is washed with saturated aqueous NaHCO$_3$ solution, with a buffer solution of pH 2 and with saturated aqueous NaCl solution, the organic phase is dried over Na$_2$SO$_4$ and the solvent is evaporated off under vacuum. The residue is chromatographed on silica using a cyclohexane/AcOEt mixture as the eluent to give 0.54 g of the expected product. M.p.=112° C.

NMR: δ (ppm): 0.6 to 1.9 : u : 19H; 2.3 s : 3H; 3.6 : mt : 1H; 5.55 : qd : 1H; 6.6 to 7.6 : u : 9H.

EXAMPLE 41

N-[(1S)-1,3,3-Trimethylbicyclo[2.2.1]hept-2endo-yl]-1-[(1R,S)-1-(4-methylphenyl)ethyl]-5-(4-chloro-3-methylphenyl)pyrazole-3-carboxamide A) 1-[1-(4-Methylphenyl)ethyl]-5-(4-chloro-3-methylphenyl)pyrazole-3-carboxylic acid chloride This compound is prepared by the procedure described in step A of EXAMPLE 40 from 0.61 g of the compound obtained in Preparation 1.26 in 30 ml of toluene and 0.4 ml of thionyl chloride. 0.7 g of the expected product is obtained.

B) N-[(1S)-1,3,3-Trimethylbicyclo[2.2.1]hept-2endo-yl]-1-[(1R,S)-1-(4-methylphenyl)ethyl]-5-(4-chloro-3-methylphenyl)pyrazole-3-carboxamide This compound is prepared by the procedure described in step B of EXAMPLE 40 from 0.36 g of the compound obtained in Preparation 2.1 in 15 ml of DCM, 0.45 g of triethylamine and a solution of 0.7 g of the compound obtained in the previous step in 15 ml of DCM. The compound is purified by chromatography on silica using a cyclohexane/AcOEt mixture (75/25; v/v) as the eluent to give 0.13 g of the expected product. M.p.=65° C.

NMR: δ (ppm): 0.8 to 2.05 : u : 19H; 2.2 to 2.5 : u : 6H; 3.75 : d : 1H; 5.65 : qd : 1H; 6.8 to 7.7 : u : 9H.

EXAMPLE 42

N-[(1S)-1,3,3-Trimethylbicyclo[2.2.1]hept-2endo-yl]-1-[(1R,S)-1-(3,4-dichlorophenyl)ethyl]-5-(4-chloro-3-methylphenyl)pyrazole-3-carboxamide A) 1-[1-(3,4-Dichlorophenyl)ethyl]-5-(4-chloro-3-methylphenyl)pyrazole-3-carboxylic acid chloride This compound is prepared by the procedure described in step A of EXAMPLE 40 from 0.9 g of the compound obtained in Preparation 1.27 in 20 ml of toluene and 0.5 ml of thionyl chloride. 0.95 g of the expected product is obtained.

B) N-[(1S)-1,3,3-Trimethylbicyclo[2.2.1]hept-2endo-yl]-1-[(1R,S)-1-(3,4-dichlorophenyl)ethyl]-5-(4-chloro-3-methylphenyl)pyrazole-3-carboxamide This compound is prepared by the procedure described in step B of EXAMPLE 40 from 0.455 g of the compound obtained in Preparation 2.1 in 15 ml of DCM, 0.8 g of triethylamine and a solution of 0.95 g of the compound obtained in the previous step in 15 ml of DCM. After drying of the organic phase over $Na_2SO_4$, the solvent is partially concentrated under vacuum and the crystals formed are filtered off to give 0.76 g of the expected product. M.p.=156° C.

NMR: δ (ppm): 0.6 to 2 : u : 19H; 2.35 : s : 3H; 3.7 : mt : 1H; 5.7 : qd : 1H; 6.7 to 7.7 : u : 8H.

EXAMPLE 43

N-[(1S)-1,3,3-Trimethylbicyclo[2.2.1]hept-2endo-yl]-1-[(1R,S)-1-(4-methylphenyl)propyl]-5-(4-chloro-3-methylphenyl)pyrazole-3-carboxamide A) 1-[1-(4-Methylphenyl)propyl]-5-(4-chloro-3-methylphenyl)pyrazole-3-carboxylic acid chloride This compound is prepared by the procedure described in step A of EXAMPLE 40 from 0.87 g of the compound obtained in Preparation 1.28 in 50 ml of toluene and 0.26 ml of thionyl chloride. 0.89 g of the expected product is obtained.

B) N-[(1S)-1,3,3-Trimethylbicyclo[2.2.1]hept-2endo-yl]-1-[(1R,S)-1-(4-methylphenyl)propyl]-5-(4-chloro-3-methylphenyl)pyrazole-3-carboxamide 0.363 ml of triethylamine is added to a solution of 0.51 g of the compound obtained in the previous step and 0.25 g of the compound obtained in Preparation 2.1 in 50 ml of DCM and the reaction mixture is stirred for 72 hours at RT. It is concentrated under vacuum, the residue is extracted with AcOEt, an insoluble material is filtered off, the filtrate is washed with saturated aqueous $NaHCO_3$ solution, with a buffer solution of pH 2 and with saturated NaCl solution, the organic phase is dried over $Na_2SO_4$ and the solvent is evaporated off under vacuum. The residue is chromatographed on silica using a cyclohexane/AcOEt mixture (75/25; v/v) as the eluent to give 0.44 g of the expected product. M.p.=136° C.

NMR: δ (ppm): 0.5 to 2.6 : u : 27H; 3.75 : d : 1H; 4.95 : dd : 1H; 6.6 to 7.4 : u : 9H.

EXAMPLE 44

N-[(1S)-1,3,3-Trimethylbicyclo[2.2.1]hept-2endo-yl]-1-[1-methyl-1-(4-methylphenyl)ethyl]-5-(4-chloro-3-methylphenyl)pyrazole-3-carboxamide A) 1-[1-Methyl-1-(4-methylphenyl)ethyl]-5-(4-chloro-3-methylphenyl)pyrazole-3-carboxylic acid chloride This compound is prepared by the procedure described in step A of EXAMPLE 40 from 1.5 g of the compound obtained in Preparation 1.29 in 100 ml of toluene and 0.44 ml of thionyl chloride. 1.55 g of the expected product are obtained.

B) N-[(1S)-1,3,3-Trimethylbicyclo[2.2.1]hept-2endo-yl]-1-[1-methyl-1-(4-methylphenyl)ethyl]-5-(4-chloro-3-methylphenyl)pyrazole-3-carboxamide 0.424 ml of triethylamine is added to a solution of 0.59 g of the compound obtained in the previous step and 0.29 g of the compound obained in Preparation 2.1 in 50 ml of DCM and the reaction mixture is stirred overnight at RT. It is concentrated under vacuum, the residue is extracted with AcOEt, an insoluble material is filtered off, the filtrate is washed with saturated aqueous $NaHCO_3$ solution, with a buffer solution of pH 2 and with saturated NaCl solution, the organic phase is dried over $Na_2SO_4$ and the solvent is evaporated off under vacuum. The residue is chromatographed on silica using a DCM/MeOH mixture (97.5/2.5; v/v) as the eluent to give 0.3 g of the expected product. M.p.=195° C.

$[\alpha]_D^{20}$=−6.5° (c=0.64; DCM)

EXAMPLE 45

N-[(1S)-1,3,3-Trimethylbicyclo[2.2.1]hept-2endo-yl]-1-(2,4-dichlorobenzyl)-5-(4-chlorophenyl)-4-methylpyrazole-3-carboxamide A) 1-(2,4-Dichlorobenzyl)-5-(4-chlorobenzyl)-4-methylpyrazole-3-carboxylic acid chloride 0.191 ml of thionyl chloride is added at RT to a solution of 0.71 g of the compound obtained in Preparation 1.30 in 50 ml of toluene and the reaction mixture is then refluxed overnight. It is concentrated under vacuum, the residue is taken up with toluene and the solvent is evaporated off under vacuum to give 0.72 g of the expected product in the form of an oil which solidifies.

B) N-[(1S)-1,3,3-Trimethylbicyclo[2.2.1]hept-2endo-yl]-1-(2,4-dichlorobenzyl)-5-(4-chlorophenyl)-4-methylpyrazole-3-carboxamide This compound is prepared by the procedure described in step B of EXAMPLE 43 from 0.315 g of the compound obtained in Preparation 2.1, 0.46 ml of triethylamine and 0.653 g of the compound obtained in the previous step in 50 ml of DCM. 0.68 g of the expected product is obtained; m.p.=125° C.

$[\alpha]_D^{20}$=−0.3° (c=1; EtOH)

EXAMPLE 46

N-[(1S)-1,3,3-Trimethylbicyclo[2.2.1]hept-2endo-yl]-1-(3,4-dichlorobenzyl)-5-(4-chlorophenyl)-4-methylpyrazole-3-carboxamide A) 1-(3,4-Dichlorobenzyl)-5-(4-chlorophenyl)-4-methylpyrazole-3-carboxylic acid chloride This compound is prepared by the procedure described in step A of EXAMPLE 45 from 1 g of the compound obtained in Preparation 1.31 in 50 ml of toluene and 0.28 ml of thionyl chloride. 1.03 g of the expected product are obtained in the form of an oil which solidifies.

B) N-[(1S)-1,3,3-Trimethylbicyclo[2.2.1]hept-2endo-yl]-1-(3,4-dichlorobenzyl)-5-(4-chlorophenyl)-4-methylpyrazole-3-carboxamide This compound is prepared by the procedure described in step B of EXAMPLE 43 from 0.315 g of the compound obtained in Preparation 2.1, 0.46 ml of triethylamine and 0.687 g of the compound obtained in the previous step in 50 ml of DCM. 0.72 g of the expected product is obtained; m.p.=69° C.

$[\alpha]_D^{20}$=−1.8° (c=1; EtOH)

EXAMPLE 47

N-[(1S)-1,3,3-Trimethylbicyclo[2.2.1]hept-2endo-yl]-1-(3-chloro-4-methylbenzyl)-5-(4-chlorophenyl)-4-methylpyrazole carboxamide A) 1-(3-Chloro-4-methylbenzyl)-5-(4-chlorophenyl)-4-methylpyrazole-3-carboxylic acid chloride This compound is prepared by the procedure described in step A of EXAMPLE 45 from 1 g of the crude compound obtained in Preparation 1.32 in 50 ml of toluene and 0.29 ml of thionyl chloride. 1.05 g of the expected product are obtained.

B) N-[(1S)-1,3,3-Trimethylbicyclo[2.2.1]hept-2endo-yl]-1-(3-chloro-4-methylbenzyl)-5-(4-chlorophenyl)-4-methylpyrazole carboxamide This compound is prepared by the procedure described in step B of EXAMPLE 43 from 0.29 g of the compound obtained in Preparation 2.1, 0.24 ml of triethylamine and 0.6 g of the compound obtained in the previous step in 50 ml of DCM. 0.43 g of the expected product is obtained; m.p.=58° C.

$[\alpha]_D^{20}$=−1.7° (c=1; EtOH)

EXAMPLE 48

N-[(1S)-1,3,3-Trimethylbicyclo[2.2.1]hept-2endo-yl]-1-(4-methylbenzyl)-5-(4-chloro-3-methylphenyl)-4-methylpyrazole-3-carboxamide A) 1-(4-Methylbenzyl)-5-(4-chloro-3-methylphenyl)-4-methylpyrazole-3-carboxylic acid chloride 1 ml of thionyl chloride is added to a suspension of 1.5 g of the compound obtained in Preparation 1.33 in 40 ml of toluene and the reaction mixture is refluxed for 2 hours. It is concentrated under vacuum, the residue is taken up with toluene and the solvent is evaporated off under vacuum to give 1.5 g of the expected product.

B) N-[(1S)-1,3,3-Trimethylbicyclo[2.2.1]hept-2endo-yl]-1-(4-methylbenzyl)-5-(4-chloro-3-methylphenyl)-4-methylpyrazole-3-carboxamide This compound is prepared by the procedure described in step B of EXAMPLE 43 from 0.42 g of the compound obtained in Preparation 2.1, 0.7 ml of triethylamine and 0.8 g of the compound obtained in the previous step in 40 ml of DCM. 0.62 g of the expected product is obtained; m.p.=58° C.

$[\alpha]_D^{20}$ =−2.4° (c=1; EtOH)

EXAMPLE 49

N-[(1S)-1,3,3-Trimethylbicyclo[2.2.1]hept-2endo-yl]-1-(3,4-dichlorobenzyl)-5-(4-chloro-3-methylphenyl)-4-methylpyrazole-3-carboxamide A) 1-(3,4-Dichlorobenzyl)-5-(4-chloro-3-methylphenyl)-4-methylpyrazole-3-carboxylic acid chloride 1.5 ml of thionyl chloride are added to a suspension of 2.7 g of the compound obtained in Preparation 1.34 in 50 ml of toluene and the reaction mixture is refluxed for 2 hours. It is concentrated under vacuum, the residue is taken up with toluene and the solvent is evaporated off under vacuum to give 2.8 g of the expected product.

B) N-[(1S)-1,3,3-Trimethylbicyclo[2.2.1]hept-2endo-yl]-1-(3,4-dichlorobenzyl)-5-(4-chloro-3-methylphenyl)-4-methylpyrazole-3-carboxamide This compound is prepared by the procedure described in step B of EXAMPLE 43 from 0.683 g of the compound obtained in Preparation 2.1, 1.2 ml of triethylamine and 1.5 g of the compound obtained in the previous step in 40 ml of DCM. 1.03 g of the expected product are obtained; m.p.=69° C.

$\alpha_D^{20}$=−2.1° (c=1; EtOH)

EXAMPLE 50

N-[(1S)-1,3,3-Trimethylbicyclo[2.2.1]hept-2endo-yl]-1-(3-chloro-4-methylbenzyl)-5-(4-chlorophenyl)-4-(ethoxymethyl)pyrazole-3-carboxamide A) 1-(3-Chloro-4-methylbenzyl)-5-(4-chlorophenyl)-4-(ethoxymethyl)pyrazole-4-carboxylic acid chloride 0.053 ml of thionyl chloride is added to a solution of 0.2 g of the compound obtained in Preparation 1.35 in 30 ml of toluene and the reaction mixture is refluxed for 2 hours. It is concentrated under vacuum, the residue is taken up with toluene and the solvent is evaporated off under vacuum to give 0.21 g of the expected product in the form of an oil.

B) N-[(1S)-1,3,3-Trimethylbicyclo[2.2.1]hept-2endo-yl]-1-(3-chloro-4-methylbenzyl)-5-(4-chlorophenyl)-4-(ethoxymethyl)pyrazole-3-carboxamide This compound is prepared by the procedure described in step B of EXAMPLE 40 from 0.086 g of the compound obtained in Preparation 2.1 in 25 ml of DCM, 0.125 ml of triethylamine and 0.2 g of the compound obtained in the previous step in 25 ml of DCM. 0.15 g of the expected product is obtained, m.p.=50–51° C.

$[\alpha]_D^{20}$=−2.8° (c=1; EtOH)

EXAMPLE 51

N-[(1S)-1,3,3-Trimethylbicyclo [2.2.1]hept-2endo-yl]-1-(5-chloroindan-1-yl)-5-(4-chlorophenyl)pyrazole-3-carboxamide A) 1-(5-Chloroindan-1-yl)-5-(4-chlorophenyl)pyrazole-3-carboxylic acid chloride 0.6 ml of thionyl chloride is added to a suspension of 1 g of the compound obtained in Preparation 1.36 in 20 ml of toluene and the reaction mixture is refluxed for 2 hours. After cooling to RT, it is concentrated under vacuum, the residue is taken up with toluene and the solvent is evaporated off under vacuum to give 1 g of the expected product.

B) N-[(1S)-1,3,3-Trimethylbicyclo[2.2.1]hept-2endo-yl]-1-(5-chloroindan-1-yl)-5-(4-chlorophenyl)pyrazole-3-carboxamide A solution of 1 g of the compound obtained in the previous step in 15 ml of DCM is added dropwise at RT to a solution of 0.493 g of the compound obtained in Preparation 2.1 and 1 ml of triethylamine in 15 ml of DCM and the reaction mixture is stirred overnight at RT. It is concentrated under vacuum, the residue is taken up with AcOEt, an insoluble material is filtered off, the filtrate is washed with saturated aqueous $NaHCO_3$ solution, with a buffer solution of pH 2 and with saturated aqueous NaCl solution, the organic phase is dried over $Na_2SO_4$ and the solvent is evaporated off under vacuum. The residue is chromatographed on silica using a cyclohexane/AcOEt mixture (80/20; v/v) as the eluent to give 0.71 g of the expected product. M.p.=86° C.

$[\alpha]_D^{20}$=+0.5° (c=1; EtOH)

NMR: δ (ppm): 0.4 to 1.8 : u : 16H; 2.5 : mt : 2H; 2.95 mt : 2H; 3.5 d : 1H; 5.8 : t : 1H; 6.6 to 7.7 : u : 9H.

An Overhauser effect (NOE) is observed between the proton in position 1- of the indan-1-yl group and the protons $g_2=_6$=H.

EXAMPLE 52
(1R)-1,3,3-Trimethylbicyclo[2.2.1]hept-2endo-yl 1-(3,4-dichloro-benzyl)-5-(4-methylphenyl)pyrazole-3-carboxylate A mixture of 1.5 g of the compound obtained in step A of EXAMPLE 1, 0.73 g of (1R)-endo-(+)-fenchyl alcohol, 50 ml of pyridine and 0.02 g of 4-dimethylaminopyridine is stirred for 72 hours at RT. It is concentrated under vacuum and the residue is chromatographed on silica using DCM as the eluent to give 0.23 g of the expected product. M.p.=107° C.

$[\alpha]_D^{20}$=+6.8° (c=1; MeOH)

EXAMPLE 53
(1R)-1,3,3-Trimethylbicyclo[2.2.1]hept-2endo-yl 1-(3-chloro-4-methylbenzyl)-5-(3,4-dichlorophenyl)pyrazole-3-carboxylate 0.97 g of (1R)-endo-(+)-fenchyl alcohol and 0.02 g of 4-dimethylaminopyridine are added to a solution of 2.6 g of the compound obtained in step A of EXAMPLE 36 in 50 ml of pyridine and the reaction mixture is then stirred for 48 hours at RT. It is concentrated under vacuum, the residue is taken up in ether and the precipitate formed is filtered off, dried and then chromatographed on silica using a cyclohexane/AcOEt/DCM mixture (85/15/3; v/v/v) as the eluent to give 0.4 g of the expected product. M.p.=161° C.

$[\alpha]_D^{20}$=+3.9° (c=1; DCM)

EXAMPLE 54
N-[(1S)-1,3,3-Trimethylbicyclo[2.2.1]hept-2endo-yl]-1-(2,4-dichlorobenzyl)-3-(4-chlorophenyl)pyrazole-5-carboxamide A) 1-(2,4-Dichlorobenzyl)-3-(4-chlorophenyl)pyrazole-5-carboxylic acid chloride 0.54 ml of thionyl chloride is added to a suspension of 0.79 g of the compound obtained in Preparation 1.38 in 20 ml of toluene and the reaction mixture is refluxed for 3 hours. It is concentrated under vacuum, the residue is taken up with 20 ml of toluene and the solvent is evaporated off under vacuum to give 0.9 g of the expected product.

B) N-[(1S)-1,3,3-Trimethylbicyclo[2.2.1]hept-2endo-yl]-1-(2,4-dichlorobenzyl)-3-(4-chlorophenyl)pyrazole-5-carboxamide A solution of 0.21 g of the compound obtained in Preparation 2.1 and 0.3 ml of triethylamine in 10 ml of DCM is cooled to 0° C., a solution of 0.45 g of the compound obtained in the previous step in 15 ml of DCM is added dropwise and the reaction mixture is stirred for 16 hours at RT. It is poured into 100 ml of iced water, the mixture is extracted with DCM, the organic phase is washed with water and with saturated NaCl solution, dried over $Na_2SO_4$ and the solvent is evaporated off under vacuum to give 0.37 g of the expected product after crystallization from a DCM/iso ether mixture. M.p.=171° C.

$\alpha_D^{20}$=+6.8° (c=1; MeOH)

EXAMPLE 55

| Gelatine capsule | |
| --- | --- |
| Compound of EXAMPLE 18 | 1 mg |
| Modified corn starch | 47 mg |
| Lactose monohydrate EFK | 150 mg |
| Magnesium stearate | 2 mg |
| for an opaque white gelatin capsule, size 3, of: | 200 mg |

EXAMPLE 56

| Gelatine capsule | |
| --- | --- |
| Compound of EXAMPLE 18 | 30 mg |
| Modified corn starch | 30 mg |
| Magnesium stearate | 2 mg |
| Lactose monohydrate EFK, qs | |
| for an opaque white gelatin capsule, size 3, of: | 200 mg |

EXAMPLE 57

| Tablet | |
| --- | --- |
| Compound of EXAMPLE 18 | 10 mg |
| PVP (polyvinylpyrrolidone) K30 | 4.5 mg |
| Cross-linked sodium carboxy-methylcellulose | 3 mg |
| Magnesium stearate | 1.5 mg |
| Lactose monohydrate 200 mesh, qs | |
| Purified water, qs | |
| for a scored tablet of: | 150 mg |

EXAMPLE 58

| Gelatine capsule | |
| --- | --- |
| Compound of EXAMPLE 48 | 30 mg |
| Hydroxypropylmethylcellulose 6 mPas | 7.5 mg |
| Lactose monohydrate 200 mesh, qs | |
| Magnesium stearate | 2.5 mg |
| Purified water, qs | |
| for a gelatin capsule, size 1, of: | 250 mg |

EXAMPLE 59

| Tablet | |
| --- | --- |
| Compound of EXAMPLE 48 | 40 mg |
| Corn starch | 50 mg |
| PVP K 30 | 9 mg |
| Sodium carboxymethylstarch | 9 mg |
| Magnesium stearate | 3 mg |
| Lactose monohydrate 200 mesh, qs | |
| for a scored tablet of: | 300 mg |

We claim:

1. A compound of the formula:

(I)

in which:

$X_1$ is a group —$NR_1R_2$ or a group —$OR_2$;

$g_2$, $g_3$, $g_4$, $g_5$, $g_6$ and $w_2$, $w_3$, $w_4$, $w_5$, $w_6$ are identical or different and are each independently hydrogen, a halogen atom, a ($C_1$–$C_4$)alkyl, a ($C_1$–$C_4$)alkoxy, a trifluoromethyl, a nitro or a ($C_1$–$C_4$)alkylthio, with the proviso that at least one of the substituents $g_2$, $g_3$, $g_4$, $g_5$, $g_6$ and at least one of the substituents $w_2$, $w_3$, $w_4$, $w_5$, $w_6$ are other than hydrogen;

$R_1$ is hydrogen or a ($C_1$–$C_4$)alkyl;

$R_2$ is a non-aromatic ($C_3$–$C_{15}$)carbocyclic radical which is unsubstituted or monosubstituted or polysubstituted by a substituent selected from a halogen atom, a ($C_1$–$C_4$) alkyl and a ($C_1$–$C_4$)alkoxy;

$R_3$ is hydrogen or a group —$CH_2R_6$;

$R_4$ and $R_5$ are each independently a hydrogen, a ($C_1$–$C_4$) alkyl or a trifluoromethyl;

or else $R_4$ is hydrogen and $R_5$ and $w_6$ together constitute an ethylene or trimethylene radical; and $R_6$ is hydrogen, or when the substituents $g_2$, $g_3$, $g_4$, $g_5$ and/or $g_6$ are other than a ($C_1$–$C_4$)alkyl, $R_6$ is hydrogen, a ($C_1$–$C_4$)alkyl, a fluorine, a hydroxyl, a ($C_1$–$C_5$)alkoxy, a ($C_1$–$C_5$)alkylthio, a hydroxy($C_1$–$C_5$)alkoxy, a cyano, a ($C_1$–$C_5$)alkylsulfinyl or a ($C_1$–$C_5$)alkylsulfonyl;

and its salts.

2. A compound of formula (I) according to claim 1, in which $X_1$ is a group —$NR_1R_2$ in which $R_1$ is hydrogen;

and its salts.

3. A compound of formula (I) according to claim 1, in which $X_1$ is a group —$NR_1R_2$ or a group —$OR_2$, where $R_2$ is a 1,3,3-trimethylbicyclo[2.2.1]hept-2-yl radical or a bicyclo[3.2.1]oct-3-yl radical;

and its salts.

4. A compound of formula (I) according to claim 1, in which $R_3$ is hydrogen or a group —$CH_2R_6$, $R_6$ being hydrogen;

and its salts.

5. A compound of formula (I) according to claim 1, in which either $R_4$ and $R_5$ are each hydrogen or $R_4$ is hydrogen and $R_5$ is a ($C_1$–$C_4$)alkyl;

and its salts.

6. A compound of formula (I) according to claim 1, in which $g_2$, $g_5$ and $g_6$ are each hydrogen and $g_3$ and $g_4$ are as defined for the compounds (I) in claim 1;

and its salts.

7. A compound of formula (I) according to claim 1, in which $w_5$ and $w_6$ are each hydrogen, $w_4$ is a halogen atom, a ($C_1$–$C_4$)alkyl, a ($C_1$–$C_4$)alkoxy, a trifluoromethyl or a ($C_1$–$C_4$)alkylthio and either $w_2$ and $w_3$ are each hydrogen or one is hydrogen and the other is a halogen atom, a ($C_1$–$C_4$) alkyl or a trifluoromethyl;

and its salts.

8. A compound according to claim 1, of the formula:

(Ia)

in which:

$R_1$ and $R_2$ are as defined for the compounds of formula (I);

$R_{3a}$ is hydrogen or a group —$CH_2R_{6a}$;

$R_{6a}$ is hydrogen, or when the substituents $g_3$ and/or $g_4$ are other than a ($C_1$–$C_4$) alkyl, $R_6$ is hydrogen, a methyl group or an ethyl group;

$g_{3a}$ is hydrogen, a halogen atom, a ($C_1$–$C_4$)alkyl or a trifluoromethyl;

$g_{4a}$ is a halogen atom, a ($C_1$–$C_4$)alkyl or a trifluoromethyl;

$w_{4a}$ is a halogen atom, a ($C_1$–$C_4$)alkyl or a trifluoromethyl; and $w_{2a}$ and $w_{3a}$ are each hydrogen or one is hydrogen and the other is a halogen atom, a ($C_1$–$C_4$)alkyl or a trifluoromethyl;

and its salts.

9. A compound according to claim 1, of the formula:

(Ib)

in which:

$R_1$ and $R_2$ are as defined for the compounds of formula (I) in claim 1;

$R_{3a}$, $w_{2a}$, $w_{3a}$, $w_{4a}$, $g_{3a}$ and $g_{4a}$ are as defined for the compounds of formula (Ia) in claim 8; and $R_{5b}$ is a $(C_1-C_4)$alkyl;

and its salts.

10. A compound according to claim 1, of the formula:

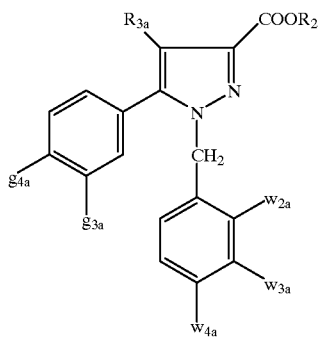

(Ic)

in which:

$R_2$ is as defined for the compounds of formula (I) in claim 1; and $R_{3a}$, $w_{2a}$, $w_{3a}$, $w_{4a}$, $g_{3a}$ and $g_{4a}$ are as defined for the compounds of formula (Ia) in claim 8;

and its salts.

11. A process for the preparation of the compounds of formula (I) according to claim 1 and their salts, which comprises the steps of:

1) treating a functional derivative of the pyrazole-3-carboxylic acid of the formula

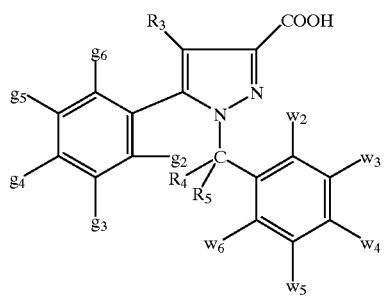

(II)

in which $w_2$, $w_3$, $w_4$, $w_5$, $w_6$, $g_2$, $g_3$, $g_4$, $g_5$, $g_6$, $R_3$, $R_4$ and $R_5$ are as defined for the compounds of formula (I) in claim 1, with a compound of the formula

H—X$_1$ (XXIV)

in which $X_1$ is as defined for the compounds of formula (I) in claim 1; and 2) optionally converting the resulting compound to one of its salts.

12. A process according to claim 11, for the preparation of the compounds of formula (I) in which $X_1$ is a group —NR$_1$R$_2$ and their salts, which comprises the steps of:

1) treating a functional derivative of the pyrazole-3-carboxylic acid of formula (II) as defined in claim 11 with an amine of the formula:

HNR$_1$R$_2$ (III)

in which R$_1$ and R$_2$ are as defined for the compounds of formula (I) in claim 1; and 2) optionally converting the resulting compound to one of its salts.

13. A process according to claim 11, for the preparation of the compounds of formula (I) in which $X_1$ is a group —OR$_2$ and their salts, which comprises the steps of:

1) treating a functional derivative of the pyrazole-3-carboxylic acid of formula (II) as defined in claim 11 with an alcohol of the formula:

HOR$_2$ (XIV)

in which R$_2$ is as defined for the compounds of formula (I) in claim 1; and 2) optionally converting the resulting compound to one of its salts.

14. A compound of the formula:

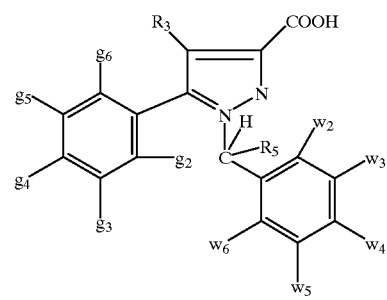

(XIII)

in which:

$X_1$, $g_2$, $g_3$, $g_4$, $g_5$, $g_6$, $w_2$, $w_3$, $w_4$, $w_5$, $w_6$, $R_3$ and $R_5$ are as defined for the compounds of formula (I) in claim 1;

and its salts.

15. A process for the preparation of the compounds of formula (II) as defined in claim 11 and the compounds of formula (XII):

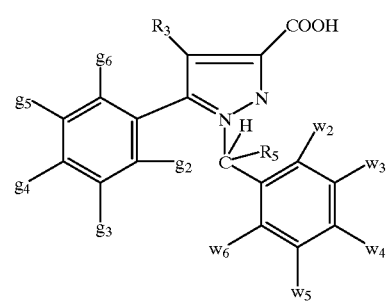

(XII)

in which $g_2$, $g_3$, $g_4$, $g_5$, $g_6$, $w_2$, $w_3$, $w_4$, $w_5$, $w_6$, $R_3$ and $R_5$ are as defined for the compounds of formula (I) in claim 1, which comprises the steps of:

1) treating a compound of the formula:

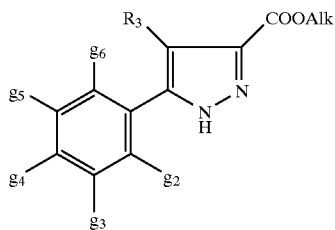
(XXV)

in which $g_2$, $g_3$, $g_4$, $g_5$, $g_6$ and $R_3$ are as defined above and Alk is a methyl or ethyl group, with a strong base in a solvent, and then reacting the resulting anion with a compound of the formula:

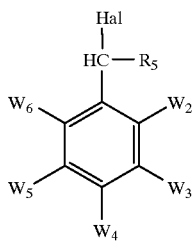
(VII)

in which $w_2$, $w_3$, $w_4$, $w_5$, $w_6$ and $R_5$ are as defined above and Hal is a halogen atom, to give:

either a compound of the formula:

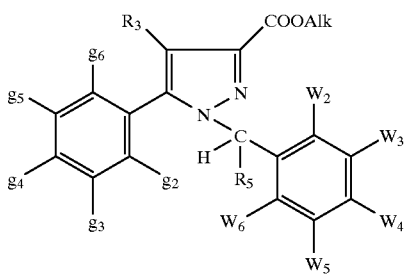
(XXVI)

when the reaction is carried out in toluene at a temperature between room temperature and the reflux temperature of the solvent;

or a compound of the formula:

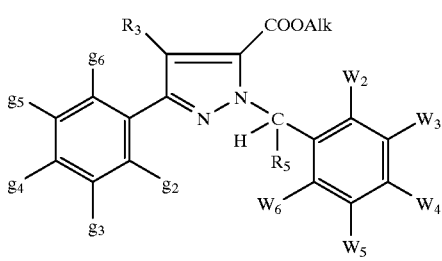
(XXVII)

when the reaction is carried out in N,N-dimethylformamide at a temperature between 0° C. and room temperature; and 2) hydrolyzing either the compound of formula (XXVI) or the compound of formula (XXVII) in an alkaline medium to give respectively:

either the compound of the formula:

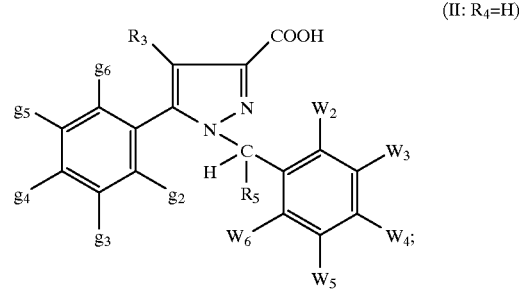
(II: $R_4$=H)

or the compound of the formula:

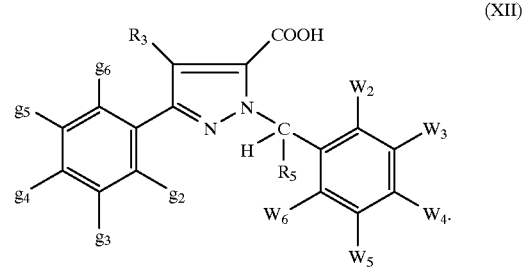
(XII)

16. A process for the preparation of the compounds of formula (XIII) according to claim 14 and their salts, which comprises the steps of:

1) treating a functional derivative of the acid of formula (XII):

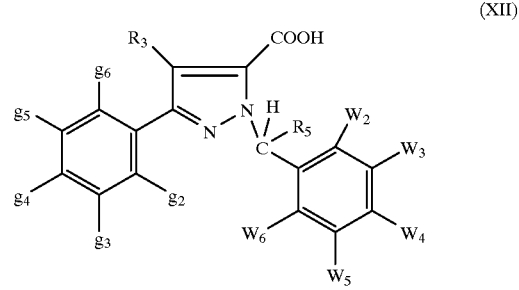
(XII)

in which $g_2$, $g_3$, $g_4$, $g_5$, $g_6$, $w_2$, $w_3$, $w_4$, $w_5$, $w_6$, $R_3$ and $R_5$ are as defined for the compounds of formula (I) in claim 1, with a compound of the formula:

$HX_1$ (XXIV)

in which $X_1$ is as defined for the compounds (I) in claim 1 to give the compound of the formula:

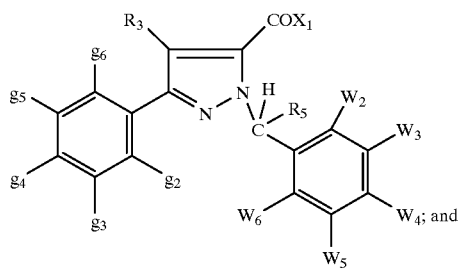

2/ optionally converting the resulting compound to one of its salts.

17. A pharmaceutical composition which contains a compound according to any one of claims 1 to 10, or one of its pharmaceutically acceptable salts, as the active principle.

18. A pharmaceutical composition according to claim 1 in the form of a dosage unit, in which the active principle is mixed with at least one pharmaceutical excipient.

19. A pharmaceutical composition according to claim 18 which contains from 0.5 to 1000 mg of active principle.

20. A pharmaceutical composition according to claim 19, which contains from 2.5 to 250 mg of active principle.

21. A method for the treatment of diseases in which the $CB_2$ receptors are involved which comprises administering to a patient in need of such treatment an effective amount of a compound according to any one of claims 1 to 10.

* * * * *

UNITED STATES PATENT AND TRADEMARK OFFICE
CERTIFICATE OF CORRECTION

PATENT NO.   : 5,925,768
DATED        : July, 20, 1999
INVENTOR(S)  : Francis Barth; Pierre Casellas; Joseph Millan; Didier Oustric; Murielle Rinaldi; and Martine Sarran It is certified that error appears in the above-identified patent and that said Letters Patent is hereby corrected as shown below:

Column 70:
Line 26, the formula

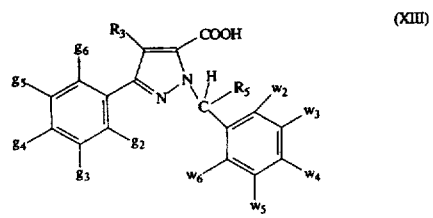 (XIII)

Should read as:

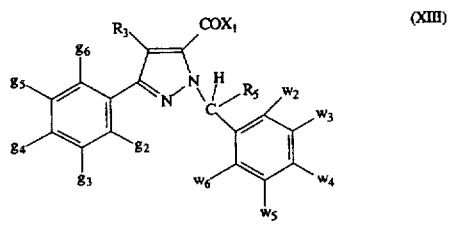 (XIII)

Signed and Sealed this

Seventh Day of August, 2001

*Attest:*

NICHOLAS P. GODICI
*Attesting Officer*   *Acting Director of the United States Patent and Trademark Office*